United States Patent
Osorio

(10) Patent No.: US 12,427,317 B2
(45) Date of Patent: Sep. 30, 2025

(54) CONTINGENT CARDIO-PROTECTION FOR EPILEPSY PATIENTS

(71) Applicant: Ivan Osorio, Leawood, KS (US)

(72) Inventor: Ivan Osorio, Leawood, KS (US)

(73) Assignee: Flint Hills Scientific, L.L.C., Lawrence, KS (US)

( * ) Notice: Subject to any disclaimer, the term of this patent is extended or adjusted under 35 U.S.C. 154(b) by 582 days.

(21) Appl. No.: 16/724,825

(22) Filed: Dec. 23, 2019

(65) Prior Publication Data

US 2020/0121930 A1 Apr. 23, 2020

Related U.S. Application Data

(60) Continuation-in-part of application No. 15/788,078, filed on Oct. 19, 2017, now abandoned, which is a continuation of application No. 14/203,394, filed on Mar. 10, 2014, now Pat. No. 11,305,121, application No. 16/724,825 is a continuation-in-part of application No. 16/679,216, filed on Nov. 10, 2019, now Pat. No. 11,766,565, which is a continuation-in-part of application No. 15/437,155, filed on Feb. 20, 2017, now Pat. No. 10,682,515, which is a division of application No. 14/050,173, filed on Oct. 9, 2013, now Pat. No. 9,579,506, which is a continuation-in-part of application No. 13/601,099, filed on Aug. 31, 2012, now Pat. No. 9,314,633, which is a continuation-in-part of application No. 12/020,195, filed on Jan. 25, 2008, now Pat. No. 8,260,426, which is a continuation-in-part of application No. 12/020,097, filed on Jan. 25, 2008, now Pat. No. 8,565,867.

(60) Provisional application No. 61/799,046, filed on Mar. 15, 2013.

(51) Int. Cl.
*A61N 1/36* (2006.01)
*A61N 1/372* (2006.01)

(52) U.S. Cl.
CPC ...... *A61N 1/36146* (2013.01); *A61N 1/36053* (2013.01); *A61N 1/36064* (2013.01); *A61N 1/36139* (2013.01); *A61N 1/37235* (2013.01); *A61N 1/37247* (2013.01)

(58) Field of Classification Search
CPC ............ A61N 1/36146; A61N 1/36053; A61N 1/36064; A61N 1/36139; A61N 1/37235; A61N 1/37247; A61N 1/36114; A61N 1/36185
See application file for complete search history.

(56) References Cited

U.S. PATENT DOCUMENTS

| 8,417,342 B1 * | 4/2013 | Abell | A61N 1/0509 607/40 |
| 2009/0192567 A1 * | 7/2009 | Armstrong | A61N 1/36114 607/45 |

(Continued)

*Primary Examiner* — Eugene T Wu
(74) *Attorney, Agent, or Firm* — CF3; Stephen Eisenmann

(57) ABSTRACT

Disclosed are methods and systems for treating epilepsy by stimulating a main trunk of a vagus nerve, or a left vagus nerve, when the patient has had no seizure or a seizure that is not characterized by cardiac changes such as an increase in heart rate, and stimulating a cardiac branch of a vagus nerve, or a right vagus nerve, when the patient has had a seizure characterized by cardiac changes such as a heart rate increase.

5 Claims, 30 Drawing Sheets

(56) References Cited

U.S. PATENT DOCUMENTS

| | | | |
|---|---|---|---|
| 2010/0191304 A1* | 7/2010 | Scott | A61B 5/4094 607/45 |
| 2011/0054562 A1* | 3/2011 | Gliner | A61N 1/0551 607/45 |
| 2012/0143286 A1* | 6/2012 | Hahn | A61N 1/36185 607/2 |

* cited by examiner

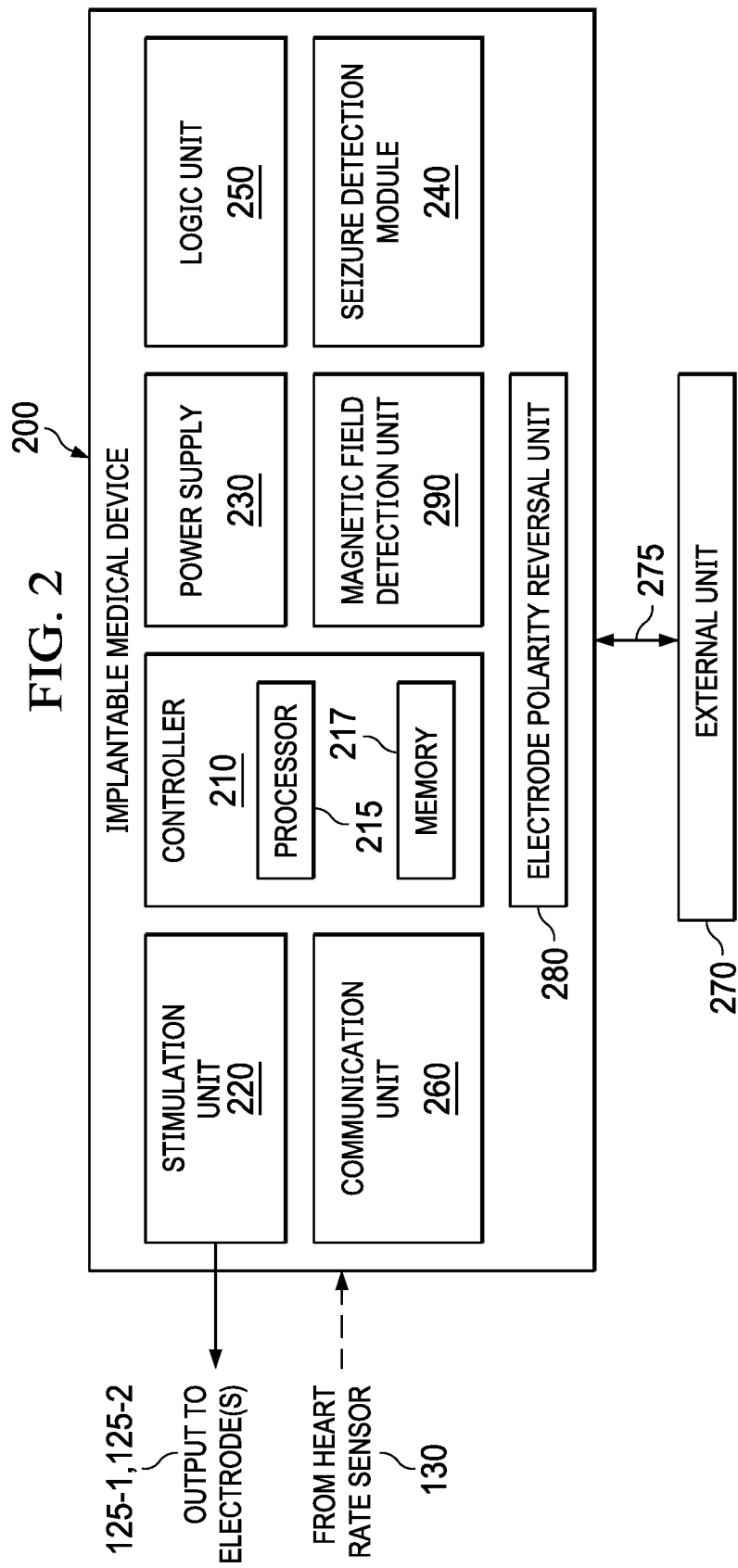

CONTINGENT CARDIO-PROTECTION FOR EPILEPSY PATIENTS

CROSS-REFERENCE TO RELATED APPLICATIONS

This presently being filed application is a continuation-in-part of and claims priority to co-pending U.S. patent application Ser. No. 15/788,078 entitled "Programmable Autotitrating of Electrical Parameters of Implantable Medical Device", filed on Oct. 19, 2017, which is a continuation of and claims priority to U.S. patent application Ser. No. 14/203,394 entitled "Programmable Autotitrating of Electrical Parameters of Implantable Medical Device", filed on Mar. 10, 2014 and claims priority to U.S. Provisional Application No. 61/799,046 filed on Mar. 15, 2013 and this presently being filed application is a continuation-in-part of and claims priority to co-pending U.S. patent application Ser. No. 16/679,216, entitled "Contingent Cardio-Protection For Epilepsy Patients", filed on Nov. 10, 2019 which is a continuation-in-part of and claims priority to co-pending U.S. patent application Ser. No. 15/437,155 entitled "Contingent Cardio-Protection For Epilepsy Patients", filed on Feb. 20, 2017, which claims priority to and is a divisional application of U.S. patent application Ser. No. 14/050,173 entitled "Contingent Cardio-Protection For Epilepsy Patients", filed on Oct. 9, 2013 (now U.S. Pat. No. 9,579,506), which claims priority to and is a continuation-in-part of U.S. patent application Ser. No. 13/601,099 entitled "Contingent Cardio-Protection For Epilepsy Patients", filed on Aug. 31, 2012 (now U.S. Pat. No. 9,314,633), which claims priority to and is a continuation-in-part of U.S. patent application Ser. No. 12/020,195 entitled "Method, Apparatus and System for Bipolar Charge Utilization during Stimulation by an Implantable Medical Device", filed on Jan. 25, 2008 (now U.S. Pat. No. 8,260,426) and claims priority to and is a continuation-in-part of U.S. patent application Ser. No. 12/020,097 entitled "Changeable Electrode Polarity Stimulation by an Implantable Medical Device", filed on Jan. 25, 2008 (now U.S. Pat. No. 8,565,867) all of which are incorporated herein by reference in their entireties.

BACKGROUND OF THE DISCLOSURE

This disclosure relates generally to medical devices, and, more particularly, to methods, apparatus, and systems for performing vagus nerve stimulation (VNS) for treating epileptic seizures characterized by cardiac changes, including ictal tachycardia.

DESCRIPTION OF THE RELATED ART

While seizures are the best known and most studied manifestation of epilepsy, cardiac alterations are prevalent and may account for the high rate of sudden unexpected death (SUDEP) in these patients. These alterations may include changes in rate (most commonly tachycardia, rarely bradycardia or asystole), rhythm (PACs, PVCs,), conduction (e.g., bundle branch block) and repolarization abnormalities (e.g., Q-T prolongation, which occurs primarily during (ictal) but also between seizures (inter-ictally). In addition, S-T segment depression (a sign of myocardial ischemia) is observed during epileptic seizures. Significant elevations in heart-type fatty acid binding protein (H-FABP), a cytoplasmic low-molecular weight protein released into the circulation during myocardial injury have been documented in patients with epilepsy and without evidence of coronary artery disease, not only during seizures but also during free-seizure periods. H-FABP is a more sensitive and specific marker of myocardial ischemia than troponin I or CK-MB. Elevations in H-FABP appear to be un-correlated with duration of illness, of the recorded seizures, or with the Chalfont severity score of the patients.

The cardiac alterations in epilepsy patients, both during and between seizures, have a multi-factorial etiology, but a vago-sympathetic imbalance seems to play a prominent role in their generation. The majority of epileptic seizures enhance the sympathetic tone (plasma noradrenaline and adrenaline rise markedly after seizure onset) causing tachycardia, arterial hypertension and increases in the respiratory rate, among others. Recurrent and frequent exposure to the outpouring of catecholamines associated with seizures in patients with pharmaco-resistant epilepsies may, for example, account for abnormalities that increase the risk of sudden death such as prolongation of the Q-T interval which leads to often fatal tachyarrhythmias such as torsade de pointe. Further evidence in support of the role of catecholamines in SUDEP is found in autopsies of SUDEP victims, revealing interstitial myocardial fibrosis (a risk factor for lethal arrhythmias), myocyte vacuolization, atrophy of cardiomyocytes, leukocytic infiltration, and perivascular fibrosis. Restoration of the sympathetic-parasympathetic tone to normal levels, a therapeutic objective that may be accomplished by enhancing parasympathetic activity through among others, electrical stimulation of the vagus nerve, may decrease the rate and severity of cardiac and autonomic co-morbidities in these patients.

While there have been significant advances over the last several decades in treatments for epileptic seizures, the management of co-morbidities—in particular the cardiac alterations associated with seizures—remains largely unaddressed. There is a need for improved epilepsy treatments that address cardiac impairments associated with seizures. Pharmacological therapies for neurological diseases (including epilepsy) have been available for many decades. A more recent treatment for neurological disorders involves electrical stimulation of a target tissue to reduce symptoms or effects of the disorder. Such therapeutic electrical signals have been successfully applied to brain, spinal cord, and cranial nerves tissues improve or ameliorate a variety of conditions. A particular example of such a therapy involves applying an electrical signal to the vagus nerve to reduce or eliminate epileptic seizures, as described in U.S. Pat. Nos. 4,702,254, 4,867,164, and 5,025,807, which are hereby incorporated herein by reference in their entirety.

The endogenous electrical activity (i.e., activity attributable to the natural functioning of the patient's own body) of a neural structure may be modulated in a variety of ways. One such way is by applying exogenous (i.e., from a source other than the patient's own body) electrical, chemical, or mechanical signals to the neural structure. In some embodiments, the exogenous signal ("neurostimulation" or "neuromodulation") may involve the induction of afferent action potentials, efferent action potentials, or both, in the neural structure. In some embodiments, the exogenous (therapeutic) signal may block or interrupt the transmission of endogenous (natural) electrical activity in the target neural structure. Electrical signal therapy may be provided by implanting an electrical device underneath the skin of a patient and delivering an electrical signal to a nerve such as a cranial nerve.

In one embodiment, the electrical signal therapy may involve detecting a symptom or event associated with the patient's medical condition, and the electrical signal may be delivered in response to the detection. This type of stimulation is generally referred to as "closed-loop," "active," "feedback," "contingent" or "triggered" stimulation. Alternatively, the system may operate according to a predetermined program to periodically apply a series of electrical pulses to the nerve intermittently throughout the day, or over another predetermined time interval. This type of stimulation is generally referred to as "open-loop," "passive," "non-feedback," "non-contingent" or "prophylactic," stimulation.

In other embodiments, both open- and closed-loop stimulation modes may be used. For example, an open-loop electrical signal may operate as a "default" program that is repeated according to a programmed on-time and off-time until a condition is detected by one or more body sensors and/or algorithms. The open-loop electrical signal may then be interrupted in response to the detection, and the closed-loop electrical signal may be applied—either for a predetermined time or until the detected condition has been effectively treated. The closed-loop signal may then be interrupted, and the open-loop program may be resumed. Therapeutic electrical stimulation may be applied by an implantable medical device (IMD) within the patient's body or, in some embodiments, externally.

Closed-loop stimulation of the vagus nerve has been proposed to treat epileptic seizures. Many patients with intractable, refractory seizures experience changes in heart rate and/or other autonomic body signals near the clinical onset of seizures. In some instances the changes may occur prior to the clinical onset, and in other cases the changes may occur at or after the clinical onset. Where the changes involves heart rate, most often the rate increases, although in some instances a drop or a biphasic change (up-then-down or down-then-up) may occur. It is possible using a heart rate sensor to detect such changes and to initiate therapeutic electrical stimulation (e.g., VNS) based on the detected change. The closed-loop therapy may be a modified version of an open-loop therapy. See, e.g., U.S. Pat. Nos. 5,928,272, and 6,341,236, each hereby incorporated by reference herein. The detected change may also be used to warn a patient or third party of an impending or occurring seizure.

VNS therapy for epilepsy patients typically involves a train of electrical pulses applied to the nerve with an electrode pair including a cathode and an anode located on a left or right main vagal trunk in the neck (cervical) area. Only the cathode is capable of generating action potentials in nerve fibers within the vagus nerve; the anode may block some or all of the action potentials that reach it (whether endogenous or exogenously generated by the cathode). VNS as an epilepsy therapy involves modulation of one or more brain structures. Therefore, to prevent the anode from blocking action potentials generated by the cathode from reaching the brain, the cathode is usually located proximal to the brain relative to the anode. For vagal stimulation in the neck area, the cathode is thus usually the upper electrode and the anode is the lower electrode. This arrangement is believed to result in partial blockage of action potentials distal to or below the anode (i.e., those that would travel through the vagus nerve branches innervating the lungs, heart and other viscerae). Using an upper-cathode/lower-anode arrangement has also been favored to minimize any effect of the vagus nerve stimulation on the heart.

Stimulation of the left vagus nerve, for treatment of epilepsy has complex effects on heart rate (see Frei & Osorio, Epilepsia 2001), one of which includes slowing of the heart rate, while stimulation of the right vagus nerve has a more prominent bradycardic effect. Electrical stimulation of the right vagus nerve has been proposed for use in the operating room to slow the heart during heart bypass surgery, to provide a surgeon with a longer time period to place sutures between heartbeats (see, e.g., U.S. Pat. No. 5,651, 373). Some patents discussing VNS therapy for epilepsy treatment express concern with the risk of inadvertently slowing the heart during stimulation. In U.S. Pat. No. 4,702,254, it is suggested that by locating the VNS stimulation electrodes below the inferior cardiac nerve, "minimal slowing of the heart rate is achieved" (col. 7 lines 3-5), and in U.S. Pat. No. 6,920,357, the use of a pacemaker to avoid inadvertent slowing of the heart is disclosed.

Cranial nerve stimulation has also been suggested for disorders outside the brain such as those affecting the gastrointestinal system, the pancreas (e.g., diabetes, which often features impaired production of insulin by the islets of Langerhans in the pancreas), or the kidneys. Electrical signal stimulation of either the brain alone or the organ alone may have some efficacy in treating such medical conditions, but may lack maximal efficacy.

While electrical stimulation has been used for many years to treat a number of conditions, a need exists for improved VNS methods of treating epilepsy and its cardiac co-morbidities as well as other brain and non-brain disorders.

SUMMARY OF THE DISCLOSURE

In one aspect, the present disclosure relates to a method of treating a patient having epilepsy comprising receiving at least one body data stream, analyzing the at least one body data stream using a seizure or event detection algorithm to detect whether or not the patient is having and/or has had an epileptic seizure, receiving a cardiac signal of the patient, applying a first electrical signal to a vagus nerve of the patient based on a determination that the patient is not having and/or has not had an epileptic seizure characterized by a decrease in the patient's heart rate, wherein the first electrical signal is not a vagus nerve conduction blocking electrical signal, and applying a second electrical signal to a vagus nerve of the patient based on a determination that the patient is having and/or has had an epileptic seizure characterized by a decrease in the patient's heart rate, wherein the second electrical signal is a pulsed electrical signal that blocks action potential conduction in the vagus nerve.

In one aspect, the present disclosure relates to a method of treating a patient having epilepsy comprising sensing a cardiac signal and a kinetic signal of the patient, analyzing at least one of the cardiac signal and the kinetic signal; determining whether or not the patient has had an epileptic seizure based on the analyzing; in response to a determination that the patient has had an epileptic seizure, determining whether or not the seizure is characterized by a decrease in the patient's heart rate, applying a first electrical signal to a vagus nerve of the patient based on a determination that the patient has had an epileptic seizure characterized by a decrease in the patient's heart rate, wherein the first electrical signal is a pulsed electrical signal that blocks action potential conduction in the vagus nerve; and applying a second electrical signal to a vagus nerve of the patient based on one of a) a determination that the patient has not had an epileptic seizure, and b) a determination that the patient has had an epileptic seizure that is not characterized by a decrease in the patient's heart rate, wherein the second electrical signal is not a vagus nerve conduction blocking electrical signal.

In one aspect, the present disclosure relates to a system for treating a medical condition in a patient, comprising at least one electrode coupled to a vagus nerve of the patient, a programmable electrical signal generator, a sensor for sensing at least one body data stream, a seizure detection module capable of analyzing the at least one body data stream and determining, based on the analyzing, whether or not the patient is having and/or has had an epileptic seizure, a heart rate determination unit capable of determining a heart rate of a patient proximate in time to an epileptic seizure detected by the seizure detection module, and a logic unit for applying a first electrical signal to the vagus nerve using the at least one electrode based on a determination by the seizure detection module that the patient is having and/or has had an epileptic seizure characterized by a decrease in the patient's heart rate, wherein the first electrical signal is a pulsed electrical signal that blocks action potential conduction in the vagus nerve, and for applying a second electrical signal to the vagus nerve using the at least one electrode as a cathode based upon one of a) a determination that the patient is not having and/or has not had an epileptic seizure, and b) a determination that the patient is having and/or has had an epileptic seizure that is not characterized by a decrease in the patient's heart rate, wherein the second electrical signal is not a vagus nerve conduction blocking electrical signal. In one embodiment, the seizure detection module may comprise the heart rate determination unit.

In one aspect, the present disclosure relates to a method of treating a patient having epilepsy comprising applying a first electrical signal to a vagus nerve of the patient, wherein the first electrical signal is an open-loop electrical signal having a programmed on-time and a programmed off-time, sensing at least one body signal of the patient, determining the start of an epileptic seizure based on the at least one body signal, determining whether or not the seizure is characterized by a decrease in the patient's heart rate, applying a second, closed-loop electrical signal to a vagus nerve of the patient based on a determination that the epileptic seizure is not characterized by a decrease in the patient's heart rate, and applying a third, closed-loop electrical signal to a vagus nerve of the patient based on a determination that the seizure is characterized by a decrease in the patient's heart rate, wherein the third electrical signal is applied to block action potential conduction on the vagus nerve.

In one aspect, the present disclosure relates to a method of controlling a heart rate of an epilepsy patient comprising sensing a kinetic signal of the patient; analyzing said kinetic signal to determine at least one kinetic index; receiving a cardiac signal of the patient; analyzing the cardiac signal to determine the patient's heart rate; determining if the patient's heart rate is commensurate with the at least one kinetic index; and applying a first electrical signal to a vagus nerve of the patient based on a determination that the patient's heart rate is not commensurate with the kinetic index. In one embodiment, the at least one kinetic index comprises at least one of an activity level or an activity type of the patient, and determining if the heart rate is commensurate with the kinetic index comprises determining if the heart rate is commensurate with the at least one of an activity level or an activity type.

In one aspect, the present disclosure relates to a method of controlling a heart rate of an epilepsy patient comprising sensing at least one of a kinetic signal and a metabolic (e.g., oxygen consumption) signal of the patient; receiving a cardiac signal of the patient; analyzing the cardiac signal to determine the patient's heart rate; determining if the patient's heart rate is commensurate with the at least one of a kinetic and a metabolic signal of the patient; and applying a first electrical signal to a vagus nerve of the patient based on a determination that the patient's heart rate is not commensurate with the at least one of a kinetic signal and a metabolic signal. In one embodiment, the method further comprises determining at least one of an activity level or an activity type of the patient based on the at least one of a kinetic and a metabolic signal, and determining if the heart rate is commensurate with the kinetic signal comprises determining if the heart rate is commensurate with the at least one of an activity level or an activity type.

In one aspect, the present disclosure relates to a method of treating a patient having epilepsy comprising sensing at least one body signal of the patient; determining whether or not the patient is having or has had an epileptic seizure based on the at least one body signal; sensing a cardiac signal of the patient; determining whether or not the seizure is associated with a change in the patient's cardiac signal; applying a first therapy to a vagus nerve of the patient based on a determination that the patient is having or has had an epileptic seizure that is not associated with a change in the patient's cardiac signal, wherein the first therapy is selected from an electrical, chemical, mechanical (e.g., pressure) or thermal signal. The method further comprises applying a second therapy to a vagus nerve of the patient based on a determination that the patient has had an epileptic seizure associated with a change in the patient's cardiac signal, wherein the second therapy is selected from an electrical, chemical, mechanical (e.g., pressure) or thermal signal. In some embodiments, a third therapy may be applied to a vagus nerve based a determination that the patient has not had an epileptic seizure, wherein the third therapy is selected form an electrical, chemical, mechanical or thermal signal.

In some embodiments, the present disclosure relates to a method of automatically titrating an electrical therapy administered to a patient by an implanted medical device to a target dosage, comprising: programming the medical device with an electrical therapy, wherein the programmed electrical therapy comprises a first target value for a first electrical therapy parameter defining the electrical therapy; programming at least one titration parameter for automatically adjusting the first electrical therapy parameter from a first value to the first target value over a titration time period of at least two days, wherein the at least one titration parameter is selected from the titration time period, a titration step interval, and a titration step magnitude; initiating the electrical therapy, wherein the first electrical therapy parameter comprises said first value; and automatically titrating the electrical therapy by making a plurality of adjustments to the value of the first electrical therapy parameter, whereby the first electrical therapy parameter is changed from the first value to the first target value according to a titration function.

In some embodiments, the present disclosure relates to a method of automatically titrating an electrical therapy administered to a patient by an implanted medical device to a target dosage, comprising: programming the medical device with an electrical therapy, wherein programming comprises providing a first target value for a first electrical therapy parameter characterizing the electrical therapy; programming at least one titration parameter for automatically adjusting the first electrical therapy parameter from a first value to the first target value over a titration time of at least five days, wherein the at least one titration parameter is selected from the titration time period, a titration step interval, and a titration step magnitude; initiating the electrical therapy, wherein the first electrical therapy parameter comprises said first value; automatically titrating the electrical therapy by making a plurality of adjustments to the value of the at least a first electrical therapy parameter, whereby the first electrical therapy parameter is changed from the first value to the first target value according to a first titration function; receiving a body signal after at least one of said plurality of adjustments to the value of the first electrical therapy parameter; determining whether there is an adverse effect associated with the at least one of said plurality of adjustments, based upon said body signal; returning the value of said first electrical therapy parameter to a prior value to provide a prior electrical therapy program, in response to determining that there is an adverse effect associated with said at least one of said plurality of adjustments; and providing said prior electrical therapy program to said patient. In one embodiment, the adverse effect is selected from discomfort, pain, dyspnea, voice alteration, increased heart rate, and decreased heart rate.

In some embodiments, the present disclosure relates to a medical device system for providing an electrical therapy, comprising: a programmer for programming an implantable medical device with an electrical therapy, wherein the programmer enables a user to program into the medical device a first value for a first electrical therapy parameter characterizing the electrical therapy, a first target value for the first electrical therapy parameter, and at least one titration parameter for automatically adjusting the first electrical therapy parameter from a first value to the first target value over a titration time period of at least two days, wherein the at least one titration parameter is selected from the titration time period, a titration step interval, and a titration step magnitude; an electrode configured to deliver an electrical therapy characterized by a plurality of parameters to a patient; and an implantable medical device, comprising: an electrical therapy module to provide the electrical therapy to the patient using said electrode; and a therapy titration module configured to automatically titrate the electrical therapy by making a plurality of adjustments to the value of the first electrical therapy parameter, whereby the first electrical therapy parameter is changed from the first value to the first target value according to a titration function. In one embodiment, the implantable medical device may comprise a body data module capable of receiving a body signal from the patient, a feedback module configured to provide feedback data to the therapy titration module, wherein the feedback data is based upon one of said body data and a manual input from the patient or a caregiver, and wherein the therapy titration module comprises a dynamic adjustment unit configure to return the value of the first electrical therapy parameter to a previous value after at least a first adjustment, based on said feedback data.

In some embodiments, the present disclosure relates to a non-transitory computer readable program storage unit encoded with instructions that, when executed by a computer, perform a method as described above.

BRIEF DESCRIPTION OF THE DRAWINGS

The disclosure may be understood by reference to the following description taken in conjunction with the accompanying drawings, in which like reference numerals identify like elements, and in which:

FIG. 2 illustrates a block diagram depiction of an implantable medical device of FIG. 1, in accordance with one illustrative embodiment of the present disclosure;

Figure 1A:
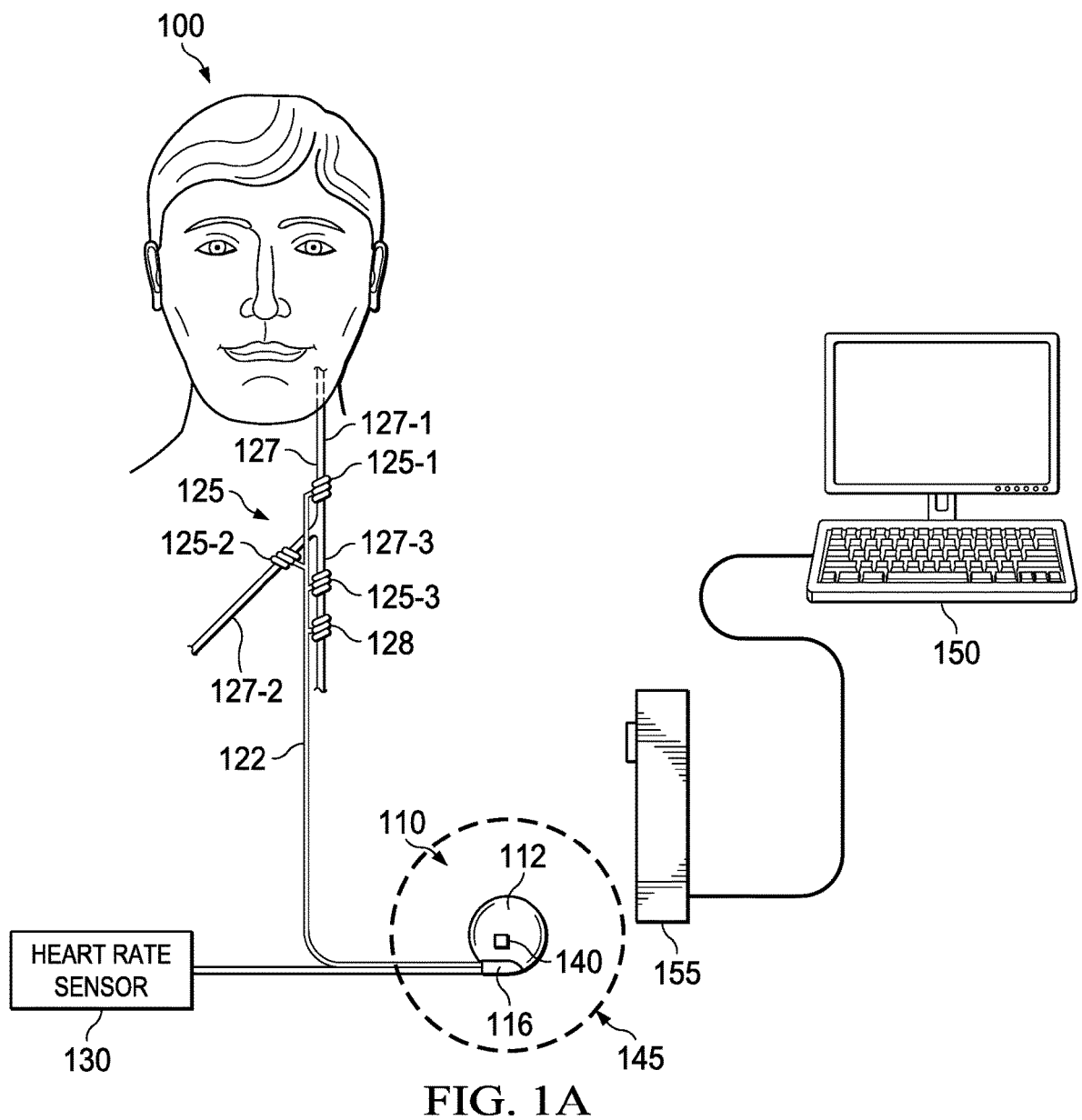
FIGS. 1A-1E provide stylized diagrams of an implantable medical device implanted into a patient's body for providing first and second electrical signals to a vagus nerve of a patient for treating epileptic seizures, in accordance with one illustrative embodiment of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are provided in detail. In any actual embodiment, numerous implementation-specific decisions must be made to achieve the design-specific goals. Such a development effort, while possibly complex and time-consuming, would nevertheless be a routine task for persons of skill in the art given this disclosure.

This application does not intend to distinguish between components that differ in name but not function. "Including" and "includes" are used in an open-ended fashion, and should be interpreted to mean "including, but not limited to." "Couple" or "couples" are intended to mean either a direct or an indirect electrical connection. "Direct contact," "direct attachment," or providing a "direct coupling" indicates that a surface of a first element contacts the surface of a second element with no substantial attenuating medium there between. Small quantities of substances, such as bodily fluids, that do not substantially attenuate electrical connections do not vitiate direct contact. "Or" is used in the inclusive sense (i.e., "and/or") unless a specific use to the contrary is explicitly stated.

"Electrode" or "electrodes" may refer to one or more stimulation electrodes (i.e., electrodes for applying an electrical signal generated by an IMD to a tissue), sensing electrodes (i.e., electrodes for sensing a body signal), and/or electrodes capable of either stimulation or sensing. "Cathode" and "anode" have their standard meanings, as the electrode at which current leaves the IMD system and the electrode at which current enters the IMD system, respectively. Reversing the polarity of the electrodes can be effected by any switching technique known in the art.

A "pulse" is used herein to refer to a single application of electrical charge from the cathode to target neural tissue. A pulse may include both a therapeutic portion (in which most or all of the therapeutic or action-potential-generating effect occurs) and a charge-balancing portion in which the polarity of the electrodes are reversed and the electrical current is allowed to flow in the opposite direction to avoid electrode and/or tissue damage. Individual pulses are separated by a time period in which no charge is delivered to the nerve, which can be called the "interpulse interval." A "burst" is used herein to refer to a plurality of pulses, which may be separated from other bursts by an interburst interval in which no charge is delivered to the nerve. The interburst intervals have a duration exceeding the interpulse interval duration. In one embodiment, the interburst interval is at least twice as long as the interpulse interval. The time period between the end of the last pulse of a first burst and the initiation of the first pulse of the next subsequent burst can be called the "interburst interval." In one embodiment, the interburst interval is at least 100 msec.

A plurality of pulses can refer to any of (a) a number of consecutive pulses within a burst, (b) all the pulses of a burst, or (c) a number of consecutive pulses including the final pulse of a first burst and the first pulse of the next subsequent burst.

"Stimulate," "stimulating" and "stimulator" may generally refer to applying a signal, stimulus, or impulse to neural tissue (e.g., a volume of neural tissue in the brain or a nerve) for affecting it neuronal activity. While the effect of such stimulation on neuronal activity is termed "modulation," for simplicity, the terms "stimulating" and "modulating", and variants thereof, are sometimes used interchangeably herein. The modulation effect of a stimulation signal on neural tissue may be excitatory or inhibitory, and may potentiate acute and/or long-term changes in neuronal activity. For example, the modulation effect of a stimulation signal may comprise: (a) initiating action potentials in the target neural tissue; (b) inhibition of conduction of action potentials (whether endogenous or exogenously generated, or blocking their conduction (e.g., by hyperpolarizing or collision blocking), (c) changes in neurotransmitter/neuromodulator release or uptake, and (d) changes in neuroplasticity or neurogenesis of brain tissue. Applying an electrical signal to an autonomic nerve may comprise generating a response that includes an afferent action potential, an efferent action potential, an afferent hyperpolarization, an efferent hyperpolarization, an afferent sub-threshold depolarization, and/or an efferent sub-threshold depolarization. The terms tachycardia and bradycardia are used here in a relative (i.e., any decrease or decrease in heart rate relative to a reference value) or in an absolute sense (i.e., a pathological change relative to a normative value). In particular, "tachycardia is used interchangeably with an increase heart rate and "bradycardia" may be used interchangeably with a decrease in heart rate.

A variety of stimulation therapies may be provided in embodiments of the present disclosure. Different nerve fiber types (e.g., A, B, and C-fibers that may be targeted) respond differently to stimulation from electrical signals because they have different conduction velocities and stimulation threshold. Certain pulses of an electrical stimulation signal, for example, may be below the stimulation threshold for a particular fiber and, therefore, may generate no action potential. Thus, smaller or narrower pulses may be used to avoid stimulation of certain nerve fibers (such as C-fibers) and target other nerve fibers (such as A and/or B fibers, which generally have lower stimulation thresholds and higher conduction velocities than C-fibers). Additionally, techniques such as a pre-pulse may be employed wherein axons of the target neural structure may be partially depolarized (e.g., with a pre-pulse or initial phase of a pulse) before a greater current is delivered to the target (e.g., with a second pulse or an initial phase such a stair step pre-pulse to deliver a larger quantum of charge). Furthermore, opposing polarity phases separated by a zero current phase may be used to excite particular axons or postpone nerve fatigue during long term stimulation.

Cranial nerve stimulation, such as vagus nerve stimulation (VNS), has been proposed to treat a number of medical conditions, including epilepsy and other movement disorders, depression and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the variety of disorders for which cranial nerve stimulation has been proposed or suggested, the fact that detailed neural pathways for many (if not all) cranial nerves remain relatively unknown, makes predictions of efficacy for any given disorder difficult or impossible. Even if such pathways were known, the precise stimulation parameters that would modulate particular pathways relevant to a particular disorder generally cannot be predicted.

Cardiac signals suitable for use in embodiments of the present disclosure may comprise one or more of an electrical (e.g., EKG), acoustic (e.g., phonocardiogram or ultrasound/ECHO), force or pressure (e.g., apexcardiogram), arterial pulse pressure and waveform or thermal signals that may be recorded and analyzed to extract features such as heart rate, heart rate variability, rhythm (regular, irregular, sinus, ventricular, ectopic, etc.), morphology, etc.

It appears that sympatho-vagal imbalance (lower vagal and higher sympathetic tone) plays an important role in generation of a wide spectrum of ictal and interictal alterations in cardiac dynamics, ranging from rare unifocal PVCs to cardiac death. Without being bound by theory, restoration of the vagal tone to a level sufficient to counteract the pathological effects of elevated catecholamines may serve a cardio-protective purpose that would be particularly beneficial in patients with pharmaco-resistant epilepsies, who are at highest risk for SUDEP.

In one embodiment, the present disclosure provides methods and apparatus to increase cardiac vagal tone in epilepsy patients by timely delivering therapeutic electrical currents to the trunks of the right or left vagus nerves or to their cardiac rami (branches), in response to increases in sympathetic tone, by monitoring among others, heart rate, heart rhythm, EKG morphology, blood pressure, skin resistance, catecholamine or their metabolites and neurological signals such as EEG/ECoG, kinetic (e.g., amplitude velocity, direction of movements) and cognitive (e.g., complex reaction time).

In one embodiment, the present disclosure provides a method of treating a medical condition selected from the group consisting of epilepsy, neuropsychiatric disorders (including but not limited to depression), eating disorders/obesity, traumatic brain injury, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, gastrointestinal disorders, kidney disorders, and reproductive endocrine disorders (including infertility).

Figure 1B:
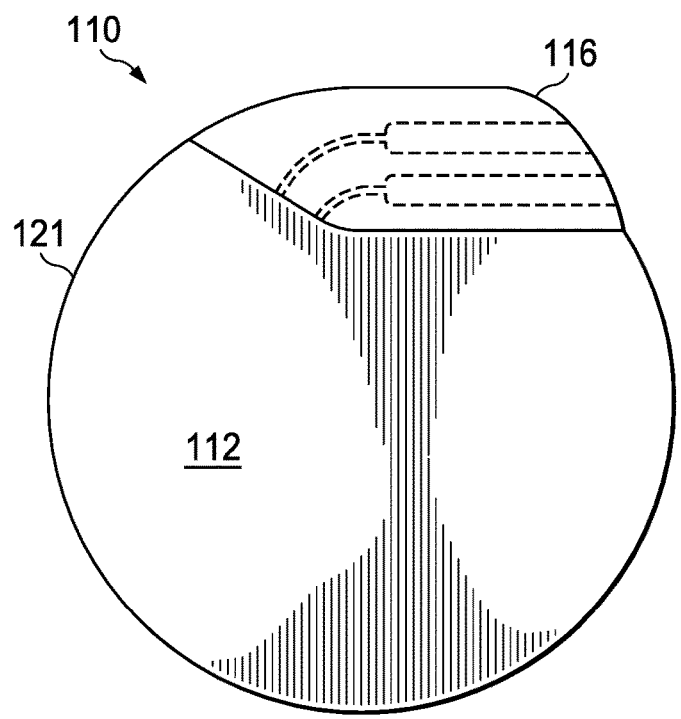

FIGS. 1A-1E depict a stylized implantable medical system 100 for implementing one or more embodiments of the present disclosure. FIGS. 1A and 1B illustrate an electrical signal generator 110 having main body 112 comprising a case or shell (commonly referred to as a "can") 121 (FIG. 1B) with a header 116 for connecting to a lead assembly 122. An electrode assembly 125, preferably comprising at least an electrode pair, is conductively connected to the distal end of an insulated, electrically conductive lead assembly 122, which preferably comprises a plurality of lead wires (at least one wire for each electrode of the electrode assembly 125). Lead assembly 122 is attached at its proximal end to one or more connectors on header 116 (FIG. 1B).

Electrode assembly 125 may be surgically coupled to a target tissue for delivery of a therapeutic electrical signal, which may be a pulsed electrical signal. The target tissue may be a cranial nerve, such as a vagus nerve 127 (FIGS. 1A, 1C-E) or another cranial nerve such as a trigeminal nerve. Electrode assembly 125 includes one or more electrodes 125-1, 125-2, 125-3, which may be coupled to the target tissue. The electrodes may be made from any of a variety of conductive metals known in the art, e.g., platinum, iridium, oxides of platinum or iridium, or combinations of the foregoing. In one embodiment, the target tissue is a vagus nerve 127, which may include an upper main trunk portion 127-1 above a cardiac branch 127-2, and a lower main trunk portion 127-3 below the cardiac branch.

Figure 1C:
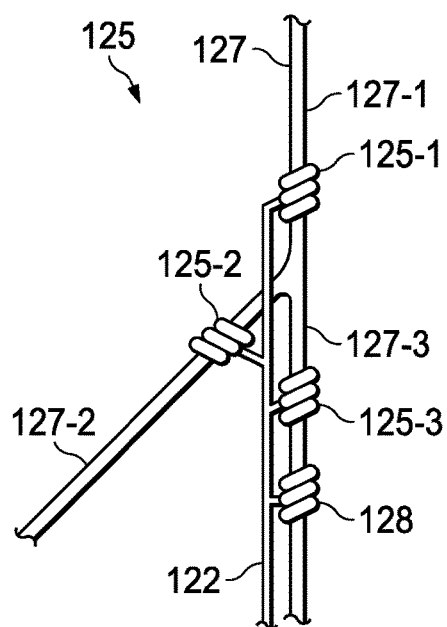

In one embodiment, at least one electrode may be coupled to the main trunk of the vagus nerve, and at least one electrode 125-2 may be coupled to a cardiac branch 127-2 of the vagus nerve (FIG. 1C). The at least one main trunk electrode may be coupled to an upper main trunk 127-1 (e.g., electrode 125-1, FIG. 1C) or a lower main trunk 127-3 (e.g., electrode 125-3). The at least one main trunk electrode (125-1, 125-3) may be used as a cathode to provide a first electrical signal to the upper (127-1) or lower (127-3) main trunk. Cardiac branch electrode 125-2 may be used as a cathode to provide a second electrical signal to cardiac branch 127-2. An additional electrode to function as the anode may be selected from one or more of the other electrodes in electrode assembly 125, can 121, or a dedicated anode.

In some embodiments (FIGS. 1D, 1E), electrode assembly 125 may include a main trunk electrode pair comprising a cathode 125-1*a* and an anode 125-1*b* for coupling to a main trunk of a vagus nerve 127. The main trunk electrode pair 125-1*a*, 125-1*b* may be coupled to an upper main trunk 127-1 of a vagus nerve (FIG. 1D), or to a lower main trunk 127-3 (FIG. 1E) for delivering a first electrical signal. Without being bound by theory, it is believed that few or no vagal afferent fibers in the lower main trunk 127-3 pass into cardiac branch 127-2 and, accordingly, that effects of the first electrical signal on cardiac function may be minimized by coupling electrode pair 125-1*a* and 125-1*b* to the lower main trunk 127-3 instead of upper main trunk 127-1. Cardiac effects may also be minimized by alternative embodiments in which the first electrical signal is applied to a lower main trunk 127-3 using a single electrode (e.g., 125-3, FIG. 1C) as a cathode and an anode that is not coupled to the vagus nerve 127 (e.g., by using can 121 as an anode).

In some embodiments (FIGS. 1D, 1E), electrode assembly 125 may include a cardiac branch electrode pair comprising a cathode 125-2*a* and an anode 125-2*b* for coupling to a cardiac branch of a vagus nerve. The second cardiac branch electrode pair may be used to provide a second electrical signal to a cardiac branch of the nerve to affect the cardiac function of the patient.

Referring again to FIGS. 1C-1E, a first electrical signal may be provided to generate afferent action potentials in a main trunk of a vagus nerve to modulate electrical activity of the patient's brain without significantly affecting the patient's heart rate. The second electrical signal may generate efferent action potentials to module the cardiac activity of the patient, and in particular to slow the patient's heart rate (e.g., to treat an epilepsy patient having seizures characterized by ictal tachycardia) and maintain or restore a sympathetic/parasympathetic balance to a non-pathological state. The first electrical signal may be applied to the main trunk of the vagus nerve in a variety of ways, so long as at least one electrode is coupled to the main trunk as a cathode. As noted, the cathode may be coupled to either an upper (127-1) or lower (127-3) main trunk, and an anode may be provided by any of the other electrodes on the vagus nerve (e.g., 125-1*b*, 125-2*b*, 125-3, FIGS. 1C-1E) or by a separate anode not coupled to the vagus nerve (e.g., can 121). In one alternative embodiment, an electrode 125-3 may be coupled to a lower main trunk 127-3 of the vagus nerve to function as an anode. In yet another embodiment, each individual electrode element in FIGS. 1A-E (e.g., 125-1, 125-2, 125-3, 125-1*a*, 125-1*g*, 125-2*a*, 125-2*b*) may comprise an electrode pair comprising both an anode and a cathode. In an additional embodiment, each individual electrode element may comprise three electrodes (e.g., one serving as cathode and the other two as anodes). Suitable electrode assemblies are available from Cyberonics, Inc., Houston, Tex., USA as the Model 302, PerenniaFlex and PerenniaDura electrode assemblies. In view of the present disclosure, persons of skill in the art will appreciate that many electrode designs could be used in embodiments of the present disclosure including unipolar electrodes.

Embodiments of the present disclosure may comprise electrical signals with either charge-balanced or non-charge-balanced pulses (e.g., monopolar/monophasic, direct current (DC)). Charge-balanced pulses involve a first phase in which the stimulation occurs (i.e., action potentials are induced in target nerve fibers), and a second phase in which the polarity of the electrodes are reversed (i.e., the stimulation phase cathode becomes the charge-balancing phase anode, and vice versa). The result is a pulse having two opposite-polarity phases of equal charge, such that no net charge flows across the electrode during a pulse. Charge-balancing is often used to avoid damage to the electrodes that may result if a pulse results in a net charge flowing across the electrodes.

In some instances, charge-balancing may involve a passive discharge phase as illustrated in, e.g., FIG. 1A of US Publication 2006/0173493, which is hereby incorporated by reference in its entirety. In passive charge-balancing, the charge-balancing phase typically involves allowing a capacitor having a charge equal to the charge applied to the nerve during the stimulation phase to discharge through the polarity-reversed electrodes. Passive charge-balancing typically uses much lower initial current than the stimulation phase, with the current declining to zero over a much longer time period than the pulse width of the stimulation phase. A lower current is typically selected in the charge-balancing phase so as to avoid or minimize nerve recruitment during the charge-balancing phase. In active charge-balancing, the charge-balancing phase is not accomplished by the passive discharge of a capacitor, but by providing a second phase having an opposite polarity but the same charge magnitude (pulse width multiplied by current) as the first phase. As is usually the case with passive charge-balancing, active charge-balancing typically involves a much lower current that is applied over a longer time period than the stimulation phase, so as to avoid nerve recruitment. In some instances, however, the active charge-balancing phase may be used as a second stimulation phase by selecting a current magnitude of the cathode in the charge-balancing phase (typically a second electrode, which may be the anode of the initial stimulation phase) that is sufficient to generate action potentials in nerve fibers of the target tissue.

Embodiments of the present disclosure may be implemented using passive charge balancing or active charge-balancing, and the latter may be provided as a stimulation phase or a non-stimulation phase. Some embodiments may be implemented with non-charge-balanced pulses. Persons of skill in the art, having the benefit of the present disclosure, may select the type of charge balancing (if desired) based upon a number of factors including but not limited to whether or not the charge-balancing is intended to affect the cardiac cycle or not, whether afferent or efferent stimulation is desired, the number and location of available electrodes for applying the electrical signal, the fibers intended to be recruited during a particular phase and their physiological effects, among many other factors.

In the discussion of electrical signals in the present disclosure, unless otherwise stated, references to electrodes as cathodes or anodes refers to the polarities of the electrodes during a stimulation phase of a pulse, whether the pulse is a charge-balanced pulse or a non-charge-balanced pulse (e.g., monopolar/monophasic or DC). It will be appreciated that where charge-balanced pulses are employed, the polarities will be reversed during a charge-balancing phase. Where active charge-balancing is used, cardiac effects may be further amplified or ameliorated, depending upon the location of the electrodes being used.

Returning to FIG. 1A, in some embodiments, a heart rate sensor 130, and/or a kinetic sensor 140 (e.g., a triaxial accelerometer) may be included in the system 100 to sense one or more of a cardiac signal or data stream and a kinetic data stream of the patient. In one embodiment, the heart rate sensor may comprise a separate element 130 that may be coupled to generator 110 through header 116 as illustrated in FIG. 1A. In another embodiment, the electrodes 125-1, 125-2, 125-3 and/or the can 121 may be used as sensing electrodes to sense heart rate. An accelerometer may be provided inside generator 110 in one embodiment to sense a kinetic signal (e.g., body movement) of the patient. One or more of the heart rate sensor 130 and the kinetic sensor 140 may be used by a seizure detection algorithm in the system 100 to detect epileptic seizures. In alternative embodiments, other body signals (e.g., blood pressure, brain activity, blood oxygen/$CO_2$ concentrations, temperature, skin resistivity, etc.) of the patient may be sensed and used by the seizure detection algorithm to detect epileptic seizures. Signal generator 110 may be implanted in the patient's chest in a pocket or cavity formed by the implanting surgeon below the skin (indicated by line 145, FIG. 1A).

Returning to FIGS. 1A and 1C, a first electrode 125-1 may be wrapped or otherwise electrically coupled to an upper main trunk 127-1 of a vagus nerve 127 of the patient, and a second electrode 125-2 may be wrapped or coupled to a cardiac branch 127-2 of the vagus nerve. In one embodiment, a third electrode 125-3 may be coupled to a lower main trunk 127-3 of the vagus nerve below the cardiac branch 127-2 of the vagus nerve, instead of or in addition to first electrode 125-1 coupled to the upper main trunk above the cardiac branch. In some embodiments, third electrode 125-3 may be omitted. Electrode assembly 125 may be secured to the nerve by a spiral anchoring tether 128 (FIG. 1C), which in one embodiment does not include an electrode but in alternative embodiments may contain up to three electrodes that serve as cathode(s) and anode(s) in any possible combination. Lead assembly 122 may further be secured, while retaining the ability to flex, by a suture connection 130 to nearby tissue (FIG. 1C). In particular embodiments, any of first, second and third electrodes 125-1, 125-2, and 125-3 may be used as either a cathode or as an anode. In general, the foregoing electrodes may be used as a cathode when the particular electrode is the closest electrode (among a plurality of electrodes) to the target organ (e.g., heart, brain, stomach, liver, etc.) to be stimulated. While a single electrode (e.g., 125-1, 125-2, or 125-3) is illustrated in connection with upper main trunk 127-1, cardiac branch 127-2, and lower main trunk 127-3 in FIGS. 1A and 1C for simplicity, it will be appreciated that one or more additional electrodes can be provided on each of the foregoing neural structures to provide greater flexibility in stimulation.

In one embodiment, the open helical design of the electrodes 125-1, 125-2, 125-3, is self-sizing, flexible, minimize mechanical trauma to the nerve and allow body fluid interchange with the nerve. The electrode assembly 125 preferably conforms to the shape of the nerve, providing a low stimulation threshold by allowing a large stimulation contact area with the nerve. Structurally, the electrode assembly 125 comprises an electrode ribbon (not shown) for each of electrodes 125-1, 125-2, 125-3, made of a conductive material such as platinum, iridium, platinum-iridium alloys, and/or oxides thereof. The electrode ribbons are individually bonded to an inside surface of an elastomeric body portion of the spiral electrodes 125-1, 125-2, 125-3 (FIG. 1C), which may comprise spiral loops of a multi-loop helical assembly. Lead assembly 122 may comprise three distinct lead wires or a triaxial cable that are respectively coupled to one of the conductive electrode ribbons. One suitable method of coupling the lead wires to the electrodes 125-1, 125-2, 125-3 comprises a spacer assembly such as that disclosed in U.S. Pat. No. 5,531,778, although other known coupling methods may be used.

The elastomeric body portion of each loop may be composed of silicone rubber or other biocompatible elastomeric compounds, and the fourth loop 128 (which may have no electrode in some embodiments) acts as the anchoring tether for the electrode assembly 125.

In one embodiment, electrical pulse generator 110 may be programmed with an external computer 150 using programming software known in the art for stimulating neural structures, and a programming wand 155 to facilitate radio frequency (RF) communication between the external computer 150 (FIG. 1A) and the implanted pulse generator 110. In one embodiment, wand 155 and software permit wireless, non-invasive communication with the generator 110 after surgical implantation. Wand 155 may be powered by internal batteries, and provided with a "power on" light to indicate sufficient power for communications. Another indicator light may be provided to show that data transmission is occurring between the wand and the generator. In other embodiments, wand 155 may be omitted, e.g., where communications occur in the 401-406 MHz bandwidth for Medical Implant Communication Service (MICS band).

In some embodiments of the disclosure, a body data stream may be analyzed to determine whether or not a seizure has occurred. Many different body data streams and seizure detection indices have been proposed for detecting epileptic seizures. Additional details on method of detecting seizure from body data are provided in U.S. Pat. Nos. 8,337,404 and 8,382,667, both issued in the name of the present applicant and both entitled, "Detecting, Quantifying, and/or Classifying Seizures Using Multimodal Data," as well as in co-pending U.S. patent application Ser. No. 13/288,886, filed Nov. 3, 2011, each hereby incorporated by reference in its entirety herein. Seizure detection based on the patient's heart rate (as sensed by implanted or external electrodes), movement (as sensed by, e.g., a triaxial accelerometer), responsiveness, breathing, blood oxygen saturation, skin resistivity/conductivity, temperature, brain activity, and a number of other body data streams are provided in the foregoing patents and co-pending applications.

In one embodiment, the present disclosure provides a method for treating a patient with epilepsy in which a body data stream is analyzed using a seizure detection algorithm to determine whether or not the patient has had an epileptic seizure. As used herein, the term "has had an epileptic seizure" includes instances in which a seizure onset has been detected, as well as instances in which the seizure onset has been detected and the seizure is still ongoing (i.e., the seizure has not ended). If the analysis results in a determination that the patient has not had an epileptic seizure, a signal generator may apply a first electrical signal to a main trunk of a vagus nerve of the patient. If the analysis results in a determination that the patient has had an epileptic seizure, the signal generator may apply a second electrical signal to a cardiac branch of a vagus nerve of the patient. In some embodiments, the application of the first electrical signal to the main trunk is terminated, and only the second electrical signal to the cardiac branch is provided once a seizure is detected.

In alternative embodiments, both the first and second electrical signals may be applied to the main trunk and cardiac branch, respectively, of the vagus nerve in response to a determination that the patient has had a seizure (i.e., the first electrical signal continues to be applied to the main trunk of the vagus nerve and the second signal is initiated). Where both the first and second electrical signals are provided, the two signals may be provided sequentially, or in alternating fashion to the main trunk and the cardiac branch. In one embodiment, the first signal may be provided to the main trunk by using one of the upper main trunk electrode 125-1 or the lower main trunk electrode 125-3 as the cathode and the cardiac branch electrode 125-2 as the anode, or by using both of the upper main trunk electrode and the lower main trunk electrode as the cathode and the anode. The second signal may be provided (e.g., by rapidly changing the polarity of the electrodes) by using the cardiac branch electrode 125-2 as the cathode and a main trunk electrode 125-1 or 125-3 as the anode.

In still other embodiments, the second electrical signal is applied to the cardiac branch of the vagus nerve only if the analysis results in a determination that the patient is having and/or has had an epileptic event that is accompanied by an increase in heart rate, and the second electrical signal is used to lower the heart rate back towards a rate that existed prior to the seizure onset. Without being bound by theory, the present inventors believe that slowing the heart rate at the onset of seizures—particularly where the seizure is accompanied by an increase in heart rate—may improve the ability of VNS therapy to provide cardio-protective benefits.

Prior patents describing vagus nerve stimulation as a medical therapy have cautioned that undesired slowing of the heart rate may occur, and have proposed various methods of avoiding such a slowing of the heart rate. In U.S. Pat. No. 6,341,236, it is suggested to sense heart rate during delivery of VNS and if a slowing of the heart rate is detected, either suspending delivery of the VNS signal or pacing the heart using a pacemaker. The present application discloses a VNS system that detects epileptic seizures, particularly epileptic seizures accompanied by an increase in heart rate, and intentionally applies an electrical signal to slow the heart rate in response to such a detection. In another aspect, the present application discloses VNS systems that provide a first electrical signal to modulate only the brain during periods in which no seizure has been detected, and either 1) a second electrical signal to modulate only the heart (to slow its rate) or 2) both a first electrical signal to the brain and a second electrical signal to the heart, in response to a detection of the onset of an epileptic seizure. These electrical signals may be delivered simultaneously, sequentially (e.g., delivery of stimulation to the brain precedes delivery of stimulation to the heart or vice versa), or delivery of the first and second signals may be interspersed or interleaved.

The first electrode may be used as a cathode to provide an afferent first electrical signal to modulate the brain of the patient via main trunk electrode 125-1. Electrode 125-1 may generate both afferent and efferent action potentials in vagus nerve 127. One or more of electrodes 125-2 and 125-3 are used as anodes to complete the circuit. Where this is the case, some of the action potentials may be blocked at the anode(s), with the result that the first electrical signal may predominantly modulate the brain by afferent actions traveling toward the brain, but may also modulate one or more other organs by efferent action potentials traveling toward the heart and/or lower organs, to the extent that the efferent action potentials are not blocked by the anode(s).

The second electrode may be used as a cathode to provide an efferent second electrical signal to slow the heart rate of the patient via cardiac branch electrode 125-2. Either first electrode 125-1 or a third electrode 125-3 (or can 121) may be used as an anode to complete the circuit. In one embodiment, the first electrical signal may be applied to the upper (127-1) or lower (127-3) main trunk of the vagus nerve in an open-loop manner according to programmed parameters including an off-time and an on-time. The on-time and off-time together establish the duty cycle determining the fraction of time that the signal generator applies the first electrical. In one embodiment, the off-time may range from 7 seconds to several hours or even longer, and the on-time may range from 5 seconds to 300 seconds. It should be noted that the duty cycle does not indicate when current is flowing through the circuit, which is determined from the on-time together with the pulse frequency (usually 10-200, Hz, and more commonly 20-30 Hz) and pulse width (typically 0.1-0.5 milliseconds). The first electrical signal may also be defined by a current magnitude (e.g., 0.25-3.5 milliamps), and possibly other parameters (e.g., pulse width, and whether or not a current ramp-up and/or ramp-down is provided, a frequency, and a pulse width.

In one embodiment, a seizure detection may result in both applying the first electrical signal to provide stimulation to the brain in close proximity to a seizure detection (which may interrupt or terminate the seizure), as well as application of the second electrical signal which may slow the heart, thus exerting a cardio-protective effect. In a particular embodiment, the second electrical signal is applied only in response to a seizure detection that is characterized by (or accompanied or associated with) an increase in heart rate, and is not applied in response to seizure detections that are not characterized by an increase in heart rate. In this manner, the second electrical signal may help interrupt the seizure by restoring the heart to a pre-seizure baseline heart rate when the patient experiences ictal tachycardia (elevated heart rate during the seizure), while leaving the heart rate unchanged if the seizure has no significant effect on heart rate.

In still further embodiments, additional logical conditions may be established to control when the second electrical signal is applied to lower the patient's heart rate following a seizure detection. In one embodiment, the second electrical signal is applied only if the magnitude of the ictal tachycardia rises above a defined level. In one embodiment, the second electrical signal is applied to the cardiac branch only if the heart rate increases by a threshold amount above the pre-ictal baseline heart rate (e.g., more than 20 beats per minute above the baseline rate). In another embodiment, the second electrical signal is applied to the cardiac branch only if the heart rate exceeds an absolute heart rate threshold (e.g., 100 beats per minute, 120 beats per minute, or other programmable threshold). In a further embodiment, a duration constraint may be added to one or both of the heart rate increase or absolute heart rate thresholds, such as a requirement that the heart rate exceed the baseline rate by 20 beats per minute for more than 10 seconds, or exceed 110 beats per minute for more than 10 seconds, before the second electrical signal is applied to the cardiac branch in response to a seizure detection.

In another embodiment, the heart rate sensor continues to monitor the patient's heart rate during and/or after application of the second electrical signal, and the second electrical signal is interrupted or terminated if the patient's heart rate is reduced below a low heart rate threshold, which may be the baseline heart rate that the patient experienced prior to the seizure, or a rate lower or higher than the baseline pre-ictal heart rate. The low rate threshold may provide a measure of safety to avoid undesired events such as bradycardia and/or syncope.

In yet another embodiment, heart rate sensor 130 may continue to monitor heart rate and/or kinetic sensor 140 may continue to monitor body movement in response to applying the second electrical signal, and the second electrical signal may be modified (e.g., by changing one or more parameters such as pulse frequency, or by interrupting and re-initiating the application of the second electrical signal to the cardiac branch of the vagus nerve) to control the heart rate below an upper heart rate threshold and/or body movement exceeds one or more movement thresholds. For example, the frequency or duration of the second electrical signal applied to the cardiac branch of the vagus nerve may be continuously modified based the instantaneous heart rate as monitored during the course of a seizure to control what would otherwise be an episode of ictal tachycardia below an upper heart rate threshold. In one exemplary embodiment, the second electrical signal may be programmed to provide a 30-second pulse burst at 30 Hz, with the pulses having a pulse width of 0.25 milliseconds and a current of 1.5 milliamps. If, at the end of the 30 second burst, the heart rate remains above 120 beats per minute, and is continuing to rise, the burst may be extended to 1 minute instead of 30 seconds, the frequency may be increased to 50 Hz, the pulse width may be increased to 350 milliseconds, or combinations of the foregoing. In still further embodiments, additional therapies (e.g., oxygen delivery, drug delivery, cooling therapies, etc.) may be provided to the patient if the body data (heart rate, kinetic activity, etc.) indicates that the patient's seizure is not under control or terminated.

Abnormalities or changes in EKG morphology or rhythm relative to an interictal morphology or rhythm may also trigger delivery of current to the heart via the trunks of vagi or its cardiac rami. In other embodiments, pharmacological agents such as beta-blockers may be automatically released into a patient's blood stream in response to the detection of abnormal heart activity during or between seizures.

In one embodiment, the first electrical signal and the second electrical signal are substantially identical. In another embodiment, the first electrical signal may vary from the second electrical signal in terms of one or more of pulse width, number of pulses, amplitude, frequency, inter-pulse-interval, stimulation on-time, and stimulation off-time, among other parameters and degree, rate or type of charge balancing.

The number of pulses applied to the main trunk or cardiac branch, respectively, before changing the polarity of the first and second electrodes need not be one. Thus, two or more pulses may be applied to the main trunk before applying pulses to the cardiac branch of the vagus nerve. More generally, the first and second signals can be independent of one another and applied according to timing and programming parameters controlled by the controller 210 and stimulation unit 220.

In one embodiment, one or more pulse bursts of the first electrical signal are applied to the main trunk of the vagus nerve in response to a detected seizure before applying one or more bursts of the second electrical signal to the cardiac branch. In another embodiment, the first and second signals are interleaved on a pulse-by-pulse basis under the control of the controller 210 and stimulation unit 220.

Typically, VNS can be performed with pulse frequency of 20-30 Hz (resulting in a number of pulses per burst of 140-1800, at a burst duration from 7-60 sec). In one embodiment, at least one of the first electrical signal and the second electrical signal comprises a microburst signal. Microburst neurostimulation is discussed by U.S. Ser. No. 11/693,451, filed Mar. 2, 2007 and published as United States patent Publication No. 20070233193, and incorporated herein by reference in its entirety. In one embodiment, at least one of the first electrical signal, the second electrical signal, and the third electrical signal is characterized by having a number of pulses per microburst from 2 pulses to about 25 pulses, an interpulse interval of about 2 msec to about 50 msec, an interburst period of at least 100 msec, and a microburst duration of less than about 1 sec.

Cranial nerves such as the vagus nerve include different types of nerve fibers, such as A-fibers, B-fibers and C-fibers. The different fiber types propagate action potentials at different velocities. Each nerve fiber is directional—that is, endogenous or natural action potentials can generally propagate action potentials in only one direction (e.g., afferently to the brain or efferently to the heart and/or viscera). That direction is referred to as the orthodromic direction. Exogenous stimulation (e.g., by electrical pulses) may induce action potentials in both the orthodromic direction as well as the antidromic direction. Depending upon the desired effects of stimulation (e.g., afferent modulation of the brain, efferent modulation of the heart, etc.) certain measures (e.g., cooling, pressure, etc.) may be taken to block propagation in either the efferent or the afferent direction. It is believed that the anode may block at least some action potentials traveling to it from the cathode. For example, referring to FIG. 1, both afferent and efferent action potentials may be generated in an upper main trunk of vagus nerve 127-1 by applying a pulse to the nerve using upper main trunk electrode 125-1 as a cathode. Action potentials generated at upper main trunk electrode 125-1 and traveling toward the heart on cardiac branch 127-2 may be blocked by cardiac branch anode 125-2. Action potentials traveling from the upper main trunk 127-1 to the lower organs in lower main trunk 127-3 may be either blocked (by using lower main trunk electrode 125-3 as an anode either with or instead of cardiac branch electrode 125-2) or allowed to travel to the lower organs (by not using electrode structure 125-3 as an electrode).

Action potentials may be generated and allowed to travel to the heart by making the electrode 125-2 the cathode. If cardiac branch electrode 125-2 is used as a cathode, action potentials will reach the heart in large numbers, while action potentials traveling afferently toward the brain may be blocked in the upper trunk if upper electrode 125-1 is made the anode.

In a further embodiment of the disclosure, rapid changes in electrode polarity may be used to generate action potentials to collision block action potentials propagating in the opposite direction. To generalize, in some embodiments, the vagus nerve can be selectively stimulated to propagate action potentials either afferently (i.e., to the brain) or efferently (i.e., to the heart and/or lower organs/viscerae).

Turning now to FIG. 2, a block diagram depiction of an implantable medical device, in accordance with one illustrative embodiment of the present disclosure is illustrated. The IMD 200 may be coupled to various electrodes 125 and/or 127 via lead(s) 122 (FIGS. 1A, 1C). First and second electrical signals used for therapy may be transmitted from the IMD 200 to target areas of the patient's body, specifically to various electrodes associated with the leads 122. Stimulation signals from the IMD 200 may be transmitted via the leads 122 to stimulation electrodes (electrodes that apply the therapeutic electrical signal to the target tissue) associated with the electrode assembly 125, e.g., 125-1, 125-2, 125-3 (FIG. 1A).

The IMD 200 may comprise a controller 210 capable of controlling various aspects of the operation of the IMD 200. The controller 210 is capable of receiving internal data and/or external data and controlling the generation and delivery of a stimulation signal to target tissues of the patient's body. For example, the controller 210 may receive manual instructions from an operator externally, may perform stimulation based on internal calculations and programming, and may receive and/or process sensor data received from one or more body data sensors such as electrodes 125-1, 125-2, 125-3, or heart rate sensor 130. The controller 210 is capable of affecting substantially all functions of the IMD 200.

The controller 210 may comprise various components, such as a processor 215, a memory 217, etc. The processor 215 may comprise one or more micro controllers, microprocessors, etc., that are capable of executing a variety of software components. The processor may receive, pre-condition and/or condition sensor signals, and may control operations of other components of the IMD 200, such as stimulation unit 220, seizure detection module 240, logic unit 250, communication unit, 260, and electrode polarity reversal unit 280. The memory 217 may comprise various memory portions, where a number of types of data (e.g., internal data, external data instructions, software codes, status data, diagnostic data, etc.) may be stored. The memory 217 may store various tables or other database content that could be used by the IMD 200 to implement the override of normal operations. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering a variety of electrical signal therapy signals to one or more electrodes via leads. The stimulation unit 220 is capable of delivering a programmed, first electrical signal to the leads 122 coupled to the IMD 200. The electrical signal may be delivered to the leads 122 by the stimulation unit 220 based upon instructions from the controller 210. The stimulation unit 220 may comprise various types of circuitry, such as stimulation signal generators, impedance control circuitry to control the impedance "seen" by the leads, and other circuitry that receives instructions relating to the type of stimulation to be performed.

Signals from sensors (electrodes that are used to sense one or more body parameters such as temperature, heart rate, brain activity, etc.) may be provided to the IMD 200. The body signal data from the sensors may be used by a seizure detection algorithm embedded or processed in seizure detection module 240 to determine whether or not the patient is having and/or has had an epileptic seizure. The seizure detection algorithm may comprise hardware, software, firmware or combinations thereof, and may operate under the control of the controller 210. Although not shown, additional signal conditioning and filter elements (e.g., amplifiers, D/A converters, etc., may be used to appropriately condition the signal for use by the seizure detection module 240. Sensors such as heart sensor 130 and kinetic sensor 140 may be used to detect seizures, along with other autonomic, neurologic, or other body data.

The IMD 200 may also comprise an electrode polarity reversal unit 280. The electrode polarity reversal unit 280 is capable of reversing the polarity of electrodes (125-1, 125-2, 125-3) associated with the electrode assembly 125. The electrode polarity reversal unit 280 is shown in more detail in FIG. 3. In preferred embodiments, the electrode polarity reversal unit is capable of reversing electrode polarity rapidly, i.e., in about 10 microseconds or less, and in any event at a sufficiently rapid rate to permit electrode polarities to be changed between adjacent pulses in a pulsed electrical signal.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230 may comprise a lithium/thionyl chloride cell or a lithium/carbon monofluoride (LiCFx) cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 comprises a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

In one embodiment, the communication unit 260 can transmit a log of stimulation data and/or seizure detection data to the patient, a physician, or another party.

Figure 1D:
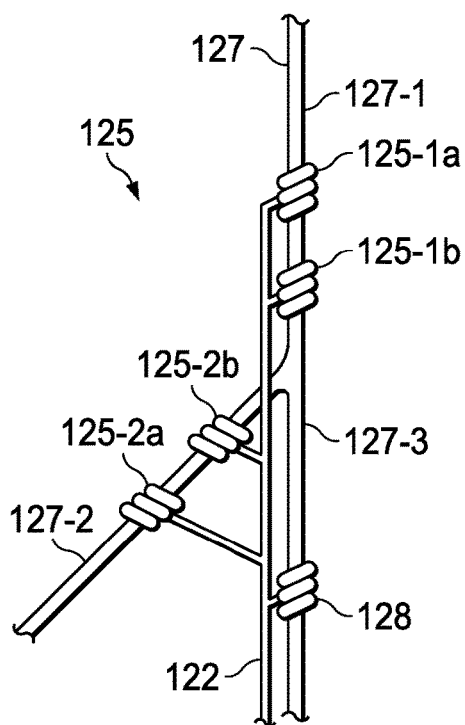
Figure 1E:
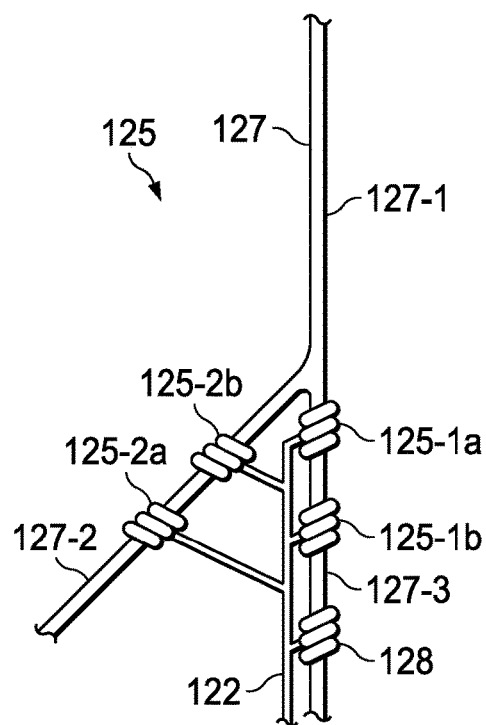

In one embodiment, a method of treating an epileptic seizure is provided that involves providing simultaneously both a first electrical signal to a main trunk of a vagus nerve and a second electrical signal to a cardiac branch of the vagus nerve. As used herein "simultaneously" refers to the on-time of the first and second signals, and does not require that individual pulses of the first signal and the second signal be simultaneously applied to target tissue. The timing of pulses for the first electrical signal and the second electrical signal may be determined by controller 210 in conjunction with stimulation unit 220. Where active charge-balancing is used, it may be possible to use the active charge-balancing phase of pulses of the first electrical signal as the stimulation phase of the second electrical signal by selecting a current magnitude of the cathode in the charge-balancing phase (typically a second electrode, which may be the anode of the initial stimulation phase) that is sufficient to generate action potentials in nerve fibers of the target tissue. Controller 210 may in some embodiments provide simultaneous delivery of first and second electrical signals by interleaving pulses for each of the first and second electrical signals based upon the programmed timing of pulses for each signal and the appropriate polarity of each of first and second electrodes 125-1 and 125-2. In some embodiments, additional electrodes may be used to minimize the induction of action potentials to the heart or the brain provided by the first electrical signal or the second electrical signal. This may be accomplished, in one embodiment, by using an anode located on either the upper main trunk or the cardiac branch to block impulse conduction to the heart or brain from the cathode, or by providing dedicated electrode pairs on both the main trunk and cardiac branches (FIGS. 1D, 1E). When beneficial, steps to avoid collisions of actions potentials travelling in opposite directions may be implemented, while steps to promote collisions may be taken when clinically indicated. In some embodiments, the method further includes sensing a cardiac signal and a kinetic signal of the patient, and detecting a seizure event with a seizure detection algorithm.

In one embodiment, a first electrical signal is applied to a main trunk of a vagus nerve and a second electrical signal is simultaneously applied to a cardiac branch of a vagus nerve. A pulse of the first electrical signal is generated with the electrical signal generator 110 and applied to the main trunk of the vagus nerve using a first electrode (e.g., 125-1, 125-1*a*) as a cathode and a second electrode (e.g., 125-1*b*, 125-3, or 125-2) as an anode. The method includes sensing a cardiac signal and a kinetic signal of the patient, and detecting a seizure event with a seizure detection algorithm. A pulse of the second electrical signal (having the appropriate pulse width and current) is generated and applied (under appropriate timing control by controller 110 and stimulation unit 220) to the cardiac branch of the vagus nerve using a second electrode (e.g., 125-2, 125-2*a*) as a cathode and another electrode (e.g., 125-3, 125-1, 125-2*b*) as an anode. Another pulse of the first electrical signal may thereafter be generated and applied to the main trunk under timing and parameter control of controller 210 and stimulation unit 220. By appropriate selection of cathodes and anodes, the first and second electrical signals may be interleaved and provided simultaneously to the main trunk and cardiac branches of the vagus nerve. In some embodiments, the number of electrodes may be minimized by provided a polarity reversal unit that may rapidly change the polarity of particular electrodes to allow their use in delivering both the first and second signals.

The IMD 200 is capable of delivering stimulation that can be contingent, periodic, random, coded, and/or patterned. The stimulation signals may comprise an electrical stimulation frequency of approximately 0.1 to 10,000 Hz. The stimulation signals may comprise a pulse width in the range of approximately 1-2000 micro-seconds. The stimulation signals may comprise current amplitude in the range of approximately 0.1 mA to 10 mA. Appropriate precautions may be taken to avoid delivering injurious current densities to target neural tissues, e.g., by selecting current, voltage, frequency, pulse width, on-time and off-time parameters to maintain current density below thresholds for damaging tissues.

The IMD 200 may also comprise a magnetic field detection unit 290. The magnetic field detection unit 290 is capable of detecting magnetic and/or electromagnetic fields of a predetermined magnitude. Whether the magnetic field results from a magnet placed proximate to the IMD 200, or whether it results from a substantial magnetic field encompassing an area, the magnetic field detection unit 290 is capable of informing the IMD of the existence of a magnetic field. The changeable electrode polarity stimulation described herein may be activated, deactivated, or alternatively activated or deactivated using a magnetic input.

The magnetic field detection unit 290 may comprise various sensors, such as a Reed Switch circuitry, a Hall Effect sensor circuitry, and/or the like. The magnetic field detection unit 290 may also comprise various registers and/or data transceiver circuits that are capable of sending signals that are indicative of various magnetic fields, the time period of such fields, etc. In this manner, the magnetic field detection unit 290 is capable of detecting whether the detected magnetic field relates to an input to implement a particular first or second electrical signal (or both) for application to the main trunk of cardiac branches, respectively, of the vagus nerve.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, one or more of the circuitry and/or software units associated with the various blocks illustrated in FIG. 2 may be combined into a programmable device, such as a field programmable gate array, an ASIC device, etc.

Figure 3:
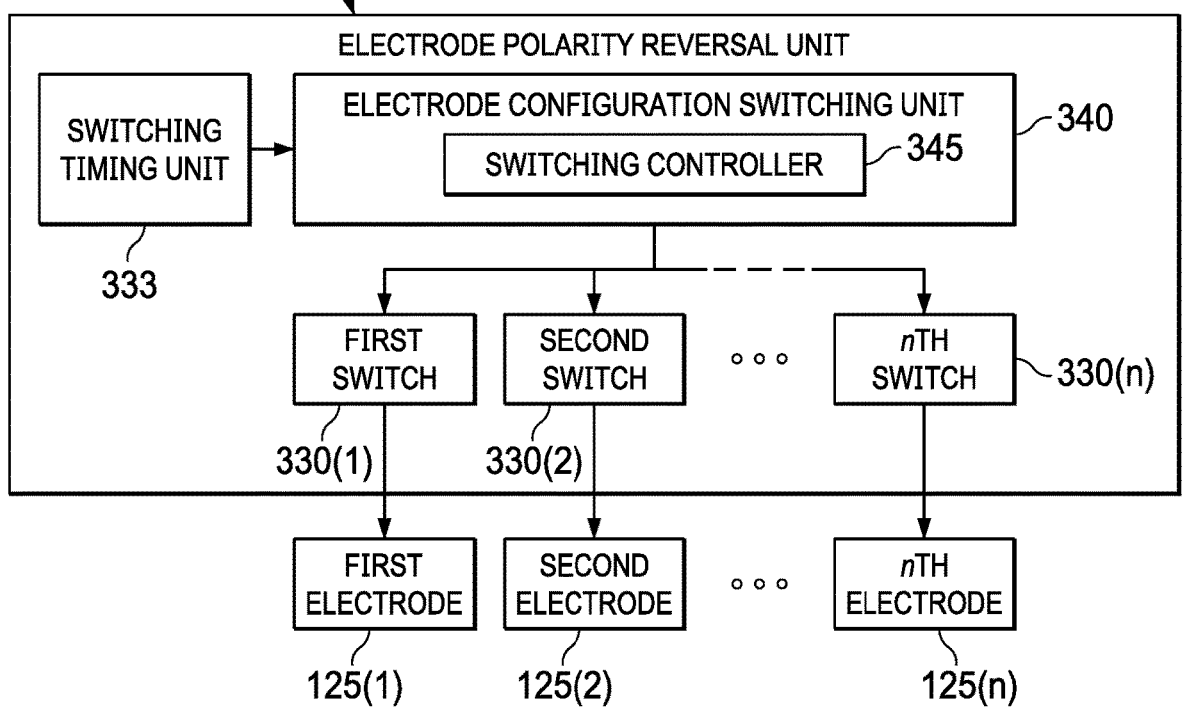
FIG. 3 illustrates a block diagram depiction of an electrode polarity reversal unit shown in FIG. 2, in accordance with one illustrative embodiment of the present disclosure.

FIG. 3 shows in greater detail an electrode polarity reversal unit 280 (FIG. 2) in one embodiment. The electrode polarity reversal unit 280 comprises an electrode configuration switching unit 340, which includes a switching controller 345. The switching controller 345 transmits signals to one or more switches, generically, n switches 330(1), 330(2), . . . **330(*n*) which effect the switching of the configuration of two or more electrodes, generically, n electrodes 125(1), 125(2), . . . 125(*n*). Although FIG. 3 shows equal numbers of switches 330 and electrodes 125, persons of skill in the art having the benefit of the present disclosure will understand that the number of switches 330 and their connections with the various electrodes 125 can be varied as a matter of routine optimization. A switching timing unit 333 can signal to the electrode configuration switching unit 340** that a desired time for switching the electrode configuration has been reached.

Instructions for implementing two or more stimulation regimens, which may include at least one open-loop electrical signal and at least one closed-loop electrical signal, may be stored in the IMD 200. These stimulation signals may include data relating to the type of stimulation signal to be implemented. In one embodiment, an open-loop signal may be applied to generate action potentials for modulating the brain of the patient, and a closed-loop signal may be applied to generate either action potentials for slowing the heart rate of the patient, or both action potentials to modulate the brain of the patient as well as action potentials for slowing the heart rate of the patient. In some embodiments, the open-loop and closed-loop signals may be provided to different target portions of a vagus nerve of the patient by switching the polarity of two or more electrodes using an electrode polarity reversal unit as described in FIG. 3 above. In alternative embodiments, additional electrodes may be provided to generate each of the open-loop and closed-loop signals without electrode switching.

In one embodiment, a first open-loop mode of stimulation may be used to provide an electrical signal to a vagus nerve using a first electrode as a cathode on a main trunk (e.g., 127-1 or 127-3 using electrodes 125-1 or 125-3, respectively) of a vagus nerve, and a second electrode as an anode on either a main trunk (e.g., electrode 125-3, when electrode 125-1 is used as a cathode) or cardiac branch (e.g., electrode 125-2) of a vagus nerve. The first open-loop signal may include a programmed on-time and off-time during which electrical pulses are applied (the on-time) and not-applied (the off-time) in a repeating sequence to the vagus nerve.

A second, closed-loop signal may be provided in response to a detected event (such as an epileptic seizure, particularly when accompanied by an increase in the patient's heart rate) using a different electrode configuration than the first, open-loop signal. In one embodiment, the second, closed-loop signal is applied to a cardiac branch using the second electrode 125-2 as a cathode and the first electrode on the main trunk (e.g., 125-1 or 125-3) as an anode. The second, closed-loop signal may involve generating efferent action potentials on the cardiac branch of the vagus nerve to slow the heart rate. In some embodiments, the first, open-loop signal may be interrupted/suspended in response to the detected event, and only the second, closed-loop signal is applied to the nerve. In other embodiments, the first, open loop signal may not be interrupted when the event is detected, and both the first, open-loop signal and the second, closed-loop signal are applied to the vagus nerve. In another embodiment, a third, closed-loop signal may also be provided in response to the detected event. The third, closed-loop signal may involve an electrical signal using the same electrode configuration as the first, open-loop electrical signal, but may provide a different electrical signal to the main trunk of the vagus nerve than either the first, open-loop signal or the second, closed-loop signal. The first, open-loop signal may be interrupted, terminated or suspended in response to the detected event, and the third, closed-loop signal may be applied to the nerve either alone or with the second, closed-loop signal. In some embodiments, both the second and third closed-loop signals may be provided in response to a detected epileptic seizure by rapidly changing the polarity of the first (125-1) and second (125-2) electrodes from cathode to anode and back, as pulses are provided as part of the second and third electrical signals, respectively. In one embodiment, the third electrical signal may involve modulating the brain by using a main trunk electrode (e.g., upper main trunk electrode 125-1) as a cathode and another electrode (e.g., cardiac branch electrode 125-2 or lower main trunk electrode 125-3) as an anode. The third electrical signal may comprise, for example, a signal that is similar to the first electrical signal but which provides a higher electrical current than the first electrical signal, and for a longer duration than the first signal or for a duration that is adaptively determined based upon a sensed body signal (in contrast, for example, to a fixed duration of the first electrical signal determined by a programmed on-time). By rapidly changing polarity of the electrodes, pulses for each of the second and third electrical signals may be provided such that the second and third signals are provided simultaneously to the cardiac branch and main trunk of the vagus nerve. In other embodiments, the first, second and third electrical signals may be provided sequentially rather than simultaneously.

In some embodiments, one or more of the first, second and third electrical signals may comprise a microburst signal, as described more fully in U.S. patent application Ser. Nos. 11/693,421, 11/693,451, and 11/693,499, each filed Mar. 29, 2007 and each hereby incorporated by reference herein in their entirety.

In one embodiment, each of a plurality of stimulation regimens may respectively relate to a particular disorder, or to particular events characterizing the disorder. For example, different electrical signals may be provided to one or both of the main trunk and cardiac branches of the vagus nerve depending upon what effects accompany the seizure. In a particular embodiment, a first open-loop signal may be provided to the patient in the absence of a seizure detection, while a second, closed-loop signal may be provided when a seizure is detected based on a first type of body movement of the patient as detected by, e.g., an accelerometer, a third, closed-loop signal may be provided when the seizure is characterized by a second type of body movement, a fourth, closed-loop signal may be provided when the seizure is characterized by an increase in heart rate, a fifth, closed-loop signal may be provided when the seizure is characterized by a decrease in heart rate, and so on. More generally, stimulation of particular branches or main trunk targets of a vagus nerve may be provided based upon different body signals of the patient. In some embodiments, additional therapies may be provided based on different events that accompany the seizure, e.g., stimulation of a trigeminal nerve or providing a drug therapy to the patient through a drug pump. In one embodiment, different regimens relating to the same disorder may be implemented to accommodate improvements or regressions in the patient's present condition relative to his or her condition at previous times. By providing flexibility in electrode configurations nearly instantaneously, the present disclosure greatly expands the range of adjustments that may be made to respond to changes in the patient's underlying medical condition.

The switching controller 345 may be a processor that is capable of receiving data relating to the stimulation regimens. In an alternative embodiment, the switching controller may be a software or a firmware module. Based upon the particulars of the stimulation regimens, the switching timing unit 333 may provide timing data to the switching controller 345. The first through nth switches **330(1-*n*)** may be electrical devices, electro-mechanical devices, and/or solid state devices (e.g., transistors).

Figure 4:
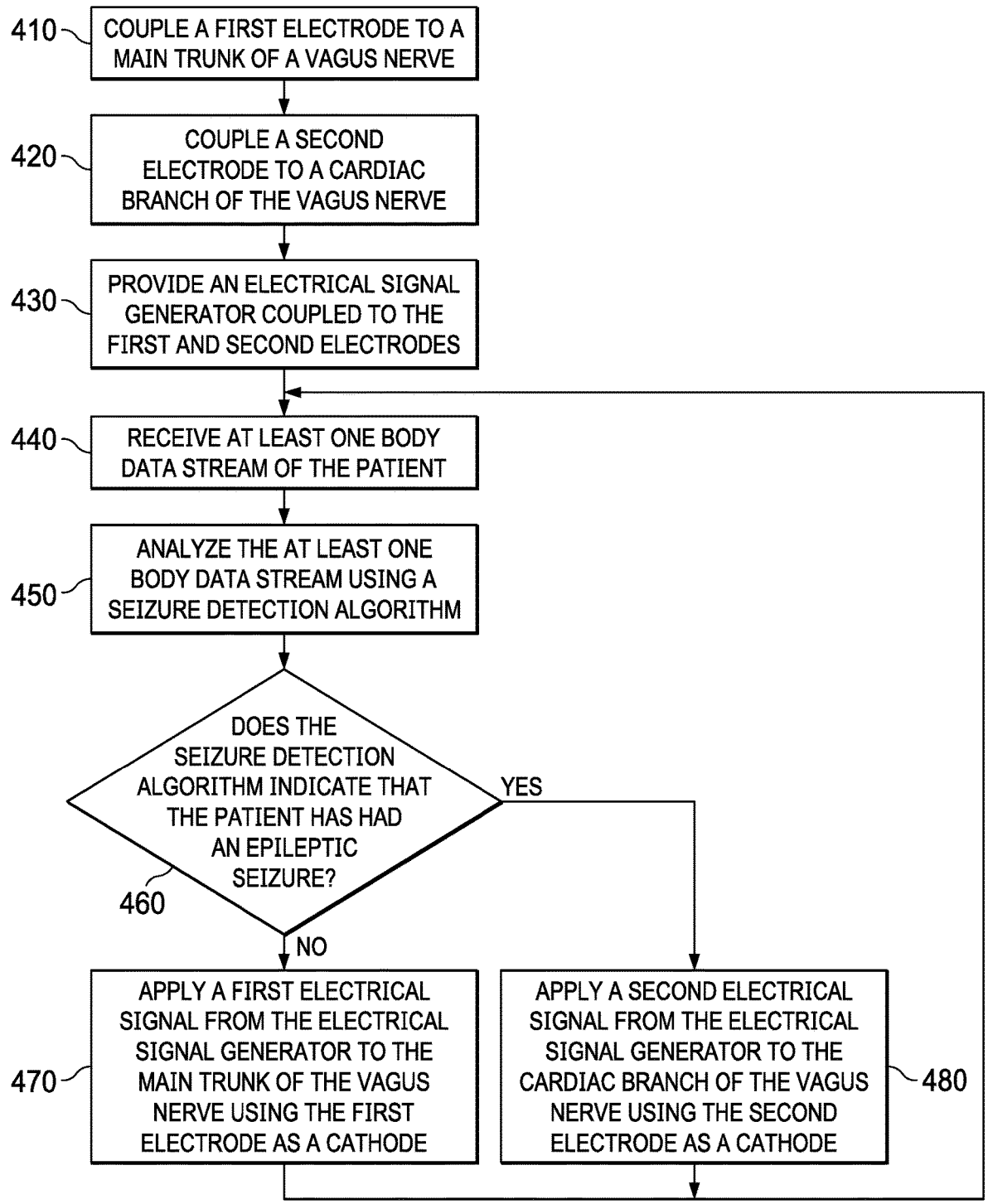
FIG. 4 illustrates a flowchart depiction of a method for providing first and second electrical signals to a main trunk and a cardiac branch of a vagus nerve, respectively, based upon whether or not the patient is having and/or has had an epileptic seizure, in accordance with an illustrative embodiment of the present disclosure.

FIG. 4 shows one embodiment of a method of treating a patient having epilepsy according to the present disclosure. In this embodiment, a first electrode is coupled to a main trunk of a vagus nerve of the patient (410) and a second electrode is coupled to a cardiac branch of the vagus nerve (420). An electrical signal generator is coupled to the first and second electrodes (430).

The method further involves receiving at least one body data stream of the patient (440). The data may be sensed by a sensor such as heart rate sensor 130 (FIG. 1A) or a sensor that is an integral part of, or coupled to, an IMD 200 (FIG. 2) such as electrical pulse generator 110 (FIG. 1A), and the IMD may also receive the data from the sensor. The at least one body data stream is then analyzed using a seizure detection algorithm (450), and the seizure detection algorithm determines whether or not the patient is having and/or has had an epileptic seizure (460).

If the algorithm indicates that the patient is not having and/or has not had an epileptic seizure, the method comprises applying a first electrical signal from the electrical signal generator to the main trunk of a vagus nerve using the first electrode as a cathode (470). In one embodiment, applying the first electrical signal comprises continuing to apply a programmed, open-loop electrical signal periodically to the main trunk of the vagus nerve according a programmed on-time and off-time.

If the algorithm indicates that the patient is having and/or has had an epileptic seizure, the method comprises applying a second electrical signal from the electrical signal generator to the cardiac branch of the vagus nerve using the second electrode as a cathode (480). Depending upon which electrical signal (first or second) is applied, the method may involve changing the polarity of one or both of the first electrode and the second electrode. In one embodiment, the method may comprise suspending the first electrical and applying the second electrical signal. In one embodiment, the method comprises continuing to receive at least one body data stream of the patient at 440 after determining whether or not the patient is having and/or has had an epileptic seizure.

In an alternative embodiment, if the seizure detection algorithm indicates that the patient is having and/or has had an epileptic seizure, both the first electrical signal and the second electrical signal are applied to the main trunk and cardiac branches of a vagus nerve of the patient, respectively, at step 480. In a specific implementation of the alternative embodiment, pulses of the first and second electrical signal are applied to the main trunk and cardiac branch of the vagus nerve under the control of controller 210 by rapidly changing the polarity of the first and second electrodes using the electrode polarity reversal unit 280 to apply the first electrical signal to the main trunk using the first electrode as a cathode and the second electrode as an anode, changing the polarity of the first and second electrodes, and applying the second electrical signal to the cardiac branch using the second electrode as a cathode and the first electrode as an anode. Additional pulses for each signal may be similarly applied by rapidly changing the polarity of the electrodes.

In some embodiments, the first electrical signal and the second electrical signal are applied unilaterally, i.e., to a vagal main trunk and a cardiac branch on the same side of the body. In other embodiments, the first and second electrical signals are applied bilaterally, i.e., the second electrical signal is applied to a cardiac branch on the opposite side of the body from the main vagal trunk to which the first electrical signal is applied. In one embodiment, the first electrical signal is applied to a left main trunk to minimize cardiac effects of the first electrical signal, and the second electrical signal is applied to a right cardiac branch, which modulates the sinoatrial node of the heart to maximize cardiac effects of the second electrical signal.

In alternative embodiments, both the first electrode and the second electrode may be coupled to a cardiac branch of a vagus nerve, with the first electrode (e.g., anode) being proximal to the brain relative to the second electrode, and the second electrode (e.g., cathode) being proximal to the heart relative to the first electrode.

Figure 5:
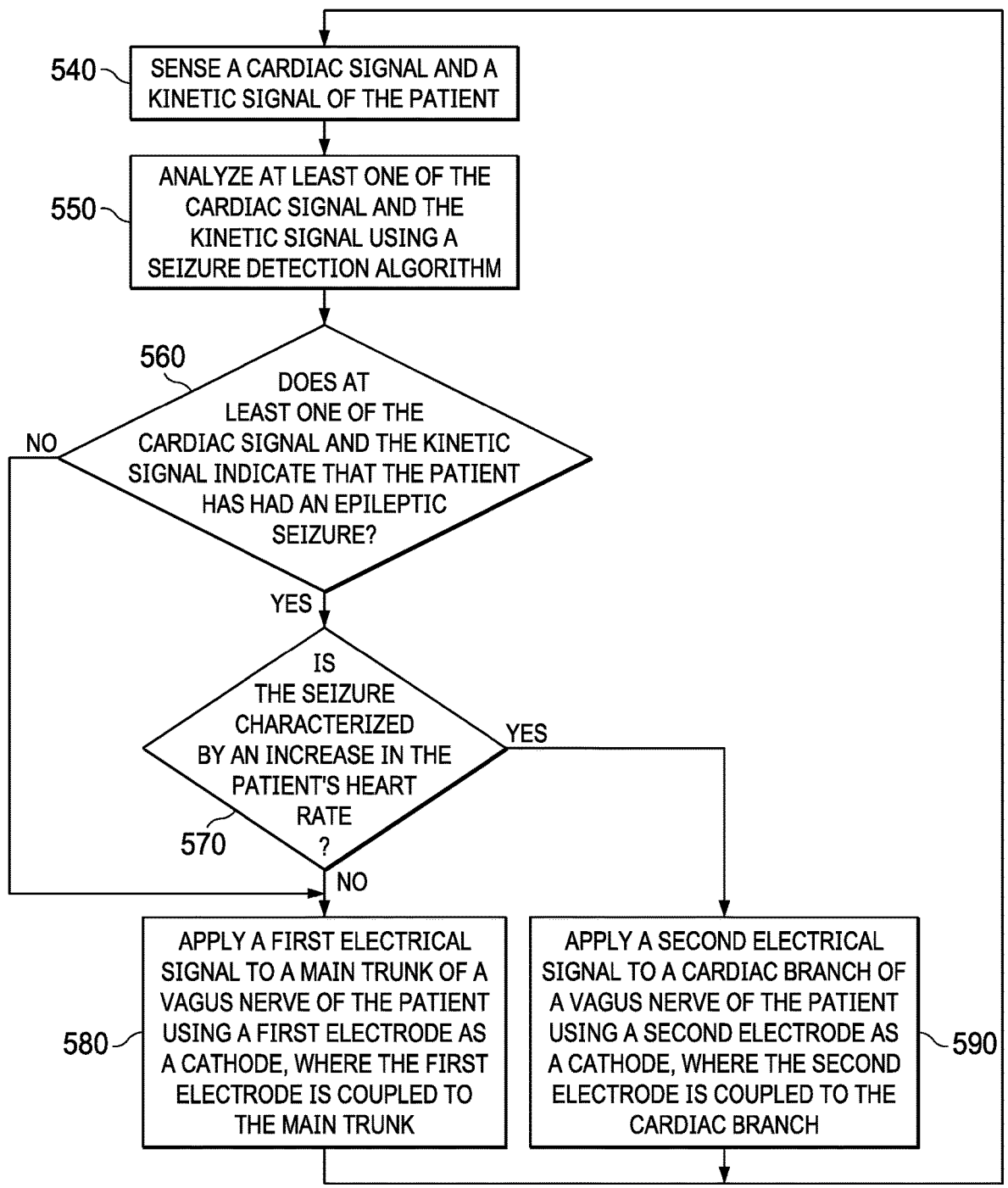
FIG. 5 illustrates a flowchart depiction of a method for providing first and second electrical signals to a main trunk and a cardiac branch of a vagus nerve, respectively, based upon whether or not at least one of a cardiac signal and a kinetic signal indicates that the patient is having and/or has had an epileptic seizure, and whether the seizure is characterized by an increase in heart rate, in accordance with an illustrative embodiment of the present disclosure.

FIG. 5 is a flow diagram of another method of treating a patient having epilepsy according to the present disclosure. A sensor is used to sense a cardiac signal and a kinetic signal of the patient (540). In a particular embodiment, the cardiac sensor may comprise an electrode pair for sensing an ECG (electrocardiogram) or heart beat signal, and the kinetic signal may comprise a triaxial accelerometer to detect motion of at least a portion of the patient's body. The method further comprises analyzing at least one of the cardiac signal and the kinetic signal using seizure detection algorithm (550), and the output of the algorithm is used to determine whether at least one of the cardiac signal and the kinetic signal indicate that the patient is having and/or has had an epileptic seizure (560).

If the patient is not having and/or has not had an epileptic seizure, the method comprises applying a first electrical signal to a main trunk of a vagus nerve of the patient using a first electrode, coupled to the main trunk, as a cathode (580). In one embodiment, the first electrical signal is an open-loop electrical signal having an on-time and off-time.

If the patient is having and/or has had an epileptic seizure, a determination is made whether the seizure is characterized by an increase in the patient's heart rate (570). If the seizure is not characterized by an increase in the patient's heart rate, the method comprises applying the first electrical signal to the main trunk of a vagus nerve using the first electrode as a cathode (580). In one embodiment, the cathode comprises an upper main trunk electrode 125-1 and the anode is selected from a cardiac branch electrode 125-2 and a lower main trunk electrode 125-3. Conversely, if the seizure is characterized by an increase in the patient's heart rate, the method comprises applying a second electrical signal to a cardiac branch of a vagus nerve of the patient using a second electrode, coupled to the cardiac branch, as a cathode (590). The anode is an upper main trunk electrode 125-1 or a lower main trunk electrode 125-3. In one embodiment, the method may comprise suspending the first electrical and applying the second electrical signal.

The method then continues the sensing of the cardiac and kinetic signals of the patient (540) and resumes the method as outlined in FIG. 5.

Figure 6:
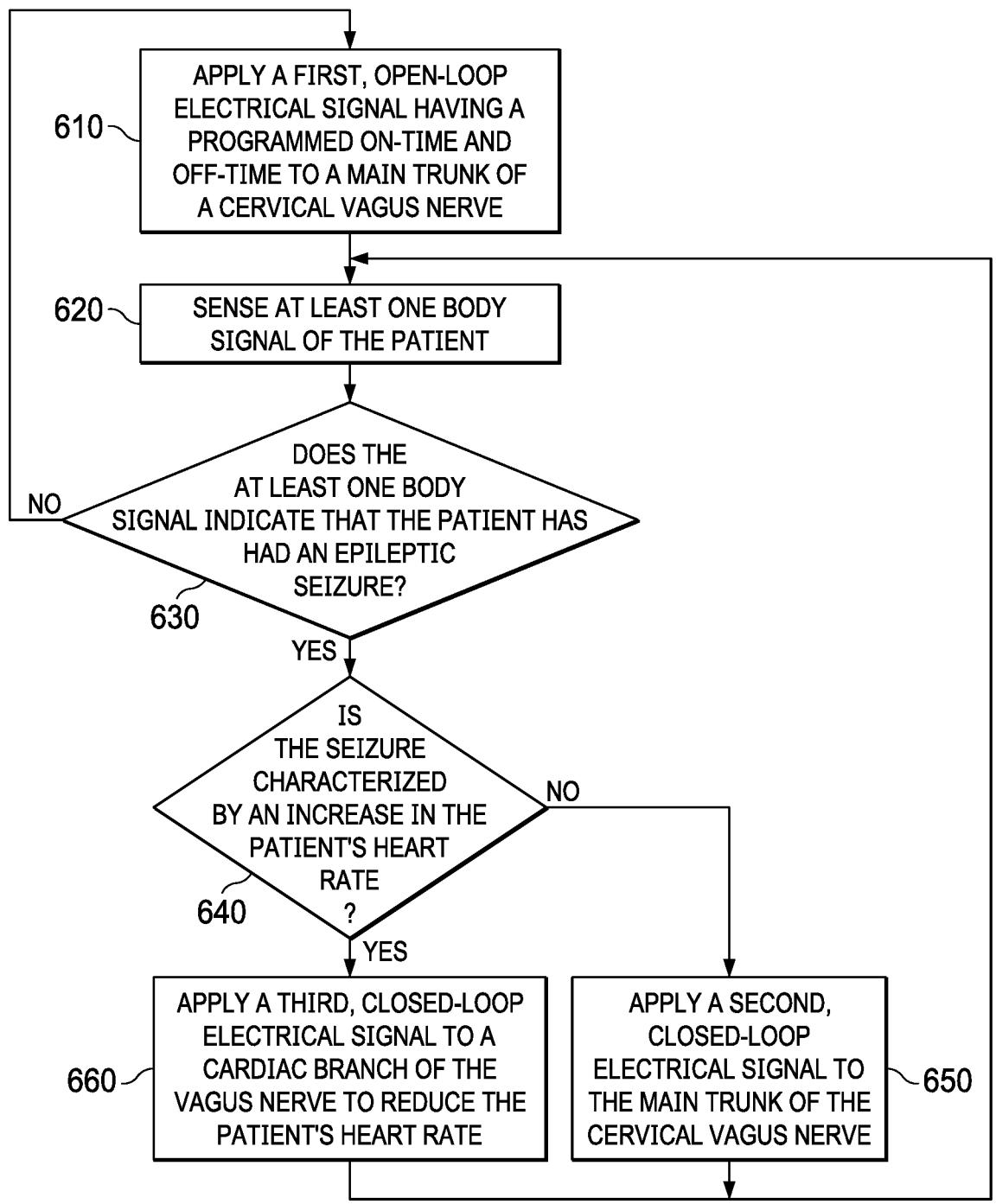
FIG. 6 illustrates a flowchart depiction of a method for providing a first, open-loop electrical signal to a main trunk of a vagus nerve, a second, closed-loop electrical signal to the main trunk of the vagus nerve based upon the patient having had an epileptic seizure not characterized by an increase in heart rate, and a third, closed-loop electrical signal to a cardiac branch of a vagus nerve based upon the patient having had an epileptic seizure characterized by an increase in heart rate, in accordance with an illustrative embodiment of the present disclosure.

FIG. 6 is a flow diagram of a further method of treating a patient having epilepsy according to the present disclosure. The method includes applying a first, open-loop electrical signal to a main trunk of a vagus nerve (610). The open-loop signal is characterized by an off-time in which electrical pulses are applied to the nerve, and an off-time in which electrical pulses are not applied to the nerve.

A sensor is used to sense at least one body signal of the patient (620), and a determination is made whether the at least one body signal indicates that the patient is having and/or has had an epileptic seizure (630). If the patient is not having and/or has not had a seizure, the method continues applying the first, open-loop electrical signal to a main trunk of a vagus nerve (610). If the patient is having and/or has had an epileptic seizure, a determination is made whether the seizure is characterized by an increase in the patient's heart rate (640). In one embodiment, the increase in heart rate is measured from a baseline heart rate existing prior to the seizure, e.g., a median heart rate for a prior period such as the 300 beats prior to the detection of the seizure event, or the 5 minutes prior to the detection of the seizure.

If the seizure is not characterized by an increase in the patient's heart rate, the method comprises applying a second, closed-loop electrical signal to the main trunk of the vagus nerve 650). In one embodiment, the second, closed-loop electrical signal is the same signal as the open-loop electrical signal, except that the second signal (as defined, e.g., by a current intensity, a pulse frequency, a pulse width and an on-time) is applied at a time different from the programmed timing of the first electrical signal. For example, if the first electrical signal comprises an on-time of 30 seconds and an off-time of 5 minutes, but a seizure is detected 1 minute after the end of a programmed on-time, the second electrical signal may comprise applying a 30 second pulse burst at the same current intensity, frequency, and pulse width as the first signal, but four minutes earlier than would have occurred absent the detected seizure. In another embodiment, the second, closed-loop electrical signal is a different signal than the first, open-loop electrical signal, and the method may also comprise suspending the first electrical before applying the second electrical signal. For example, the second, closed-loop electrical signal may comprise a higher current intensity, frequency, pulse width and/or on-time than the first, open-loop electrical signal, and may not comprise an off-time (e.g., the second electrical signal may be applied for a predetermined duration independent of the on-time of the first, open-loop electrical signal, such as a fixed duration of 1 minute, or may continue for as long as the body signal indicates the presence of the seizure event).

Returning to FIG. 6, if the seizure is characterized by an increase in the patient's heart rate, the method comprises applying a third, closed-loop electrical signal to a cardiac branch of a vagus nerve to reduce the patient's heart rate (660). The method may comprise suspending the first electrical as well as applying the third, closed-loop electrical signal. In one embodiment of the disclosure, each of the first, open-loop electrical signal, the second, closed-loop electrical signal, and the third, closed-loop electrical signal are applied unilaterally (i.e., to vagus nerve structures on the same side of the body) to the main trunk and cardiac branch of the vagus nerve. For example, the first, open-loop electrical signal and the second, closed-loop electrical signal may be applied to a left main trunk of the patient's cervical vagus nerve, and the third, closed-loop electrical signal may be applied to the left cardiac branch of the vagus nerve. Similarly, the first, second and third electrical signals may all be applied to the right vagus nerve of the patient. In alternative embodiments, one or more of the first, second and third electrical signals may be applied bilaterally, i.e., one of the first, second and third electrical signals is applied to a vagal structure on the opposite side of the body from the other two signals. For example, in a particular embodiment the first, open-loop signal and the second, closed-loop signal may be applied to a left main trunk of the patient's cervical vagus nerve, and the third, closed-loop electrical signal may be applied to a right cardiac branch of the patient's vagus nerve. Because the right cardiac branch modulates the sinoatrial node of the patient's heart, which is the heart's "natural pacemaker," the third electrical signal may have more pronounced effect in reducing the patient's heart rate if applied to the right cardiac branch.

After applying one of the second (650) and third (660) electrical signals to a vagus nerve of the patient, the method then continues sensing at least one body signal of the patient (620) and resumes the method as outlined in FIG. 6.

In the methods depicted in FIGS. 4-6, one or more of the parameters defining the first, second, and third electrical signals (e.g., number of pulses, pulse frequency, pulse width, On time, Off time, interpulse interval, number of pulses per burst, or interburst interval, among others) can be changed by a healthcare provided using a programmer 150.

Figure 7:
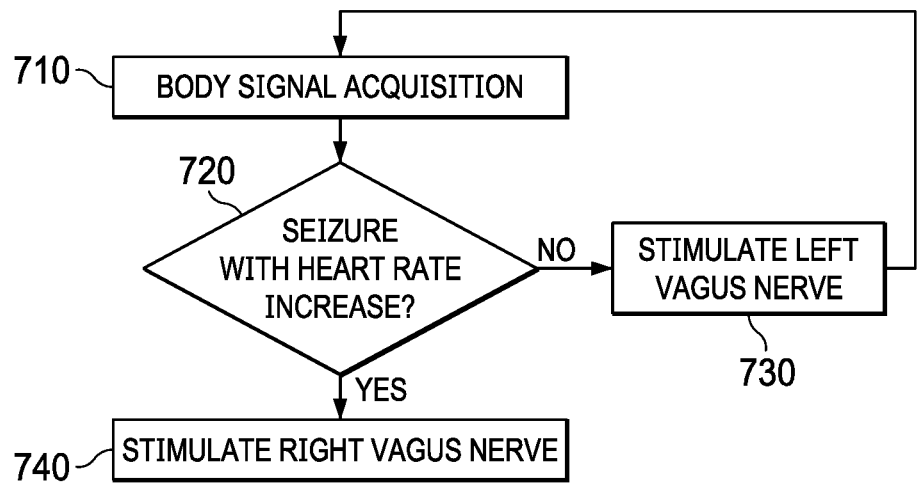
FIG. 7 is a flowchart depiction of a method for providing closed-loop vagus nerve stimulation for a patient with epilepsy by stimulating a right vagus nerve in response to detecting a seizure with tachycardia and stimulating a left vagus nerve in the absence of such a detection. For example if a recumbent person's heart rate is 55 bpm and it increases to 85 during a seizure, this is not clinical/pathological tachycardia, but may be considered tachycardia within the meaning of some embodiments of the present disclosure.

FIG. 7 is a flow diagram of a method of treating patients having seizures accompanied by increased heart rate. In one embodiment, tachycardia is defined as a neurogenic increase in heart rate, that is, an elevation in heart rate that occurs in the absence of motor activity or that if associated with motor activity, the magnitude of the increase in heart rate is larger than that caused by motor activity alone. In one embodiment, a body signal is acquired (710). The body signal may comprise one or more body signals that may be altered, changed or influenced by an epileptic seizure. As non-limiting examples, the body signal may comprise one or more of a cardiac signal such as heart rate, heart rate variability, or EKG complex morphology, a kinetic signal such as an accelerometer signal, a postural signal or body position signal), blood pressure, blood oxygen concentration, skin resistivity or conductivity, pupil dilation, eye movement, EEG, reaction time or other body signals. The body signal may be a real-time signal or a stored signal for delayed or later analysis. It may be acquired, for example, from a sensor element (e.g., coupled to a processor), from a storage device in which the signal data is stored.

The method further comprises determining whether or not the patient is having and/or has had a seizure accompanied by an increase in heart rate (720). In one embodiment, the method comprises a seizure detection algorithm that analyzes the acquired body signal data and determines whether or not a seizure has occurred. In a particular embodiment, the method comprises an algorithm that analyzes one or more of a cardiac signal, a kinetic signal, a cognitive signal, blood pressure, blood oxygen concentration, skin resistivity or conductivity, pupil dilation, and eye movement to identify changes in the one or more signals that indicate a seizure has occurred. The method may comprise an output signal or data flag that may be asserted or set when the detection algorithm determines from the body signal(s) that the patient is having and/or has had a seizure.

The method also comprises determining (720) whether or not the seizure is accompanied by an increase in heart rate. In one embodiment, the body data signal comprises a heartbeat signal that may be analyzed to determine heart rate. In some embodiments, the heart beat signal may be used by the seizure detection algorithm to determine whether a seizure has occurred, while in other embodiments seizures are not detected using heart rate. Regardless of how the seizure is detected, however, the method of FIG. 7 comprises determining whether a detected seizure event is accompanied by an increase in heart rate. The increase may be determined in a variety of ways, such as by an increase in an instantaneous heart rate above a reference heart rate (which may be a predetermined interictal value such as 72 beats per minute (bpm), or a real-time measure of central tendency for a time window, such as a 5 minute median or moving average heart rate). Additional details about identifying increases in heart rate in the context of epileptic seizures are provided in U.S. Pat. Nos. 5,928,272, 6,341,236, 6,587,727, 6,671,556, 6,961,618, 6,920,357, 7,457,665, as well as U.S. patent application Ser. Nos. 12/770,562, 12/771,727, 12/771,783, 12/884,051, 12/886,419, 12/896,525, 13/098,262, and 13/288,886, each of which is hereby incorporated by reference in its entirety herein.

If the body data signal does not indicate that the patient is having and/or has had a seizure accompanied by tachycardia, the method comprises applying a first electrical signal to a left vagus nerve. If the body signal does indicate that the patient has experienced a seizure accompanied by tachycardia, the method comprises applying a second electrical signal to a right vagus nerve.

Without being bound by theory, it is believed that stimulation of the right vagus nerve, which enervates the right sinoatrial nerve that functions as the heart's natural pacemaker, will have a more prominent effect in slowing the heart rate than stimulation of the left vagus nerve. The present disclosure takes advantage of this electrical asymmetry of the left and right vagus nerves to minimize the effect of VNS on heart rate except where there is a need for acute intervention to slow the heart rate, i.e., when the patient has experienced and epileptic seizure, and the seizure is accompanied by an increase in heart rate. This may result in, for example, stimulation of the left vagus nerve either when there is no seizure (such as when an open-loop stimulation program off-time has elapsed and the program initiates stimulation in accordance with a programmed signal on-time), or when there is a detected seizure event that is not accompanied by an increase in heart rate (such as absence seizures); and stimulation of the right vagus nerve when there is a detected seizure event accompanied by a heart rate increase. In one embodiment, a programmed, open-loop electrical signal is applied to the left vagus nerve except when an algorithm analyzing the acquired body signal detects a seizure accompanied by a heart rate increase. In response to such a detection, a closed-loop electrical signal is applied to the right vagus nerve to slow the patient's (increased) heart rate. In some embodiments, the response to detecting a seizure accompanied by a heart rate increase may also include interrupting the application of the programmed-open-loop electrical signal to the left vagus nerve. The interrupted open-loop stimulation of the left vagus nerve may be resumed either when the seizure ends or the heart rate returns to a desired, lower heart rate.

In an additional embodiment of the disclosure, electrode pairs may be applied to each of the left and right vagus nerves of the patient, and used depending upon whether or not seizures accompanied by cardiac changes such as tachycardia are detected.

Figure 8:
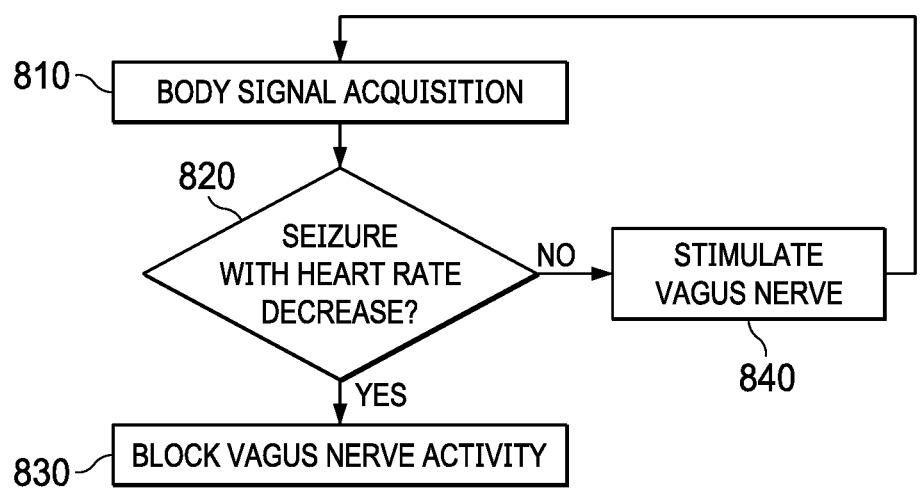
FIG. 8 is a flowchart depiction of a method for providing a closed-loop therapy to a vagus nerve of a patient with epilepsy in response to detecting a seizure associated with a heart rate decrease, wherein said therapy blocks impulse conduction along at least one vagus nerve.

FIG. 8 is a flowchart depiction of a method of treating patients having seizures accompanied by a relative or absolute decrease in heart rate (i.e., a bradycardia episode). Epileptic seizures originating from certain brain regions may trigger decreases in heart rate of a magnitude sufficient to cause loss of consciousness and of postural tone (i.e., syncope). In some subjects the cerebral ischemia associated with the bradycardia may in turn lead to convulsions (i.e., convulsive syncope). If bradycardia-inducing seizures are not controllable by medications, the current treatment is implantation of a demand cardiac pacemaker. In one embodiment of the present disclosure, ictal bradycardia may be treated by preventing vagal nerve impulses from reaching the heart, either by preventing impulses traveling through all fiber types contained in the trunk of the nerve or in one of its branches, or by only blocking impulses within a certain fiber type. In another embodiment, the degree of the nerve impulse blocking within a vagus nerve may be determined based upon the magnitude of bradycardia (e.g., the larger the bradycardia change from the pre-existing baseline heart rate, the larger the magnitude of the block) so as to prevent tachycardia from occurring.

In one embodiment, a body signal is acquired (810). The body signal may comprise one or more body signals that may be altered, changed or influenced by an epileptic seizure. Changes in the body signal may be used to detect the onset or impending onset of seizures. As noted with reference to FIG. 7, the body signal may comprise one or more measure derived from a cardiac signal (e.g., heart rate, heart rate variability, change in EKG morphology), a kinetic signal (e.g., an accelerometer, force of muscle contraction, posture or body position signal), blood pressure, blood oxygen concentration, skin resistivity/conductivity, pupil dilation, eye movement, or other body signals. The body signal may be a real-time signal, a near-real-time signal, or a non-real-time signal, although in preferred embodiments, the signal is a real-time signal or a near-real-time signal. The signal may be acquired from a sensor element (e.g., coupled to a processor) or from a storage device.

Referring again to FIG. 8, the method further comprises determining whether or not the patient is having and/or has had a seizure that is accompanied by a decrease in heart rate (820). In one embodiment, the method comprises using a seizure detection algorithm using one or more of a cardiac, kinetic, neurologic, endocrine, metabolic or tissue stress marker to detect seizures, and to determine if the seizure is associated with a decrease in heart rate. In a particular embodiment, an algorithm—which may comprise software and/or firmware running in a processor in a medical device—analyzes one or more of a cardiac signal, a kinetic signal, blood pressure, blood oxygen concentration, skin resistivity or conductivity, pupil dilation, and eye movement to identify changes in the one or more signals that indicate the occurrence of an epileptic seizure. Such changes may be identified by determining one or more indices from the foregoing signals, such as a cardiac index (e.g., a heart rate), a kinetic index (e.g., a kinetic level or motion type, a magnitude of an acceleration or force, or other indices that may be calculated from an accelerometer signal). The method may include providing an output signal or setting a data flag when the detection algorithm determines from the body signal(s) that the patient is having and/or has had a seizure. In a preferred embodiment, the seizure detection occurs in real time and the output signal or data flag is set immediately upon detection of the seizure.

Once it is determined that the patient is having and/or has had a seizure, the method also comprises determining if the seizure is accompanied by a decrease in heart rate. In one embodiment, the acquired body data signal (810) comprises a heartbeat signal that may be analyzed to determine heart rate. In some embodiments, the acquired heart beat signal may be used by the seizure detection algorithm to determine whether a seizure has occurred, while in other embodiments seizures are determined without regard to the patient's heart rate. Regardless of how the seizure is determined, the method of FIG. 8 comprises determining whether a detected seizure event is accompanied by a decrease in heart rate (820). The decrease in heart rate may be determined in a variety of ways, such as by a decrease in an instantaneous heart rate below a reference heart rate value (which may be a predetermined interictal value such as 72 beats per minute (bpm), or a real-time measure of central tendency for a time window or number-of-beats window (e.g., a 5 minute median or moving average heart rate, or a media heart rate for a window selected from 3-300 beats such as a 5, 10, or 300 beat window)). Additional details about identifying decreases in heart rate in the context of epileptic seizures are provided in U.S. patent application Ser. Nos. 12/770,562, 12/771,727, 12/771,783, 12/884,051, 12/886,419, 13/091,033, each of which is hereby incorporated by reference in its entirety herein.

In one embodiment, if the acquired body data signal does not indicate that the patient is having and/or has had a seizure accompanied by a HR decrease, the method comprises applying a first electrical signal to a vagus nerve (840), wherein the first electrical signal is sufficient to generate exogenous action potentials in fibers of the vagus nerve. The second electrical signal is a therapeutic electrical signal to treat the seizure. It may be applied to either the left or right vagus nerves, or both. The first electrical signal may be a signal defined by, among other parameters, an on-time during which electrical pulses are applied to the nerve, and an off-time during which no pulses are applied to the nerve. In some embodiments, the on-time may be determined by the duration and intensity of the change in heart rate, while in other embodiments it may be pre-programmed Cathode(s) and anode(s) may be placed on the nerve trunks or branches to maximize flow of exogenously generated nerve impulses in a caudal direction (for control of heart rate changes) and a cephalic direction for seizure treatment.

If the body signal indicates that the patient is having and/or has had a seizure accompanied by a decrease in heart rate, the method comprises applying an action to decrease vagal/parasympathetic tone. In one embodiment, the method comprises blocking the passage of impulses through at least one of a vagus nerve trunk or branch. This may be accomplished by applying one or more of a second electrical signal (e.g., a high frequency electrical signal), a thermal signal (e.g., cooling), a chemical signal (e.g., applying a local anesthetic), and/or a mechanical signal (e.g., applying pressure or a vibration) to a vagus nerve of the patient (830). In another embodiment, the method comprises delivering at least one of an anti-cholinergic drug or a sympatho-mimetic drug.

As used herein, blocking vagus nerve activity means blocking intrinsic or native vagal activity (i.e., blocking action potentials not artificially or exogenously induced by an electrical signal generated by a device). The blocking signal may block the conduction of action potentials in all or at least some portion or fraction of the axons of a vagus nerve. In general, such blocking signals are incapable of inducing exogenous action potentials in the axons of the vagus nerve. In one embodiment, the blocking signal may comprise a high frequency, pulsed electrical signal, the pulse frequency being sufficient to inhibit propagation of at least some action potentials in vagus nerve fibers. The electrical signal may comprise a signal in excess of 300 Hz, or other frequency, so long as the frequency and other stimulation signal parameters (such as pulse width and pulse current or voltage) provide a signal capable of inhibiting some or all of the action potentials propagating along fibers of the vagus nerve. In alternative embodiments, the electrical signal may comprise generating unidirectional action potentials for collision blocking of endogenous action potentials.

High frequency vagus nerve stimulation (or other blocking signals such as collision blocking) may inhibit pathological vagus nerve activity associated with the seizure that may be acting to slow the patient's heart rate. By providing such stimulation only when the patient experiences a seizure accompanied by a reduced heart rate (e.g., bradycardia), a therapy may be provided that acts to maintain the patient's heart rate when the patient experiences a seizure involving excessive vagal activity—and consequent undesired slowing of—the heart. In one embodiment, the blocking electrical signal (830) is provided to a right vagus nerve. Without being bound by theory, because the right vagus nerve innervates the right sinoatrial node that functions as the heart's natural pacemaker, it is believed that right-side VNS will have a more significant effect upon the heart rate than stimulation of the left vagus nerve. In alternative embodiments, the blocking signal may be applied to the left vagus nerve, to both the right and left vagus nerves, or to one or both of the left and right cardiac branches of the vagus nerves.

In one embodiment, the method comprises applying a first electrical signal that may be a conventional vagus nerve stimulation signal defined by a plurality of parameters (e.g., a pulse width, a current magnitude, a pulse frequency, an on-time and an off-time). A seizure detection algorithm (e.g., using one or more of a cardiac, kinetic, metabolic, EEG, or other body signal) may be used to detect seizures, and the patient's heart rate may be determined proximate the seizure detection to determine if the seizure is accompanied by a decrease in the patient's heart rate. If the seizure is accompanied by a slowing of the patient's heart rate, the first electrical signal may be suspended, and a second electrical signal may be applied to slow the patient's heart rate. The method may further include sensing the patient's heart rate during or after application of the second electrical signal. In one embodiment, the second electrical signal may be modified (e.g., by changing current magnitude, pulse width, or pulse frequency), or suspended (and possibly resumed) to maintain the patient's heart rate between an upper heart rate threshold and a lower heart rate threshold. In some embodiments, the upper and lower heart rate thresholds may be dynamically set (e.g., as no more than 5 bpm above or below the baseline HR prior to the seizure detection).

Figure 9:
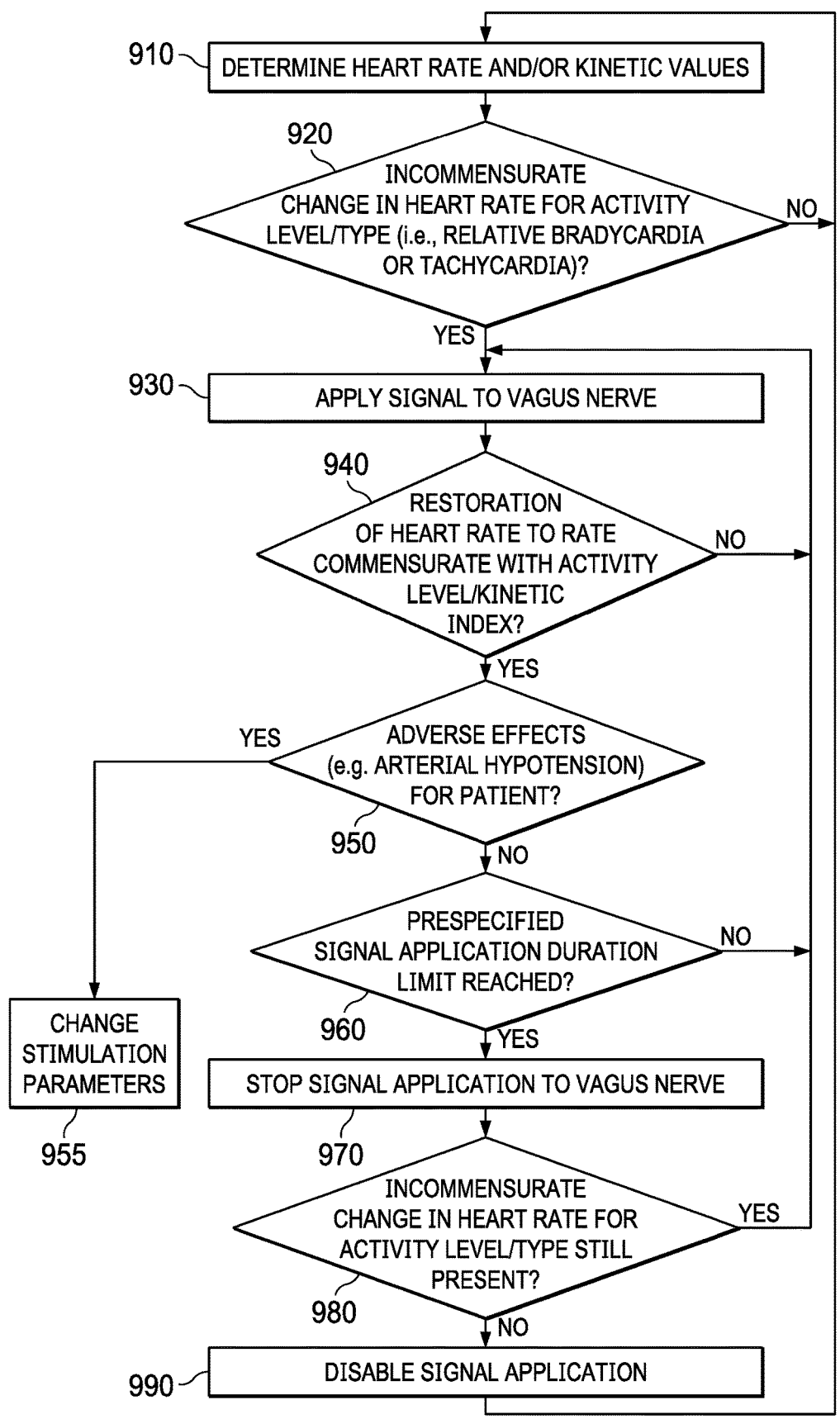
FIG. 9 is a flowchart depicting a method for providing closed-loop vagus nerve stimulation based on an assessment of whether the patient's heart rate is commensurate with the patient's activity level or activity type.

FIG. 9 is a flow diagram of a method of treating a patient with epilepsy by providing closed-loop vagus nerve intervention (e.g., stimulation or blockage of impulse conduction) to maintain the patient's heart rate within a range that is both safe and also commensurate with the activity type or level and state of the patient (e.g., as determined from a kinetic signal from a sensing element such as a triaxial accelerometer or by measuring oxygen consumption). In one embodiment, the method comprises providing vagus nerve stimulation in response to determining that a heart rate is incommensurate with the kinetic signal of the patient, to restore cardiac function to a rate that is commensurate with the patient's kinetic signal. In one embodiment, the stimulation may comprise stimulating a right vagus nerve to slow the patient's heart rate to a level that is safe and/or commensurate with activity level. In another embodiment, the stimulation may comprise providing a blocking signal to increase a slow heart rate to a rate that is safe and/or commensurate with the activity level. Pharmacologic compounds (e.g., drugs) with sympathetic or parasympathetic effects (e.g., enhancing or blocking sympathetic or parasympathetic activity) may be used to restore heart rate to a rate commensurate with kinetic activity of the patient in still other embodiments. In one embodiment, the method involves determining a heart rate and one or more kinetic or metabolic (e.g., oxygen consumption) indices for the patient (910). Heart rate may be determined from an acquired cardiac signal (e.g., from a sensor or stored data). Kinetic and/or metabolic indices may likewise be determined from a kinetic sensor (e.g., an accelerometer, a positional sensor, a GPS device coupled to a clock, or a postural sensor), a metabolic sensor, or from stored data. Sensor data may be subjected to one or more operations such as amplifying, filtering, A/D conversion, and/or other pre-processing and processing operations to enable determination of heart rate (and in some embodiments other cardiac indices such as heart rate variability) and kinetic indices.

The activity level of the patient may be determined from multiple kinetic indications such as an activity level, a type of activity, a posture, a body position, a trunk or limb acceleration or force, or a duration of one of the foregoing, and may be adapted or modified as a function of age, gender, body mass index, fitness level or time of day or other indices of the patient's condition or environment. For example, the kinetic signal may be processed to provide indices that indicate moderate ambulatory motion for an upright patient, vigorous physical exercise (in which the patient may be upright as in running or in a prone position as in some calisthenics exercises), a fall (e.g., associated with a seizure), reclining, resting or sleeping, among other activity levels and kinetic states.

The one or more kinetic indices may then be used to determine (e.g., by retrieving stored data from a lookup table or by calculation using an algorithm) one or more heart rate ranges or values that would be commensurate with the kinetic activity and/or kinetic state, duration, time of day, etc. associated with the indices. In some embodiments, heart rate ranges may be established for particular levels or types of activity (e.g., running, walking), that may be adaptively adjusted depending upon various factors such as the duration of the activity, the patient's fitness level, the time of day, a level of fatigue, an environmental temperature, etc. A commensurate heart rate is one that is within expected ranges or values for the person's effort, and for factors inherent to the patient and the environment.

Returning to FIG. 9, the determined heart rate may be compared to the range(s)/value(s) identified as commensurate with the kinetic indices (920) at a given time point. If the actual heart rate of the patient is within the expected/commensurate range or value associated with the kinetic or metabolic indices at the time point, or is within a specified proximity of a particular range or value, no action may be taken, and the method may involve continuing to analyze the patient's cardiac and kinetic signals or metabolic signals. On the other hand, if the heart rate is outside the expected value or range of values for the kinetic or metabolic indices for that time point, then the heart rate is not commensurate with the kinetic signal of the patient, and a therapy may be provided to the patient by applying one of an electrical, thermal, mechanical or chemical signal to a vagus nerve of the patient (930) or administering to the patient (e.g., intravenously, through mucosae) a drug with cholinergic or anti-cholinergic or adrenergic actions, depending on the case or situation. In one embodiment, the method may comprise applying the signal to a main trunk of a vagus nerve of the patient, and in another embodiment, the signal may be applied to a cardiac branch of a vagus nerve.

In one embodiment, the heart rate of the patient may be higher than a value commensurate with the activity level or kinetic indices of the patient. In this case, the patient is having relative tachycardia. Where this is the case, as previously noted, vagus nerve stimulation may be applied to one or more of a right cardiac branch, left cardiac branch, or right main trunk of the patient's vagus nerve to reduce the patient's heart rate to a rate that is commensurate with the activity level. Embodiments of the disclosure may be used to treat epileptic seizures associated with tachycardia, and other medical conditions associated with tachycardia given the patient's activity level. Therapies (e.g., electrical, chemical, mechanical, thermal) delivered to a patient via the vagus nerves may be employed for tachyarrythmias, angina pectoris or pain in regions innervated by a vagus nerve.

In another embodiment, the patient's heart rate may be lower than a value commensurate with the patient's activity level or kinetic indices, that is, the patient is having relative or absolute bradycardia. High frequency (>>300 Hz) electrical pulses may be applied to the left or right vagus nerves (e.g., a main trunk of the right and/or left vagus nerves or to their cardiac branches) to block propagation of transmission of nerve impulses through their fibers. High-frequency VNS may be applied to block impulses traveling to the heart to abate neurogenic, cardiogenic or iatrogenic bradycardia, or to minimize the cumulative effects on the heart's conduction system and myocardium of epileptic seizures, especially in status epilepticus. Selective blockage of impulses traveling through a vagus nerve to the heart may be accomplished with electrical stimulation to treat adverse cardiac effects associated with disorders such as epilepsy, depression, diabetes or obesity. By blocking vagus nerve conduction to the heart, when the patient's heart rate is incommensurate with the activity level or kinetic indices, a therapy may be provided to revert the change in heart rate (whether the change involves bradycardia or tachycardia). In one embodiment, an electrical signal generator may be used to apply a first therapy signal to a vagus nerve of the patient, and an electrical signal generator (which may be the same or a different electrical signal generator) may apply a vagus nerve conduction blocking electrical signal to a vagus nerve (e.g., a cardiac branch of the vagus nerve) to block cardiac effects that would result from the first electrical signal, absent the vagus nerve conduction blocking electrical signal.

Referring again to FIG. 9, the method may comprise determining the patient's heart rate in response the therapy to determine whether the heart rate has been restored to a rate that is with commensurate with the patient's activity level/kinetic index (940). If not, then the therapy (e.g., VNS to reduce or increase heart rate to an appropriate value) may be continued, with or without parameter modification, or re-initiated after a delay period or confirmation period.

If the heart rate has returned to a range/value commensurate with the activity level of the patient, the method may, in some embodiments, further involve determining whether or not an adverse event has occurred (950). Adverse events may include, without limitation, side effects such as voice alteration, pain, difficulty breathing or other respiratory effects, adverse cardiac effects such as bradycardia (following a determination of relative tachycardia in step 920), tachycardia (following a determination of bradycardia in step 920), and alteration in blood pressure or gastro-intestinal activity.

If an adverse event has occurred, the method may involve changing one or more stimulation parameters to eliminate, reduce or ameliorate the adverse event (955). If no adverse event has occurred, the method may comprise continuing to apply a signal the vagus nerve until a predetermined signal application duration has been reached (960), at which time the signal application may be stopped (970). The method may further comprise determining, after the therapy has been stopped, if the patient's heart rate remains incommensurate with the patient's activity level or type (980), in which case the signal application may be resumed or other appropriate action may be taken (e.g., local or remote alarms or alerts, notification of caregivers/healthcare providers, etc.). If the heart rate has returned to a value that is commensurate or appropriate for the patient's activity level, the signal application may be discontinued (990).

Figure 10:
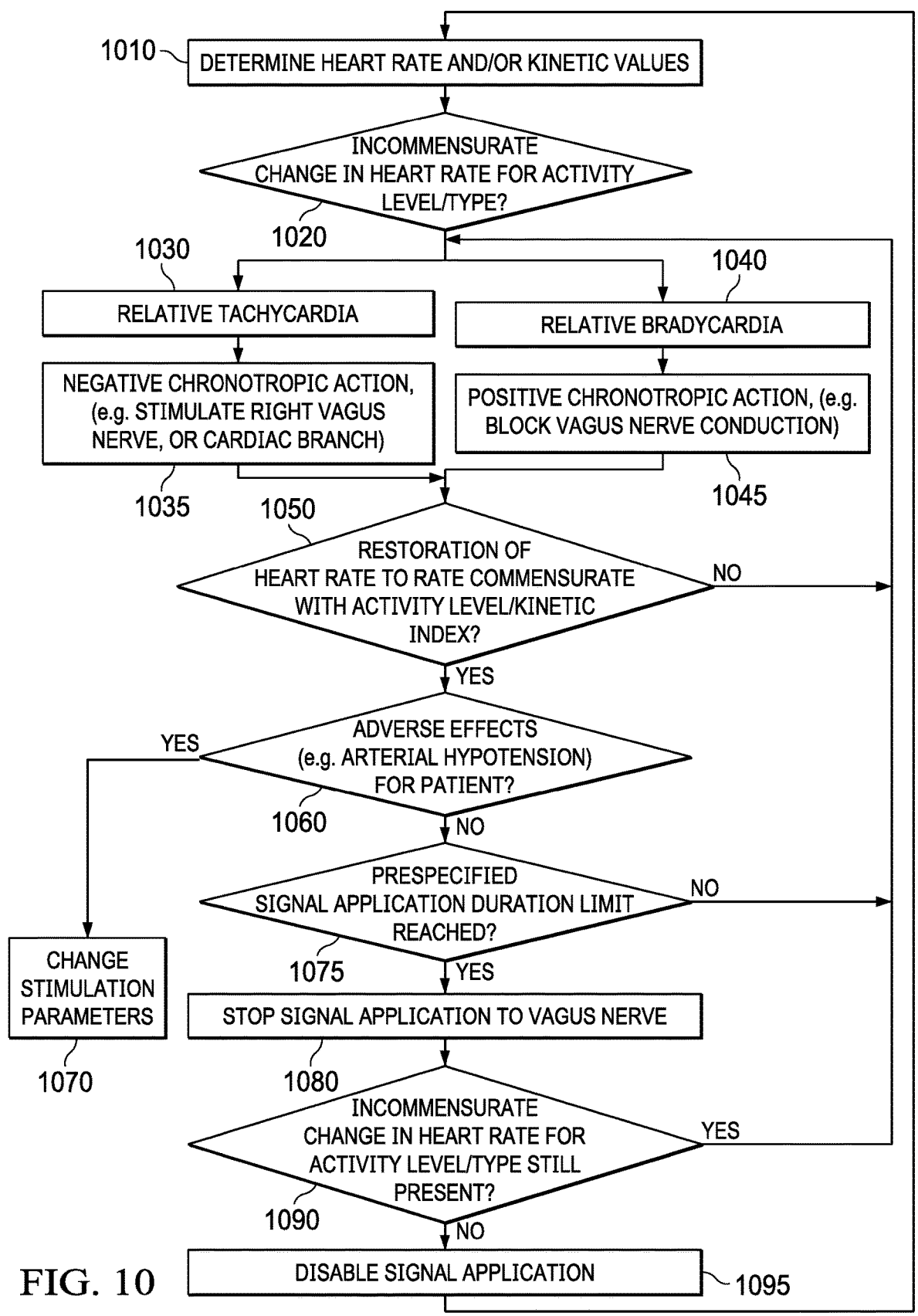
FIG. 10 is a flowchart depicting a method for providing closed-loop vagus nerve stimulation based on a determination that the patient's heart rate is incommensurate with the patient's activity level or activity type, and further in view of whether the incommensurate changes involves relative tachycardia or relative bradycardia.

FIG. 10 is a flow diagram of a method of treating a patient to with epilepsy by providing closed-loop vagus nerve stimulation to treat relative tachycardia or relative bradycardia by restoring the patient's heart rate to a rate that is commensurate with the activity type or level of the patient (e.g., as determined from a kinetic signal from a sensing element such as a triaxial accelerometer or by measuring oxygen consumption). In one embodiment, the method comprises identifying instances of relative tachycardia or relative bradycardia and responding with negative or positive chronotropic actions to restore the heart rate to a level commensurate with the patient's activity type or level.

In one embodiment, the method involves determining a heart rate and an activity type or level for the patient (1010). The patient's heart rate may be determined from an acquired cardiac signal or from stored data. The activity level or type of the patient may be determined from one or more sensor or from stored data. Sensors may include, for example, accelerometers, positional sensors, GPS devices coupled to a clock, postural sensors, and metabolic sensors. Sensor data may be subject to conventional signal processing, and may in addition be adapted or modified as a function of age, gender, body mass index, fitness level or time of day or other indices of the patient's condition or environment.

The patient's activity type or level may then be used to determine one or more heart rate ranges or values that are commensurate with the activity type or level (1020). In some embodiments, heart rate ranges may be established for particular levels or types of activity (e.g., running, walking), that may be adaptively adjusted depending upon various factors such as the duration of the activity, the patient's fitness level, the time of day, a level of fatigue, an environmental temperature, etc. A commensurate heart rate is one that is within expected ranges or values for the person's effort, and for factors inherent to the patient and the environment.

If the heart rate is commensurate with the activity level, in one embodiment no action may be taken, and the method may involve continuing to analyze the patient's cardiac and activity. On the other hand, if the heart rate is outside the identified value or range of values appropriate for the patient's activity type or level then the heart rate is not commensurate with the kinetic signal of the patient. Where this is the case, the method may further comprise determining whether the patient is experiencing relative tachycardia or is experiencing relative bradycardia (1030, 1040).

Where the heart rate of the patient is higher than a value commensurate with the activity level or type, the patient is experiencing relative tachycardia (1030), and the method may comprise initiating a negative chronotropic action (1035) to slow the heart rate to a rate that is commensurate with the activity level or type. In one embodiment, this may involve applying stimulation to one or more of a left or right main vagal trunk or cardiac branch of the patient. In other embodiments, the method may comprise providing a drug to enhance the parasympathetic tone of the patient. In still other embodiments, the method may comprise reducing the patient's sympathetic tone, such as by applying high-frequency stimulation to a sympathetic nerve trunk or ganglion or administering an anti-cholinergic drug. Negative chronotropic actions may be used to treat epileptic seizures associated with tachycardia, and other medical conditions associated with relative tachycardia given the patient's activity level.

Where the heart rate of the patient is lower than a value commensurate with the activity level or type, the patient is experiencing relative bradycardia (1040), and the method may comprise initiating a positive chronotropic action (1045) to increase the heart rate to a rate that is commensurate with the activity level or type. In one embodiment, this may involve applying high-frequency (>>300 Hz) electrical stimulation to one or more of a left or right main vagal trunk or cardiac branch of the patient to reduce the transmission of intrinsic vagus nerve action potentials in at least some vagal fibers. In other embodiments, the method may comprise providing a drug to reduce the parasympathetic tone of the patient. In still other embodiments, the method may comprise increasing the patient's sympathetic tone, such as by applying electrical signals to a sympathetic nerve trunk or ganglion or by administering a sympatho-mimetic drug. Positive chronotropic actions may be used to treat epileptic seizures associated with bradycardia, and other medical conditions associated with relative bradycardia given the patient's activity level.

The method may further comprise, after initiating the negative or positive chronotropic action, determining whether the patient's heart rate has been restored to a rate that is with commensurate with the patient's activity level/kinetic index (1050). If not, then the therapy (e.g., VNS to reduce or increase heart rate to an appropriate value) may be continued, with or without parameter modification, or re-initiated after a delay period or confirmation period.

If the heart rate has returned to a range/value commensurate with the activity level of the patient, the method may, in some embodiments, further involve determining whether or not an adverse event has occurred (1060). Adverse events may include, without limitation, side effects such as voice alteration, pain, difficulty breathing or other respiratory effects, adverse cardiac effects such as bradycardia (following a determination of relative tachycardia in step 1030), or tachycardia (following a determination of bradycardia in step 1040), and alteration in blood pressure or gastric activity.

If an adverse event has occurred, the method may involve changing one or more stimulation parameters to eliminate, reduce or ameliorate the adverse event (1070). If no adverse event has occurred, the method may comprise continuing to stimulate the vagus nerve (or a chemical, thermal or mechanical therapy) until a predetermined stimulation duration has been reached (1075), at which time the stimulation may be stopped (1080). The method may further comprise determining, after the therapy has been stopped, if the patient's heart rate remains incommensurate with the patient's activity level or type (1090), in which case the stimulation may be resumed or other appropriate action may be taken (e.g., local or remote alarms or alerts, notification of caregivers/healthcare providers, use of other forms of therapy, etc.). If the heart rate has returned to a value that is commensurate or appropriate for the patient's activity level, the stimulation may be discontinued (1095).

Additional embodiments consistent with the foregoing description and figures may be made. Non-limiting examples of some such embodiments are provided in the numbered paragraphs below.

100. A method of controlling a heart rate of an epilepsy patient comprising:
sensing at least one of a kinetic signal and a metabolic signal of the patient;
analyzing the at least one of a kinetic and a metabolic signal to determine at least one of a kinetic index and a metabolic index;
receiving a cardiac signal of the patient;
analyzing the cardiac signal to determine the patient's heart rate;
determining if the patient's heart rate is commensurate with the at least one of a kinetic index and a metabolic index; and
applying an electrical signal to a vagus nerve of the patient based on a determination that the patient's heart rate is not commensurate with the at least one of a kinetic signal and a metabolic signal of the patient.

101. The method of numbered paragraph 100, wherein determining at least one of a kinetic index and a metabolic index comprises determining at least one of an activity level or an activity type of the patient based on the at least one of a kinetic index and a metabolic index, and wherein determining if the patient's heart rate is commensurate with the at least one of a kinetic index and a metabolic index of the patient comprises determining if the heart rate is commensurate with the at least one of an activity level or an activity type.

102. The method of numbered paragraph 101, wherein determining if the patient's heart rate is commensurate with the at least one of a kinetic index and a metabolic index comprises determining if the patient's heart rate is above or below a rate that is commensurate with the one or more of a kinetic index and a metabolic index.

103. A method of treating a patient having epilepsy comprising
sensing at least one body signal of the patient;
determining whether or not the patient is having or has had an epileptic seizure based on the at least one body signal;
sensing a cardiac signal of the patient;
determining whether or not the seizure is associated with a change in the patient's cardiac signal;

applying a first therapy to a vagus nerve of the patient based on a determination that the patient is having or has had an epileptic seizure that is not associated with a change in the patient's cardiac signal, wherein the first therapy is selected from an electrical, chemical, mechanical, or thermal signal; and applying a second therapy to a vagus nerve of the patient based on a determination that the patient is having or has had an epileptic seizure associated with a change in the patient's cardiac signal, wherein the second therapy is selected from an electrical, chemical, mechanical (e.g., pressure) or thermal signal.

104. The method of numbered paragraph 103, further comprising applying a third therapy to a vagus nerve of the patient based a determination that the patient is not having or has not had an epileptic seizure, wherein the third therapy is selected from an electrical, chemical, mechanical or thermal signal.

105. A method of treating a patient having epilepsy comprising:
coupling a first set of electrodes to a main trunk of the left vagus nerve of the patient;
coupling a second set of electrodes to a main trunk of the right vagus nerve of the patient;
providing an electrical signal generator coupled to the first electrode set and the second electrode set;
receiving at least one body data stream;
analyzing the at least one body data stream using a seizure detection algorithm to determine whether or not the patient is having and/or has had an epileptic seizure;
applying a first electrical signal from the electrical signal generator to the main trunk of the left vagus nerve, based on a determination that the patient is having and/or has had an epileptic seizure without a heart rate change; and
applying a second electrical signal from the electrical signal generator to the main trunk of the right vagus nerve, based on a determination that the patient is having or has had an epileptic seizure with a heart rate change.

106. A method of treating a patient having epilepsy comprising:
receiving at least one body data stream;
analyzing the at least one body data stream using a seizure detection algorithm to detect whether or not the patient has had an epileptic seizure;
receiving a cardiac signal of the patient;
analyzing the cardiac signal to determine a first cardiac feature;
applying a first electrical signal to a vagus nerve of the patient, based on a determination that the patient has not had an epileptic seizure characterized by a change in the first cardiac feature, wherein the first electrical signal is not a vagus nerve conduction blocking electrical signal; and
applying a second electrical signal to a vagus nerve of the patient, based on a determination that the patient has had an epileptic seizure characterized by a change in the cardiac feature, wherein the second electrical signal is a pulsed electrical signal that blocks action potential conduction in the vagus nerve.

107. A method of treating a patient having epilepsy comprising:
receiving at least one body data stream;
analyzing the at least one body data stream using a seizure detection algorithm to detect whether or not the patient has had an epileptic seizure;
receiving a cardiac signal of the patient;
analyzing the cardiac signal to determine a first cardiac feature;
applying a first electrical signal to a vagus nerve of the patient, based on a determination that the patient has not had an epileptic seizure characterized by a change in the first cardiac feature, wherein the first electrical signal is a pulsed electrical signal that blocks action potential conduction in the vagus nerve; and
applying a second electrical signal to a vagus nerve of the patient, based on a determination that the patient has had an epileptic seizure characterized by a change in the cardiac feature, wherein the second electrical signal is not a vagus nerve conduction blocking electrical signal.

Figure 11:
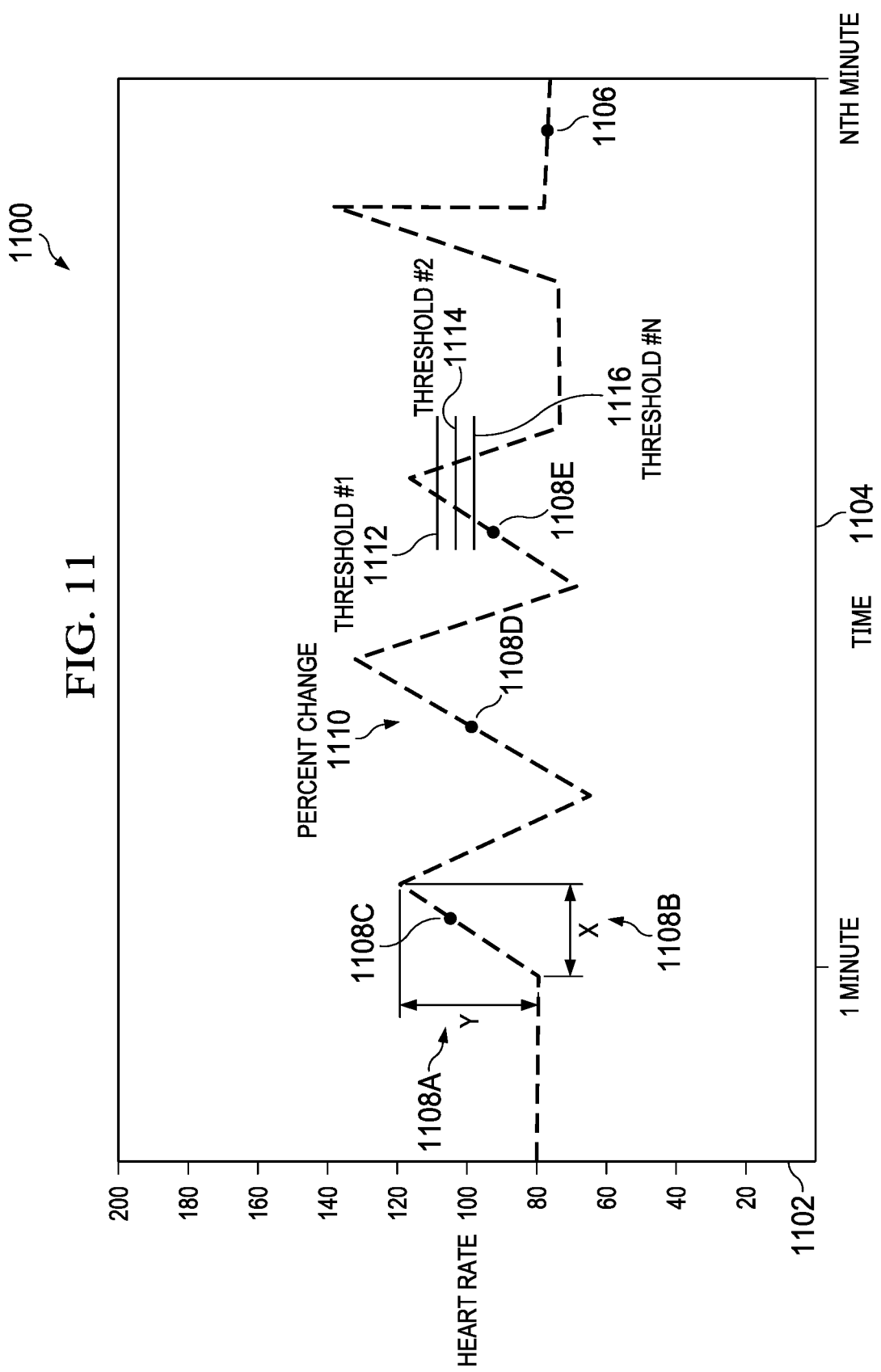
FIG. 11 is a graph of heart rate versus time, according to one embodiment.

In FIG. 11, a graph of heart rate versus time is shown, according to one embodiment. A first graph 1100 includes a y-axis 1102 which represents heart rate where the heart rate goes from a zero value to an Nth value (e.g., 200 heart beats, etc.). Further, the first graph 1100 includes an x-axis 1104 which represents time from 1 minute to Nth minutes (and/or 0.001 seconds to Nth seconds). In this example, a first heart rate versus time line 1106 for the patient is shown. In this example, the patient's heart rate goes from 80 heart beats per minute to 118 heart beats per minute with a first rise 1108A and a first run 1108B during a first event 1108C. In addition, the patient's heart rate goes from 70 heart beats per minute to 122 heart beats per minute during a second event 1108D which has a first percentage change 1110 associated with the second event 1108D. Further, the patient's heart rate goes from 70 beats per minute to 113 beats per minute during an nth event 1108E which surpasses a first threshold amount 1112, and/or a second threshold amount 1114, and/or an Nth threshold amount 1116. In one example, only the Nth threshold amount 1116 needs to be reached to trigger a therapy and/or an alert. In another example, only the second threshold amount 1114 needs to be reached to trigger a therapy and/or an alert. In another example, only the first threshold 1112 needs to be reached to trigger a therapy and/or an alert. In another example, both the Nth threshold 1116 and the second threshold 1114 need to reached to trigger a therapy and/or an alert. In another example, all of the Nth threshold 1116, the second threshold 1114 and the first threshold 1112 need to reached to trigger a therapy and/or an alert. In one example, only the Nth threshold amount 1116 needs to be reached during a specific time period to trigger a therapy and/or an alert. In another example, only the second threshold amount 1114 needs to be reached during a specific time period to trigger a therapy and/or an alert. In another example, only the first threshold 1112 needs to be reached during a specific time period to trigger a therapy and/or an alert. In another example, both the Nth threshold 1116 and the second threshold 1114 need to reached during a specific time period to trigger a therapy and/or an alert. In another example, all of the Nth threshold 1116, the second threshold 1114 and the first threshold 1112 need to reached during a specific time period to trigger a therapy and/or an alert. In these examples, one or more triggering events may occur based on a determination of the rise and run of a change in heart rate, a percentage change in heart rate, a threshold amount being reached or exceeded (or within any percentage of the threshold), and/or any combination thereof. A triggering event may initiate one or more actions to increase and/or decrease the patient's heart rate. For example, if the patient's heart rate is increasing which determines the triggering event, then the system, device, and/or method may initiate one or more actions to decrease the heart rate of the patient to help reduce, dampen, eliminate, and/or buffer the increase in the patient's heart rate. Further, the system, device, and/or method may oscillate between decreasing the patient's heart rate and increasing the patient's heart rate depending on any changes to the patient's heart rate. For example, the system, device, and/or method may initiate one or more actions to decrease a patient's heart rate based on the patient's heart rate going from 80 heart beats per minute to 130 heart beats per minute which results in the patient's heart rate falling from 130 heart beats per minute to 65 heart beats per minute in a first time period. Based on the change in the heart rate from 130 heart beats per minute to 65 heart beats per minute in the first time period, the system, device, and/or method may initiate one or more actions to increase the patient's heart rate and/or stabilize the patient's heart rate. In another example, the system, method, and/or device may stop and/or modify any initiated action based on one or more feedback signals. In addition, one or more warnings may be transmitted to the patient, a caregiver, a doctor, a medical professional, and/or logged.

Figure 12:
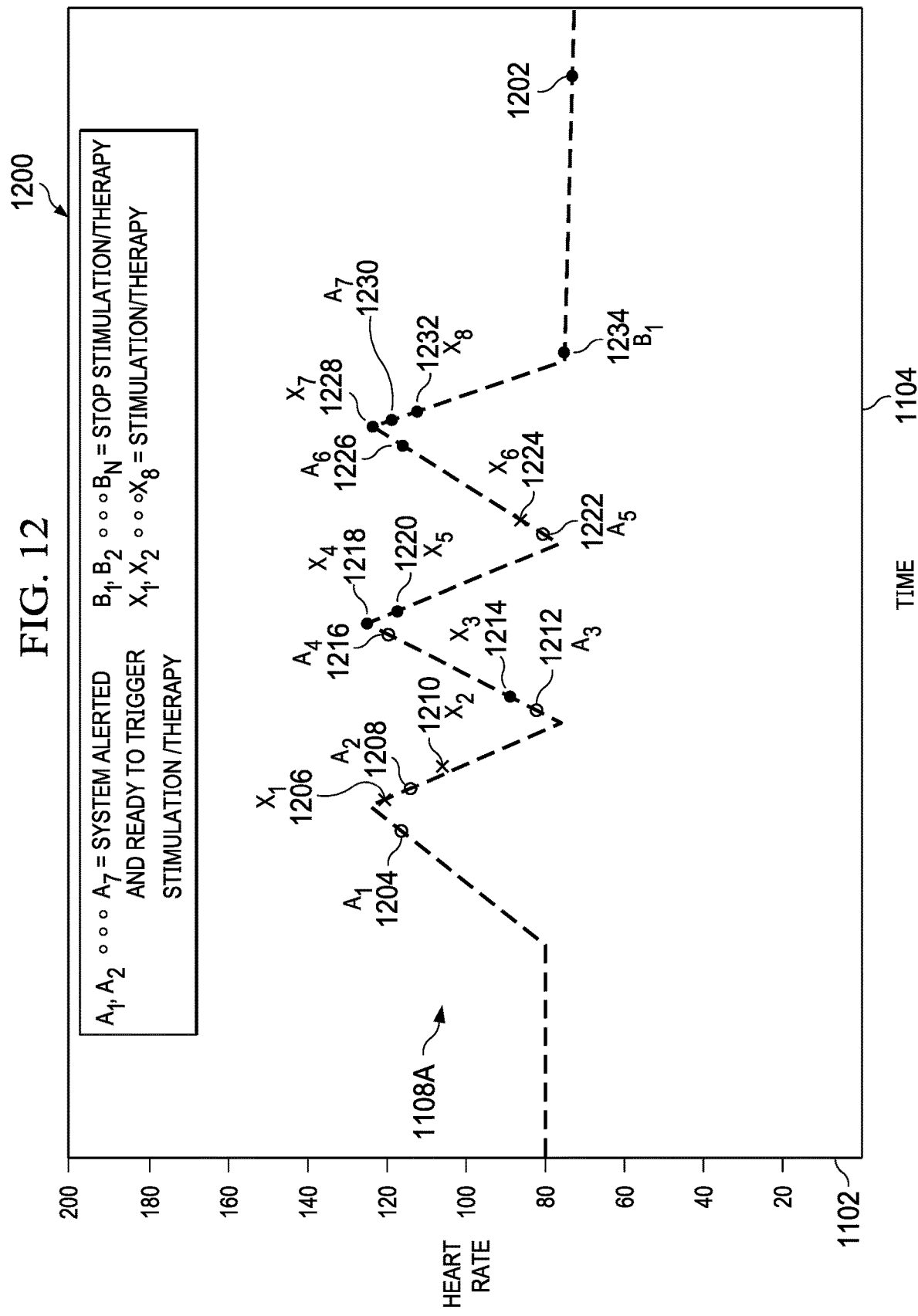
FIG. 12 is another graph of heart rate versus time, according to one embodiment.

In FIG. 12, another graph of heart rate versus time is shown, according to one embodiment. A second graph 1200 illustrating a second heart rate versus time line 1202 for the patient is shown. In this example, the patient's heart rate goes from 80 heart beats per minute to 120 heart beats per minute which creates a first system alert event 1204 (e.g., A1). Further, the system, device, and/or method initiates a first therapy 1206 (e.g., X1) based on the first system alert event 1204. In addition, a second system alert event 1208 (e.g., A2) occurs and a second therapy 1210 (e.g., X2) is initiated based on the second system alert event 1208. In addition, a third system alert event 1212 (e.g., A3) occurs and a third therapy (e.g., X3) 1214 is initiated based on the third system alert event 1212 (e.g., A3). In addition, a fourth system alert event 1216 (e.g., A4) occurs and a fourth therapy 1218 (e.g., X4) is initiated based on the fourth system alert event 1216 (e.g., A3). Further, a fifth therapy 1220 (e.g., X5) is initiated based on the effects of the fourth therapy 1218 (e.g., X4). In addition, a fifth system alert event 1222 (e.g., A5) occurs and a sixth therapy (e.g., X6) 1224 is initiated based on the fifth system alert event 1222 (e.g., A5). In addition, a sixth system alert event 1226 (e.g., A6) occurs and a seventh therapy (e.g., X7) 1228 is initiated based on the sixth system alert event 1226 (e.g., A6). In addition, a seventh system alert event 1230 (e.g., A7) occurs and an eighth therapy (e.g., X8) 1232 is initiated based on the seventh system alert event 1230 (e.g., A7). In addition, a first stop stimulation event 1234 (e.g., B1) occurs which turns off all therapies and/or system alerts may occur when the heart rate returns to the approximate starting heart rate and/or a target value. In these examples shown with FIG. 12, a rise over run heart rate calculation was completed to determine the one or more system alerts. However, it should be noted that any calculation (e.g., % increase, % decrease, etc. can be utilized). Further, all systems alerts and/or therapies may occur as independent events and/or examples. For example, the seventh system alert may be the first system alert in a specific example. In other words, no other events and/or therapies occurred before the seventh system alert. Therefore, the seventh system alert becomes the first system alert. In addition, one or more warnings may be transmitted to the patient, a caregiver, a doctor, a medical professional, and/or logged. In addition, there may be up to an Nth alerts, an Nth stop stimulation (and/or therapy) event, and an Nth therapy in any of the examples disclosed in this document.

Figure 13:
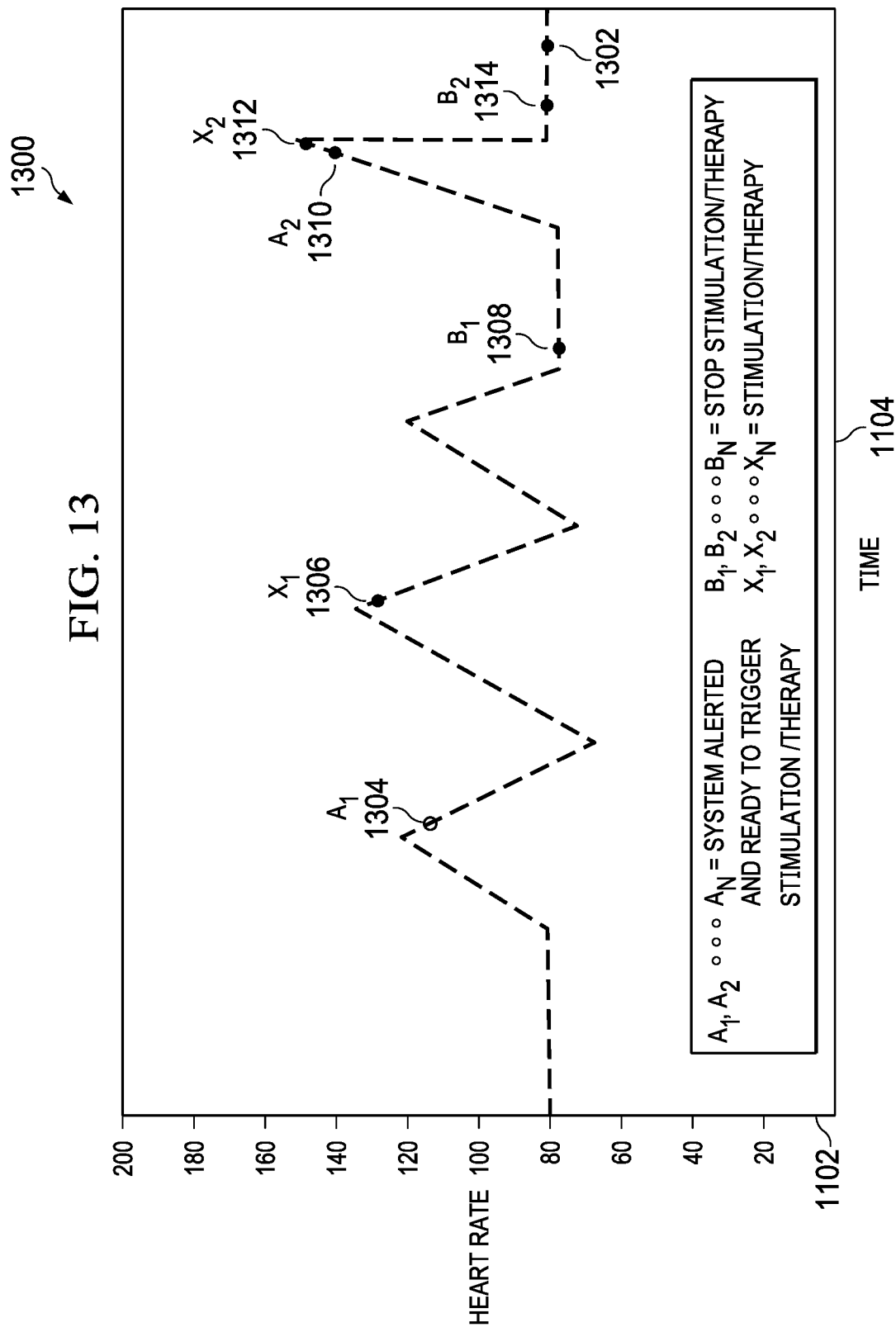
FIG. 13 is another graph of heart rate versus time, according to one embodiment.

In FIG. 13, another graph of heart rate versus time is shown, according to one embodiment. A third graph 1300 illustrating a third heart rate versus time line 1302 for the patient is shown. In this example, the patient's heart rate goes from 80 heart beats per minute to 116 heart beats per minute which creates a first system alert event 1304 (e.g., A1). Further, the system, device, and/or method initiates a first therapy 1306 (e.g., X1) based on the first system alert event 1304. In addition, a first stop stimulation event 1308 (e.g., B1) occurs which turns off all therapies and/or system alerts occurs when the heart rate returns to the approximate starting heart rate and/or a target value. Further, the patient's heart rate goes from 80 heart beats per minute to 123 heart beats per minute which creates a second system alert event 1310 (e.g., A2). Further, the system, device, and/or method initiates a second therapy 1312 (e.g., X2) based on the second system alert event 1310. In addition, a second stop stimulation event 1314 (e.g., B2) occurs which turns off all therapies and/or system alerts occurs when the heart rate returns to the approximate starting heart rate and/or a target value. In these examples shown with FIG. 13, a percentage change in heart rate calculation was completed to determine the one or more system alerts. However, it should be noted that any calculation (e.g., rise over run, etc. can be utilized). Further, all systems alerts and/or therapies may occur as independent events and/or examples. For example, the second system alert may be the first system alert in a specific example In other words, no other events and/or therapies occurred before the second system alert. Therefore, the second system alert becomes the first system alert. In addition, one or more warnings may be transmitted to the patient, a caregiver, a doctor, a medical professional, and/or logged.

Figure 14:
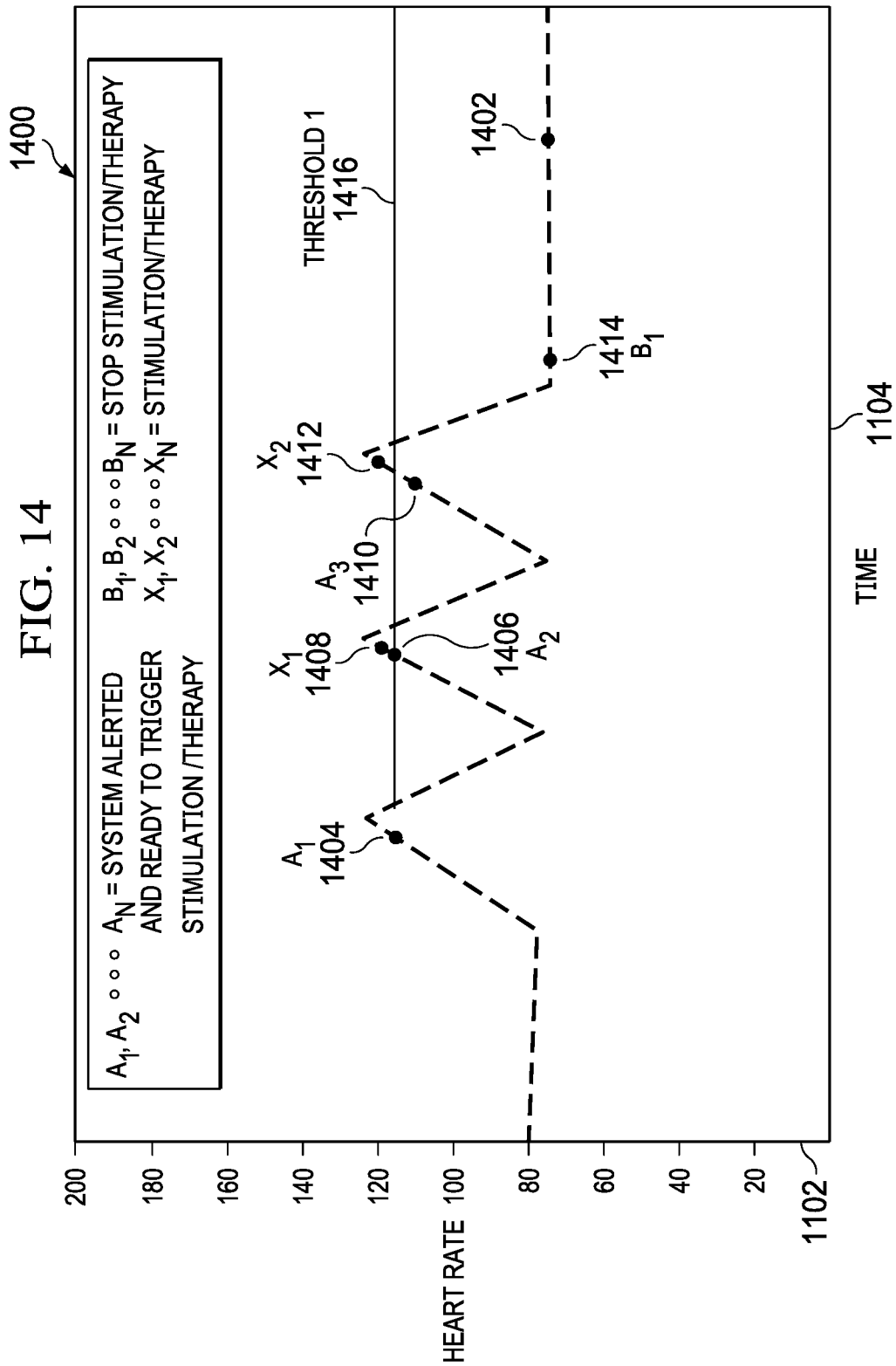
FIG. 14 is another graph of heart rate versus time, according to one embodiment.

In FIG. 14, another graph of heart rate versus time is shown, according to one embodiment. A fourth graph 1400 illustrating a fourth heart rate versus time line 1402 for the patient is shown. In this example, the patient's heart rate goes from 80 heart beats per minute to 120 heart beats per minute which creates a first system alert event 1404 (e.g., A1) because the 120 heart beats per minutes meets or exceeds a first threshold value 1416 (e.g., 115 heart beats per minute). In this example, a second system alert event 1406 (e.g., A2) is created because the heart beats of the patient meets or exceeds the first threshold value 1416 (e.g., 115 heart beats per minute). Further, the system, device, and/or method initiates a first therapy 1408 (e.g., X1) based on the first system alert event 1404 and the second system alert event 1406 occurring. The first system alert event 1404 and the second system alert event 1406 may be time dependent. For example, the first system alert event 1404 and the second system alert event 1406 may have to occur within a first time period for the initiation of the first therapy 1408. In another example, the first system alert event 1404 and the second system alert event 1406 may not be time dependent. Further, a third system alert event 1410 (e.g., A3) is created because the heart beats of the patient meets or exceeds (and/or within a specific rate of the threshold—in this example within 5 percent—heart rate is 110) the first threshold value 1416 (e.g., 115 heart beats per minute). Further, the system, device, and/or method initiates a second therapy 1412 (e.g., X2) based on the first system alert event 1404, the second system alert event 1406, and/or the third system event occurring. It should be noted that the second therapy 1412 has a time delay factor utilized with the second therapy 1412. In another example, no time delay is utilized. In addition, one or more time delays can be used with any therapy, any warning, and/or any alert in this document. The first system alert event 1404, the second system alert event 1406, and the third system alert event 1410 may be time dependent. For example, the first system alert event 1404, the second system alert event 1406, and the third system alert event 1410 may have to occur within a first time period for the initiation of the second therapy 1412. In another example, the first system alert event 1404, the second system alert event 1406, and the third system alert event 1410 may not be time dependent. Further, a first stop stimulation event 1414 (e.g., B1) occurs which turns off all therapies and/or system alerts occurs when the heart rate returns to the approximate starting heart rate and/or a target value. Further, all systems alerts and/or therapies may occur as independent events and/or examples. For example, the third system alert may be the first system alert in a specific example. In other words, no other events and/or therapies occurred before the third system alert. Therefore, the third system alert becomes the first system alert. In addition, one or more warnings may be transmitted to the patient, a caregiver, a doctor, a medical professional, and/or logged.

Figure 15:
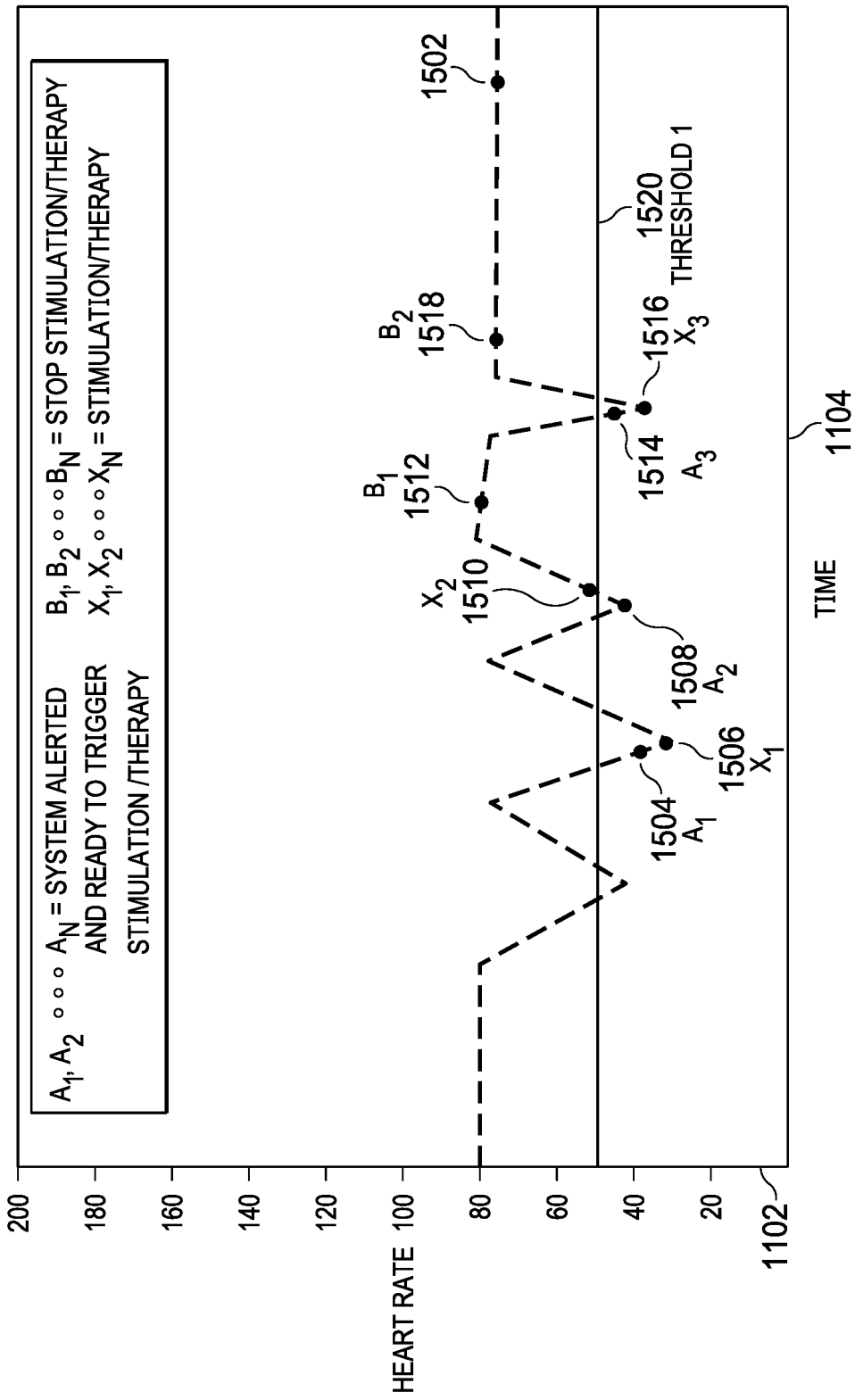
FIG. 15 is another graph of heart rate versus time, according to one embodiment.

In FIG. 15, another graph of heart rate versus time is shown, according to one embodiment. A fifth graph 1500 illustrating a fifth heart rate versus time line 1502 for the patient is shown. In this example, the patient's heart rate goes from 80 heart beats per minute to 40 heart beats per minute which creates a first system alert event 1504 (e.g., A1) because the 40 heart beats per minutes meets or exceeds a first threshold value 1520 (e.g., 50 heart beats per minute). It should be noted that no alert was generated when the heart rate fell to 52 heart beats per minute because 52 heart beats per minute is above the threshold value of 50 heart beats per minute. Further, the system, device, and/or method initiates a first therapy 1506 (e.g., X1) based on the first system alert event 1504 occurring. Further, the patient's heart rate goes from 80 heart beats per minute to 50 heart beats per minute which creates a second system alert event 1508 (e.g., A2) because the 50 heart beats per minutes meets or exceeds the first threshold value 1520 (e.g., 50 heart beats per minute). Further, the system, device, and/or method initiates a second therapy 1510 (e.g., X2) based on the second system alert event 1508 occurring. Further, a first stop stimulation event 1512 (e.g., B1) occurs which turns off all therapies and/or system alerts occurs when the heart rate returns to the approximate starting heart rate and/or a target value. In addition, the patient's heart rate goes from 80 heart beats per minute to 45 heart beats per minute which creates an nth system alert event 1514 (e.g., A3) because the 45 heart beats per minutes meets or exceeds the first threshold value 1520 (e.g., 50 heart beats per minute). Further, the system, device, and/or method initiates an Nth therapy 1516 (e.g., X3) based on the nth system alert event 1514 occurring. Further, an nth stop stimulation event 1518 (e.g., B2) occurs which turns off all therapies and/or system alerts occurs when the heart rate returns to the approximate starting heart rate and/or a target value. Further, all systems alerts and/or therapies may occur as independent events and/or examples. For example, nth system alert event 1514 alert may be the first system alert in a specific example. In other words, no other events and/or therapies occurred before nth system alert event 1514. Therefore, nth system alert event 1514 becomes the first system alert. In addition, one or more warnings may be transmitted to the patient, a caregiver, a doctor, a medical professional, and/or logged.

In regards to FIGS. 11-15 as related to this disclosure, the systems, devices, and/or methods may use a base line heart rate for the patient (e.g., a specific patient Bob, a general patient John Doe with a first health condition, a first age, etc.) over a first time period (e.g. one week, one month, one year, etc.), 50 percentile of all measured heart rates, an average of all heart rates, and/or any other method of determine a baseline heart rate. Further, the threshold level may be determined based on being the 40 percentile of the baseline, 39 percentile of the baseline, 38 percentile of the baseline, . . . , 10 percentile of the baseline, . . . , etc. In addition, the threshold level may be determined based on being the 75 percentile of the baseline, 76 percentile of the baseline, 77 percentile of the baseline, . . . , 90 percentile of the baseline, . . . , 99 percentile of the baseline, . . . , etc. In one example, the threshold value may be the 75 percentile of every recorded heart rate data. In another example, the oscillation does not matter whether the heart rate change is in an increasing direction or a decreasing direction. In various examples, the systems, devices, and/or method may reduce an amplitude of change (e.g., damping the change in heart rate) to enhance system performance and/or to reduce side effects. In addition, the determination of one or more side effects may initiate a reduction in therapy, a stoppage of therapy, a modification of therapy (e.g., changing a therapy that reduces heart rate to another therapy that increases heart rate), one or more warnings, and/or one or more logging of data.

Figure 16:
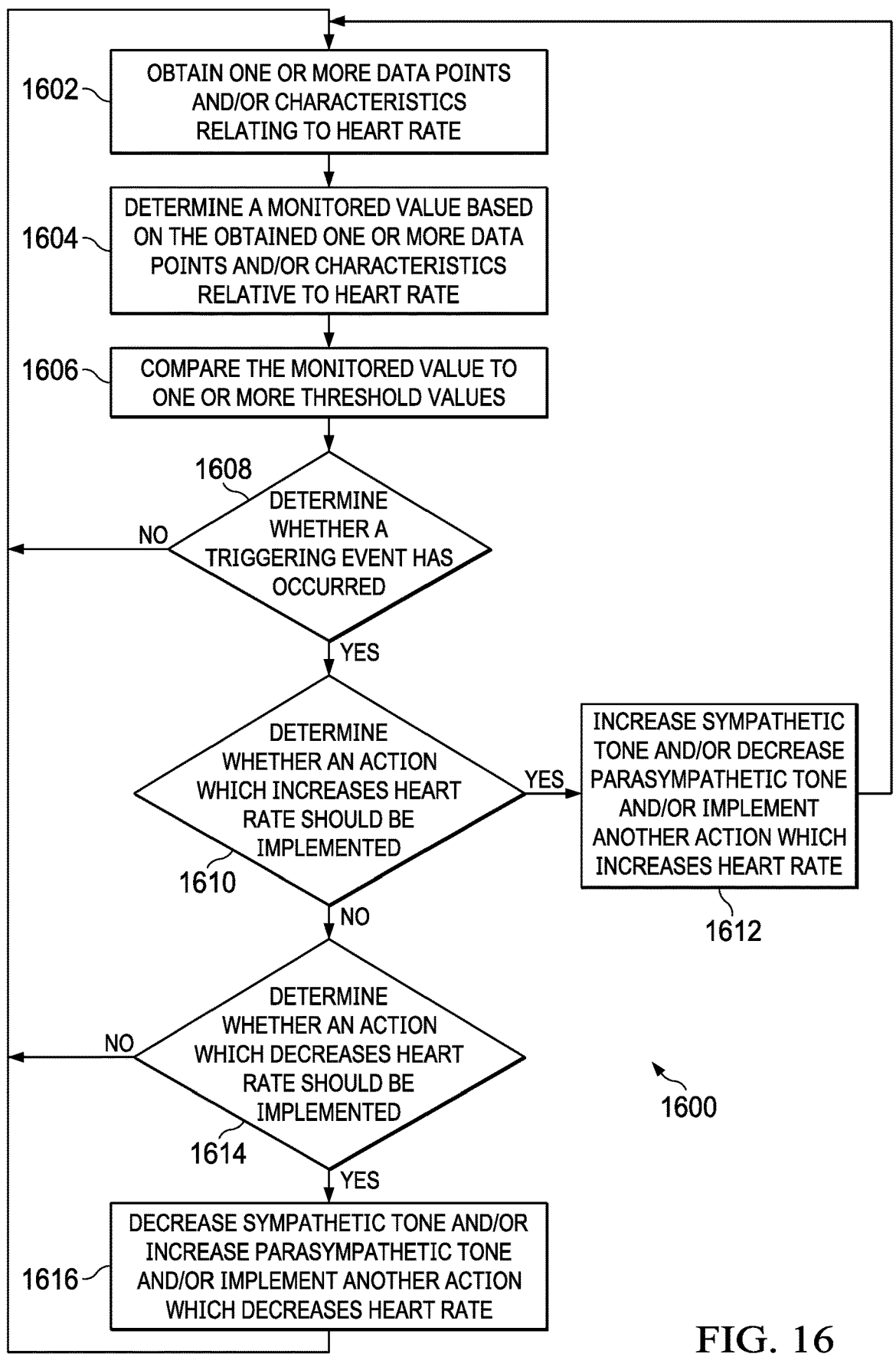
FIG. 16 is a flowchart of a therapy procedure, according to one embodiment.

In FIG. 16, a flowchart of a therapy procedure is shown, according to one embodiment. A method 1600 includes obtaining one or more data points and/or characteristics relating to heart rate of a patient (step 1602). The method 1600 may also include determining a monitored value based one the obtained one or more data points and/or characteristics relating to the heart rate (step 1604). The method 1600 may further compare the monitored value to one or more threshold values (step 1606). The method 1600 may via one or more processors (of a medical device(s) and/or medical device system) determine whether a triggering event has occurred (step 1608). If no triggering event has occurred, then the method 1600 moves back to step 1602. If a triggering event has occurred, then the method 1600 may determine via one or more processors (of a medical device(s) and/or medical device system) whether an action which increases heart rate should be implemented (step 1610). If an action which increases heart rate should be implemented, then the method 1600 may increase a sympathetic tone via one or more actions and/or decrease a parasympathetic tone via one or more actions and/or implement another action which increases heart rate (step 1612). After the implements of one or more actions, the method 1600 returns to step 1602. If an action which increases heart rate should not be implemented, then the method 1600 may determine via one or more processors (of a medical device(s) and/or medical device system) whether an action which decreases heart rate should be implemented (step 1614). If an action which decreases heart rate should be implemented, then the method 1600 may decrease a sympathetic tone via one or more actions and/or increase a parasympathetic tone via one or more actions and/or implement another action which decreases heart rate (step 1616). After the implements of one or more actions, the method 1600 returns to step 1602.

In one embodiment, a system for treating a medical condition in a patient includes: a sensor for sensing at least one body data stream; a heart rate unit capable of determining a heart rate of the patient based on the at least one body data stream; and a logic unit configured via one or more processors to compare a monitored value which is determined based on one or more data points relating to the heart rate to one or more threshold values, the logic unit further configured to determine a triggering event based on the comparison. Further, the one or more processors may initiate one or more actions to change the heart rate of the patient based on the determination of the triggering event.

In another example, the system includes at least one electrode coupled to a vagus nerve of the patient and a programmable electrical signal generator. In another example, the one or more processors may increase a sympathetic tone to increase the heart rate of the patient. In another example, the one or more processors may decrease a parasympathetic tone to increase the heart rate of the patient. In another example, the one or more processors may decrease a sympathetic tone to decrease the heart rate of the patient. In another example, the one or more processors may increase a parasympathetic tone to decrease the heart rate of the patient. In another example, the system includes a seizure detection unit which analyzes the at least one body data stream to determine an epileptic seizure status. In another example, the system includes at least one electrode coupled to a vagus nerve of the patient and a programmable electrical signal generator. Further, the one or more processors may apply an electrical signal to the vagus nerve of the patient based on a determination that a seizure is characterized by a decrease in the heart rate of the patient where the electrical signal is applied to block action potential conduction on the vagus nerve.

In another embodiment, a system for treating a medical condition in a patient, includes: a sensor for sensing at least one body data stream; at least one electrode coupled to a vagus nerve of the patient; a programmable electrical signal generator; a heart rate unit capable of determining a heart rate of the patient based on the at least one body data stream; and a logic unit configured via one or more processors to compare a monitored value which is determined based on one or more data points relating to the heart rate to one or more threshold values, the logic unit further configured to determine a triggering event based on the comparison. Further, the one or more processors may initiate one or more actions to change the heart rate of the patient based on the determination of the triggering event.

In another example, the one or more processors may increase a sympathetic tone to increase the heart rate of the patient based on a first triggering event. Further, the one or more processors may decrease a sympathetic tone to decrease the heart rate of the patient based on a second triggering event. Further, the one or more processors may decrease a parasympathetic tone to increase the heart rate of the patient based on a third triggering event. Further, the one or more processors may increase a parasympathetic tone to decrease the heart rate of the patient based on a fourth triggering event.

In another example, the one or more processors may increase the sympathetic tone to increase the heart rate of the patient based on a second triggering event. Further, the one or more processors may increase the sympathetic tone to increase the heart rate of the patient based on a third triggering event. Further, the one or more processors increase the sympathetic tone to increase the heart rate of the patient based on an nth triggering event.

In another example, the one or more processors decrease a sympathetic tone to decrease the heart rate of the patient based on a first triggering event. Further, the one or more processors decrease the sympathetic tone to decrease the heart rate of the patient based on a second triggering event. Further, the one or more processors may decrease the sympathetic tone to decrease the heart rate of the patient based on a third triggering event. In addition, the one or more processors decrease the sympathetic tone to decrease the heart rate of the patient based on an nth triggering event.

Cardio-protection in epilepsy is a rapidly growing field of vital importance. In this disclosure, systems, devices, and/or method of protecting the heart from standstill or fatal arhythmias are disclosed. Further in this disclosure, systems, devices, and/or methods of automated detections, warnings, reportings, treatments, controls and/or any combination thereof of ictal and peri-ictal chronotropic instability are shown.

Figure 17:
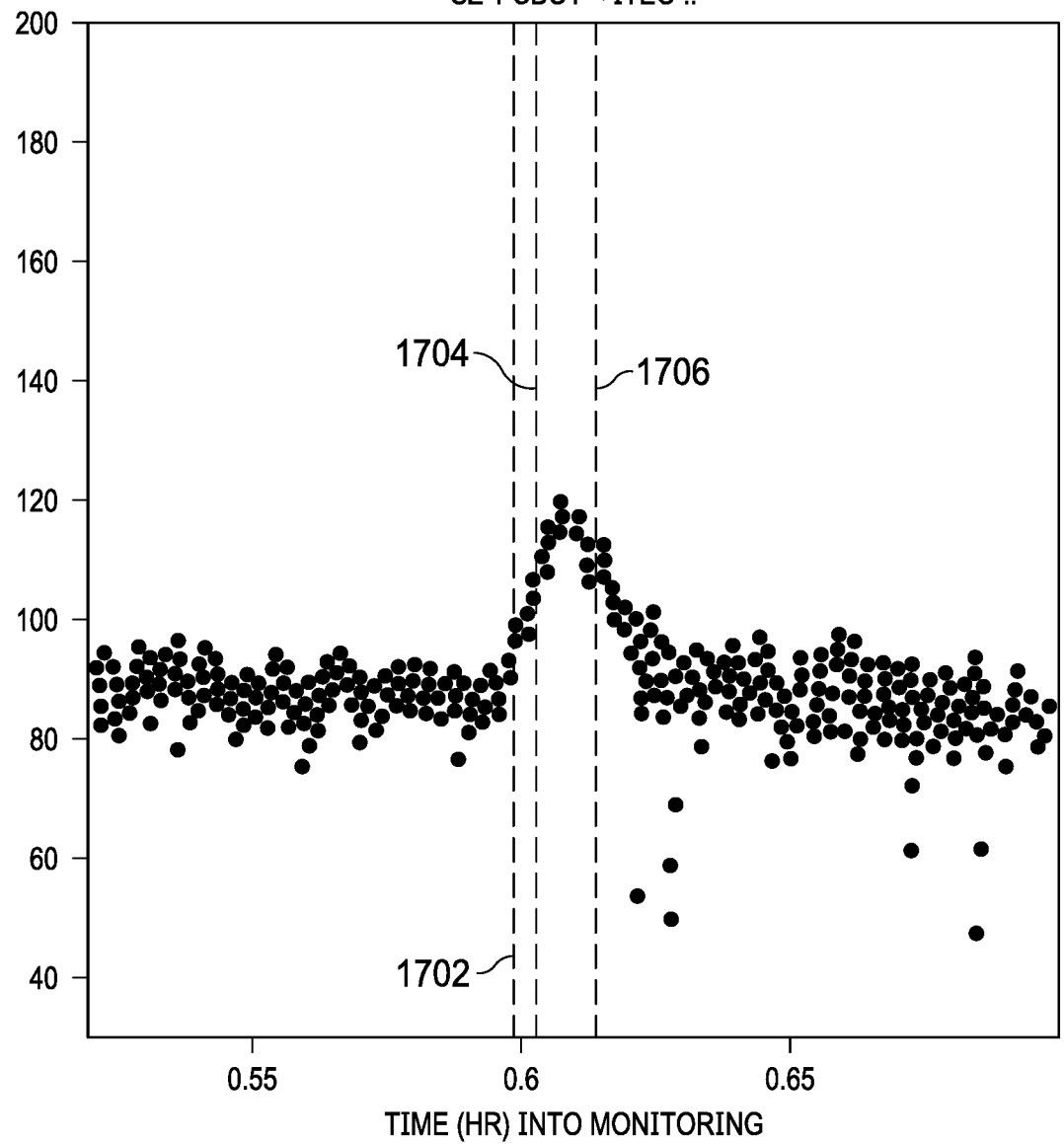
FIG. 17 is a graph relating to the automated detection and control of ictal and peri-ictal chronotropic instability, according to one embodiment.
Figure 18:
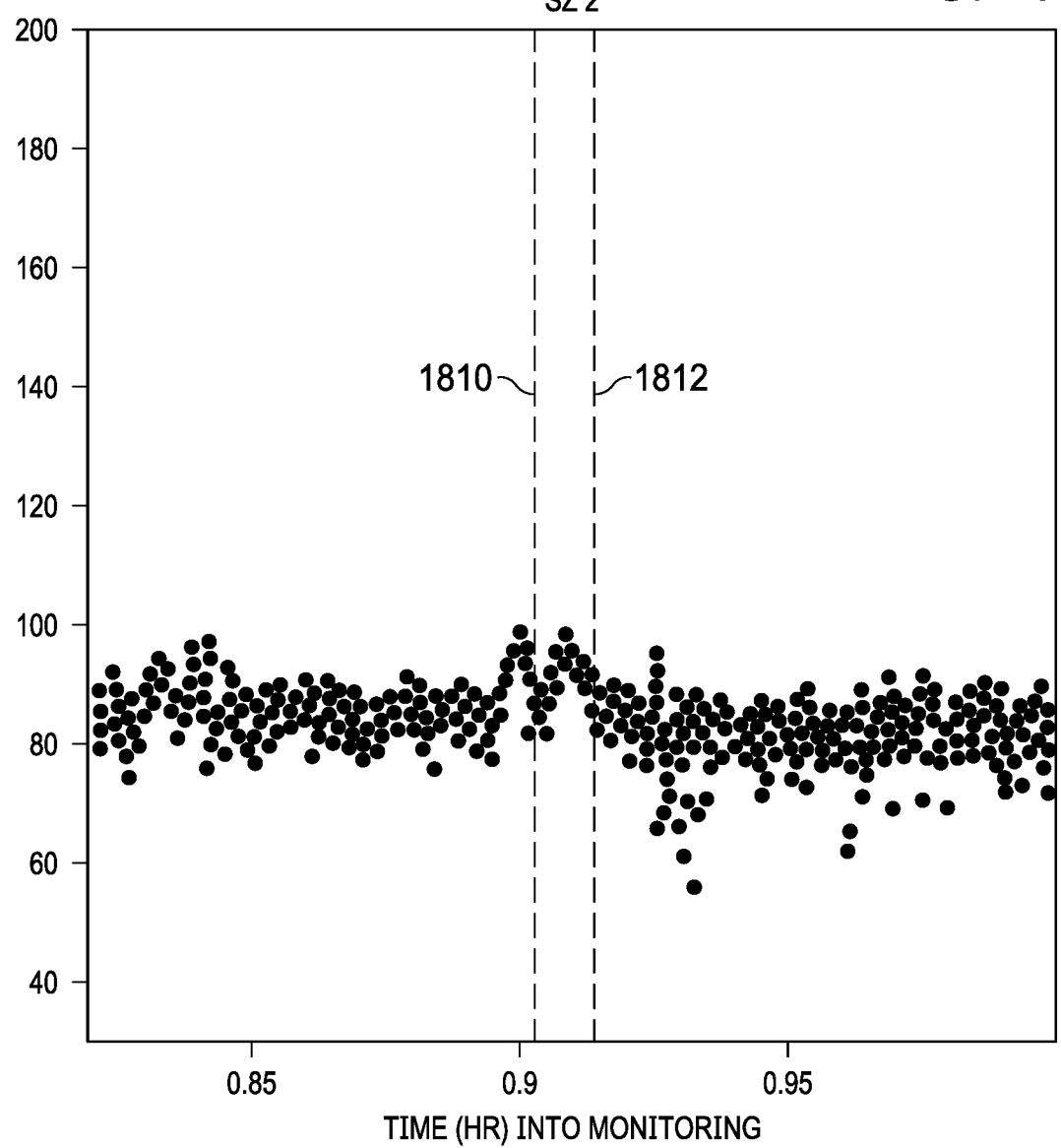
FIG. 18 is a graph relating to the automated detection and control of ictal and peri-ictal chronotropic instability, according to one embodiment.

In FIG. 17, a graph shows monotonic increase and decrease in heart rate. In FIG. 17, a first triggering event, a first warning event, and/or a first therapy event 1702 are shown. Further, a second triggering event 1704, a second warning event, and/or a second therapy event 1704 are shown. In addition, an Nth triggering event, an Nth warning event, and/or an Nth therapy event 1706 are shown. In FIG. 18, the heart rate of the patient increases which is followed by a decrease in heart rate, then an increase heart rate and a final decrease in heart rate. In this example, the first drop in heart rate crossed downwardly the detection threshold which would have temporarily disabled the warning system and the delivery of the therapy. While the first peak was not temporally correlated with paroxysmal activity on any of the intra-cranial electrodes used in this patient, it is likely that the first increase in heart rate was caused by epileptic discharges from a brain site that was not being investigated. In this example, the x-axis is time in hours and the y-axis is heart beats per minute. In this example, an electrographic onset in the brain 1810 is shown and an electrographic termination in the brain 1812 is shown.

Figure 19:
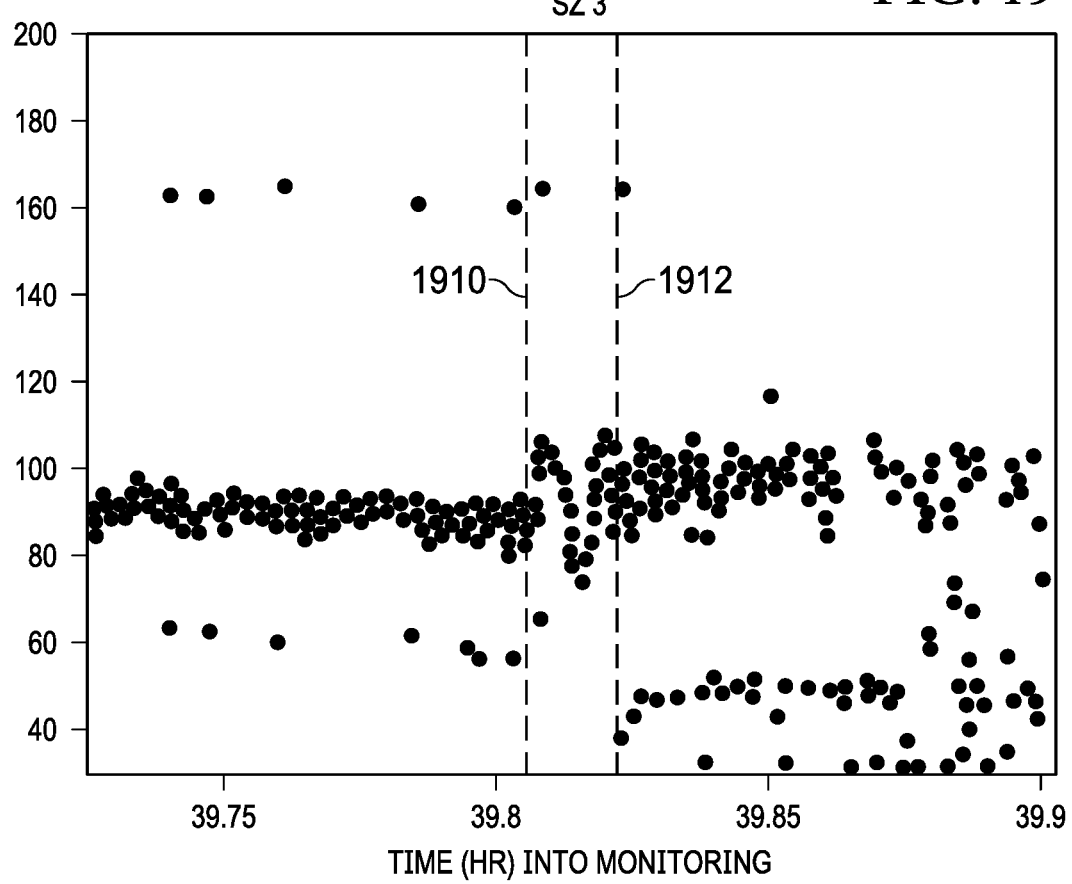
FIG. 19 is a graph relating to the automated detection and control of ictal and peri-ictal chronotropic instability, according to one embodiment.

In FIG. 19, a change in ictal heart rate is shown. In this example, the drop in heart rate during the seizure, is even more prominent that the one depicted in FIGS. 17-18, as it is below the interictal baseline. It should be noted that the oscillations in heart rate during the post-ictal period are indicative of cardiac instability. In this example, a seizure onset point 1910 and a seizure termination point 1912 are shown.

Figure 20:
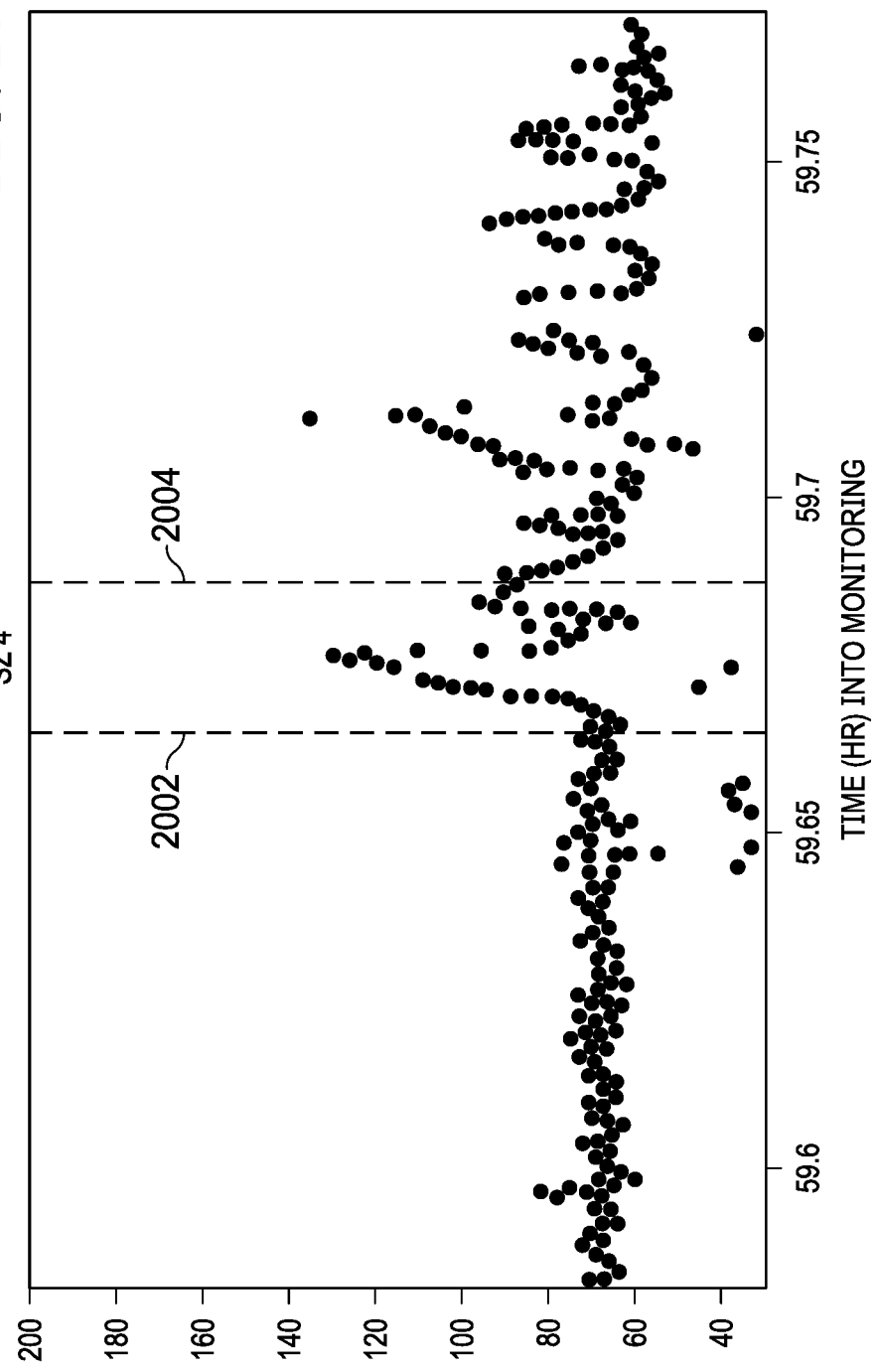
FIG. 20 is a graph relating to the automated detection and control of ictal and peri-ictal chronotropic instability, according to one embodiment.

In FIG. 20, large amplitude tachycardia cycles occurring quasi-periodically after termination of paroxysmal activity recorded with intra-cranial electrodes. While the mechanisms responsible for these oscillations are unknown, the probability that they are epileptic in nature cannot be excluded, since electrographic and imaging data used to guide intra-cranial electrode placement pointed to the existence of only one epileptogenic site.

Figure 21:
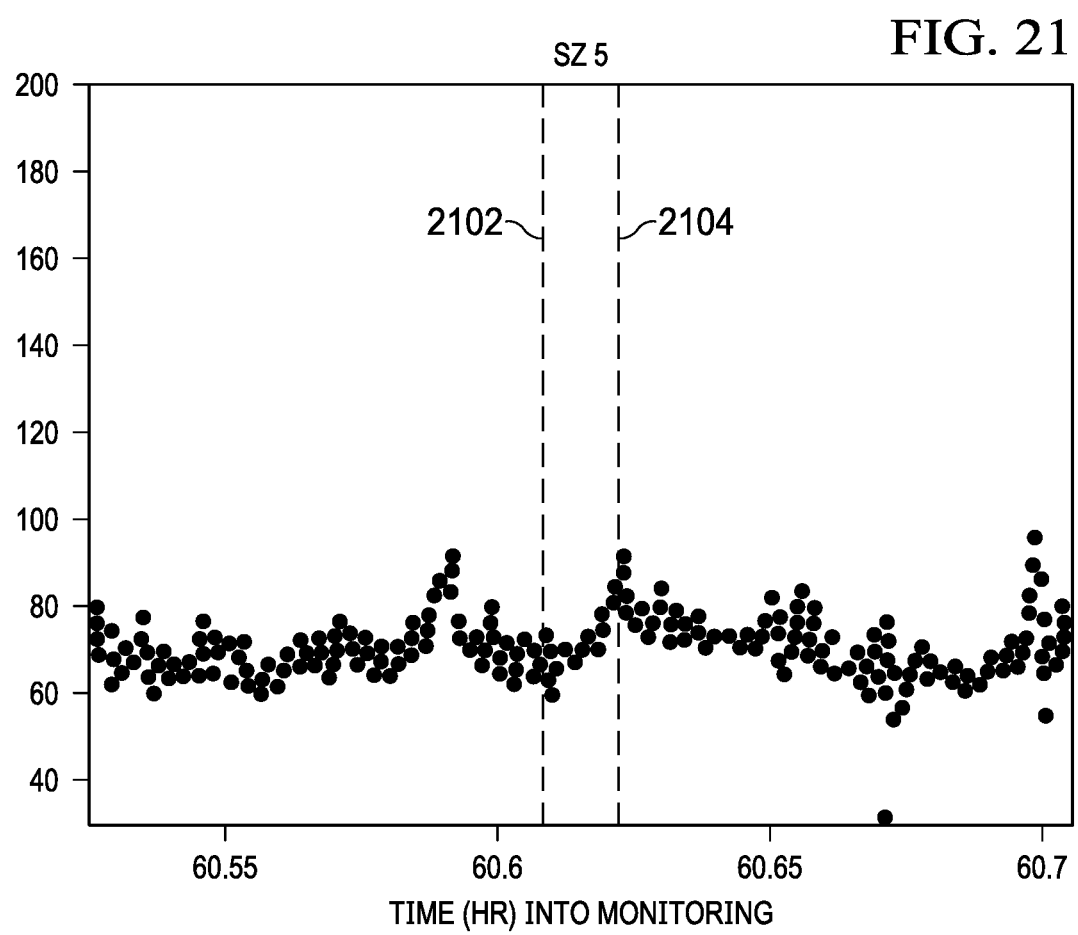
FIG. 21 is a graph relating to the automated detection and control of ictal and peri-ictal chronotropic instability, according to one embodiment.

In FIG. 21, small amplitude continuous quasi-periodic oscillations preceding and following a seizure recorded with intra-cranial electrodes (same patient as FIG. 20). In various embodiments, ictal and peri-ictal cardiac instability are shown. The mechanisms leading to SUDEP have not been elucidated, in part due to the inability to record data during the critical events that culminate in cardiac fibrillation or in standstill (or in respiratory arrest). In this example, a first triggering event, a first warning event, and/or a first therapy event 2102 are shown. Further, an Nth triggering event, an Nth warning event, and/or an Nth therapy event 2104 are shown.

The data obtained in intractable epileptics undergoing epilepsy surgery evaluation not only supports a cardiac mechanism (of course, not at the exclusion of catastrophic respiratory failure) but more specifically points to chronotropic instability as backdrop against which, lethal arrhythmias or cardiac standstill may ensue. Moreover, the instability is not restricted to the ictal period but, in certain cases, precedes and/or follows it for several minutes. FIGS. 17-21 illustrate the spectrum of instability in intractable epileptics. This phenomenon is referred herein to as Ictal and Pre-Ictal Chronotropic Instability.

The challenges that for accurate quantification and delivery of efficacious therapies, ictal chronotropic instability poses, were addressed and strategies to manage them are outlined. Here, the attention is focused on Ictal and Pre-Ictal Chronotropic Instability, a more prolonged and serious pathological phenomenon in intractable epileptics and on the vital issues of cardio-protection.

The aim of this disclosure is to contingently and adaptively dampen based on the slope, amplitude, duration and "direction" (positive or negative chronotropic and its magnitude relative to an adaptive baseline/reference heart rate) the heart oscillations present before, during or after epileptic seizures.

While several embodiments may be envisioned, on embodiment (for efficacy, practicality and cost-effectiveness) is to electrically stimulate/activate the trunk or a branch of the right vagus nerve in the case of elevations in heart (to reduce the heart rate, when there are more than 2 consecutive oscillations/cycles or 1 that is large and prolonged. The intensity and duration of stimulation as well as other parameters are determined by the slope, amplitude and duration of the oscillations, while ensuring adequate blood perfusion to all organs. In the case of negative chronotropic effects (decreases in heart rate) the trunk or a branch of the right vagus nerve may be "blocked" using certain electrical stimulation techniques or through cooling; the effect of this intervention is to increase heart rate.

In one embodiment, the "height" of the oscillation is the only feature considered. While obviously important, this embodiment does not take into consideration a possibly more important feature: the rate at which the oscillation occurs: the consequences of waiting to intervene until an oscillation reaches a certain height (e.g., 120 bpm) are different if it takes, 30 seconds for the heart rate to reach the value than if it takes 2 seconds to reach the value. Estimating the rate of change of the heart rate, provides life-saving information. Another aspect is the inter-maxima or inter-minima interval between oscillations. Having heart rate oscillation occur every 2-3 seconds is much more serious than every 1-2 hours. In one example, one benefit may be that the window to act is lengthened which can save lives. In one embodiment, a system for treating a medical condition in a patient includes: a sensor for sensing at least one body data stream; a heart rate unit which determines a heart rate and a heart rate oscillation of the patient based on the at least one body data stream; and a logic unit which compares via one or more processors a monitored value which is determined based on one or more data points relating to the heart rate and to the heart rate oscillation to a threshold value, the logic unit determines a triggering event based on the comparison where the one or more processors initiate one or more actions to change the heart rate of the patient based on the determination of the triggering event.

In another example, the system includes at least one electrode coupled to a vagus nerve of the patient and a programmable electrical signal generator. Further, the one or more processors may increase a sympathetic tone to increase the heart rate of the patient. In another example, the one or more processors may decrease a parasympathetic tone to increase the heart rate of the patient. In another example, the one or more processors may decrease a sympathetic tone to decrease the heart rate of the patient. Further, the one or more processors may increase a parasympathetic tone to decrease the heart rate of the patient. In addition, the system may include a seizure detection unit which analyzes the at least one body data stream to determine an epileptic seizure status. The system may include at least one electrode coupled to a vagus nerve of the patient and a programmable electrical signal generator where the one or more processors apply an electrical signal to the vagus nerve of the patient based on a determination that a seizure is characterized by a decrease in the heart rate of the patient and where the electrical signal is applied to block action potential conduction on the vagus nerve. In addition, the heart unit may determine an inter-maxima interval and an inter-minima interval between a first oscillation and a second oscillation. Further, the logic unit may compare the inter-maxima interval and the inter-minima interval to an interval threshold. In addition, the one or more processors may initiate one or more actions based on the interval threshold being reached.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below. In addition, all examples, embodiments, and/or elements may be combined in any manner that are disclosed in this document. In other words, an element from a first example (paragraph [0088]) can be combined with any other element, such as, a second element from an Nth example (paragraph [0163]). For brevity, all these examples are not written out but are part of this document.

Embodiments disclosed herein provide for detecting an epileptic seizure based upon an ictal component or content of a body signal value of a patient. The ictal component may be determined based upon the body signal value, a reference value of the body signal, and a work level of the patient. One or more body signals of a patient may be acquired in a time series, from which a current body index value is determined and a work level of the patient may be determined based on the body index value relative to one of a body index reference value, a temporal fiducial or an activity level. The ictal component of the current body index value may be determined based upon the work level, as well as the current body signal value and the reference value. The magnitude of the ictal component may then be used to determine whether or not an epileptic seizure has occurred. If a seizure has occurred, a seizure detection may be issued. In response to issuing the seizure detection, a responsive action may be taken. The responsive action may include providing a warning, logging the epileptic event, providing a therapy, and/or providing a warning.

More information regarding automated assessments of disease states, comorbidities, and the like may be found in other patent applications assigned to Flint Hills Scientific, LLC or Cyberonics, Inc., such as, U.S. Ser. No. 12/816,348, filed Jun. 15, 2010; and U.S. Ser. No. 12/816,357, filed Jun. 15, 2010. Each of the patent applications identified in this paragraph is hereby incorporated herein by reference.

More information regarding automated assessments of therapies may be found in other patent applications assigned to Flint Hills Scientific, LLC or Cyberonics, Inc., such as, U.S. Ser. No. 12/729,093, filed Mar. 22, 2010; U.S. Ser. No. 13/280,178, filed Oct. 24, 2011; U.S. Ser. No. 13/308,913, filed Dec. 1, 2011; and U.S. Ser. No. 13/472,365, filed May 15, 2012. Each of the patent applications identified in this paragraph is hereby incorporated herein by reference.

More information regarding the detection of abnormal brain activity, such as seizures, identifying brain locations susceptible to spread of the abnormal brain activity, and treating the susceptible brain locations may be found in other patent applications assigned to Flint Hills Scientific, L.L.C., or Cyberonics, Inc., such as, U.S. Ser. No. 13/449,166, filed Apr. 17, 2012. Any patent application identified in this paragraph is hereby incorporated herein by reference.

More information regarding the detection of brain or body activity using sensors implanted in proximity to the base of the skull may be found in other patent applications assigned to Flint Hills Scientific, L.L.C., or Cyberonics, Inc., such as, U.S. Ser. No. 13/678,339, filed Nov. 15, 2012. Any patent application identified in this paragraph is hereby incorporated herein by reference.

Over the past several decades, medical devices providing electrical therapies to treat a number of medical conditions have been developed and approved. Examples of these therapies include pacing and defibrillation of the heart, electrical stimulation of the spinal cord to treat intractable pain, and stimulation of the vagus nerve to treat epilepsy and depression, among others. In many cases, the patient must be gradually acclimated to the exogenous electrical therapy, and the therapy is gradually increased from a very low dosage to a higher, therapeutically-effective dosage. Heretofore, this process has been performed manually. For example, an epilepsy patient being treated with vagus nerve stimulation may initially be provided with no stimulation for the two weeks following implantation of the device to allow the surgical incision and trauma to heal, after which the physician (or other healthcare provider) may manually program the device to provide a relative low dosage of pulsed electrical therapy, characterized by a current magnitude of 0.1 milliamps (mA)), a pulse width of 0.25 milliseconds, a pulse frequency of 30 Hz, an on-time of 30 seconds, and an off-time of 300 seconds. This initial therapy dosage level may be too low to provide a therapeutic benefit to the patient. Accordingly, the physician may thereafter manually reprogram the patient every 2-4 weeks, to gradually increase the current magnitude in a number of steps to reach a therapeutically-effective, safe, and tolerable dosage level, e.g., from 0.1 mA to 0.5 mA, then to 0.75 mA, 1.0 mA, 1.25 mA, 1.5 mA, 1.75 mA, and finally to 2.0 mA. Such adjustments, referred to herein as therapy titration as the electrical therapy is gradually increased to therapeutically-effective dosage levels, require the patient to make additional office visits at significant cost (in money and time) to both the patient and the treating healthcare provider. The manual titration process may in many cases delay the patient receiving a therapeutic benefit for weeks or months.

Embodiments disclosed herein provide for programming a medical device to implement an electrical therapy following implantation of the device, and to automatically titrate at least one parameter defining the electrical therapy from a first value to a target value. By automatically titrating one or more parameters of the electrical therapy, the patient may be more effectively, more quickly, and more cost-effectively acclimated to the therapy, and may be titrated to a therapeutically-effective dosage of the electrical therapy faster and with less pain and discomfort. The titration may involve increasing or decreasing electrical therapy parameters, and may comprise adjusting one or more parameters (e.g., current (or voltage) amplitude, frequency, pulse width, on-time, off-time, and/or duty cycle) defining the therapy by incremental changes from the first value to the target value. The adjustments to the one or more parameters may be periodic, aperiodic, or contingent. In one embodiment, contingent adjustment refers to an adjustment that is automatically initiated, but which requires a user to respond to a prompt before the adjustment is implemented in the therapy. In one embodiment, changes may be manual or automated or in response to input from a person. In some embodiments, two or more parameters may be automatically titrated from respective first values to respective target values. In some embodiments, undesirable side effects may be detected and used to return one or more automatically titrated parameters to a prior value before resuming the titration to the target value. By using side effects (such as pain, discomfort, or changes in one or more body indices such as heart rate) to indicate a lack of tolerance and/or safety of a particular titration step, titration may be automatically adjusted to rapidly, safely and comfortably titrate the patient to therapeutically-effective, tolerable, and safe therapy dosage levels.

In some embodiments, the medical device may be programmed to establish a first target value for a first electrical therapy parameter. The first electrical therapy parameter may be one or more of the previously noted parameters defining or characterizing the electrical therapy. In some embodiments, the medical device may be programmed to establish a first target value for more than a first electrical therapy parameter, e.g., the device may be programmed to establish first values and/or target values for a first, a second, a third, and an nth electrical therapy parameter. The automated titration of multiple parameters may be sequential, simultaneous, and/or partially overlapping, and may be tailored to address one or more of efficacy, safety, and tolerability, which may be separately impacted by changes associated with each of one or more of the individual parameters.

Embodiments of the invention also involve programming at least one titration parameter for automatically adjusting the first (and/or second, third, etc.) electrical therapy parameter from the first value to the target value. The titration parameter may be selected from a titration time period, a titration step interval, a titration step magnitude, and/or a titration rate. The titration time period is the time period in which an electrical parameter is to be titrated from the initial value to the target value, e.g., 2 weeks. In some embodiments, different titration time periods may be set for each of a plurality of parameters characterizing the electrical signal, e.g., the current may be titrated to the target value over a period of 2 weeks, while the pulse amplitude may be titrated to the target value over one week. The titration step interval is a time interval at which at least one titration adjustment step is made. In some embodiments, all of the titration steps are made at the same titration step interval, while in other embodiments, only the initial titration step interval is provided, and subsequent step intervals are determined based upon a titration function describing how the titration is to occur (e.g., uniformly or non-uniformly). The titration step magnitude is the magnitude of the change made to at least one adjustment of an electrical parameter. For example, current adjustments may be made with a titration step magnitude of 0.1 mA, with each new automatic current adjustment comprising a 0.1 mA increase over the prior value. In some embodiments, titration step magnitudes may be specified for a plurality of electrical parameters (e.g., a current titration step magnitude of 0.1 mA, and a pulse width step magnitude of 0.05 msec). In some embodiments, all of the titration steps for a given electrical parameter are made at the same titration step magnitude, while in other embodiments, only the initial titration step interval is provided, and subsequent step intervals are determined based upon a titration function describing how the titration is to occur (e.g., uniformly or non-uniformly). In one embodiment, the automated titration process may occur at various different scales as a function of titration rate. By way of a first example, the rate at which the target value is reached or approached may be equivalent or comparable to the titration step magnitude divided by the titration time interval. By way of a second example, the rate at which a parameter is changed at a step of the titration.

The titration adjustments may be made according to a titration function describing how the titration steps are to be implemented. In one embodiment, the titration function may be a linear stepwise function in which uniform titration step magnitude changes are made at uniform titration step intervals. In other embodiments, the titration function may be implemented as a non-linear stepwise function, a stepwise approximation of a polynomial, a continuous function, or a mixed stepwise and continuous function. In an example of a non-linear function, one or more of the titration step interval and the titration step magnitude may be non-linear, and may be, for example, a parabolic or higher-order polynomial.

Non-limiting examples of various titration functions are shown in FIGS. 11-12. FIG. 11 shows that various parameters may vary according to different functions, e.g., for the functions shown in solid lines, the current (in mA) may have a convex shape over the course of the titration, and the frequency (in Hz) may have a concave shape. For another example, for the functions shown in dashed lines, both current and frequency may have the same general shape (e.g., concave) over the course of titration, but one may reach a final value faster than the other. FIG. 12 shows an example of a parabolic function, e.g., $y=-x2$ for $x=[-5, 0]$.

In some embodiments, a titration function may be self-similar or fractal (i.e., each step may have the same shape as the overall function). Also, although FIGS. 11-12 show smooth parabolic functions, a parabola (or other smooth shape) may be approximated by a series of relatively small steps. As the person of ordinary skill in the art, having the benefit of the present disclosure, will understand, other functions than those shown in FIGS. 11-12 may be used.

The titration function may be programmably selected by a healthcare provider or may be a predetermined function such as a linear function. In some embodiments, the titration function may further be influenced by additional factors such as the patient's age, health status, gender, the severity of the disorder being treated (e.g., seizure type, frequency and severity in patients with epilepsy), the patient's tolerance to adverse events, the patient's tolerance to pain, among other relevant factors.

In some embodiments, the titration function may be interrupted or modified by the occurrence of one or more events, such as one or more side effects, patient tolerance, patient safety, or patient disease state, among others. For example, the titration function as initially programmed may be automatically adjusted to accelerate, slow down, or temporarily suspend or reverse the titration process based upon one or more body signal(s). The one or more body signals may be analyzed by the medical device and an automated adjustment of the titration process may be performed by, e.g., lowering a parameter value that results in undesired side effects such as discomfort, pain, respiratory effects (e.g., dyspnea), voice alteration, changes in heart rate, etc., to allow the patient additional time to accommodate to the previous stimulation dosage before resuming the titration process. In addition, feedback from external sources, e.g., manual input by the patient or a caregiver may, also be used to reverse, slow down, or accelerate the titrating of the therapy.

The titration of the therapy may be implemented by initiating the electrical therapy with the one or more parameters to be titrated set at their respective initial values. The therapy may thereafter be titrated by automatically adjusting the one or more electrical therapy parameters based upon the programmed one or more titration parameters (e.g., the titration time period, titration step period, titration step magnitude, and/or titration rate) and the titration function.

As an example, a health care provider may program a medical device to provide an electrical therapy in which a first parameter such as electrical pulse current increases from an initial value of 0 mA to a target value of 2.0 mA. The therapy may be automatically titrated from the initial value to the target value based on the titration time period according to the titration function. In one embodiment, various steps between the initial value and the target value may be made such that the titration process causes the therapy signal to have a specific value at each of these intermediate steps until the target value is achieved. That is, the automatic titration feature may "ramp up" a parameter defining the electrical therapy by increasing the parameter in small increments over a programmed titration time period. In a particular embodiment, the incremental increase may be implemented once each day over a programmed time period selected from one day to 60 days, and may include two days, three days, four days, five days, one week, ten days, two weeks, three weeks, four weeks, or any other period from 2-60 days. In one embodiment, titration may be adjusted in view of one or more of patient input, body signals, or brain evoked responses.

In some embodiments, a user may not need to explicitly program a titration time period. Instead, the user may program a titration step magnitude and a titration step interval. According to such embodiments, the electrical therapy is initiated with the therapy parameter at a first value, and the value is iteratively increased by the titration step magnitude after the lapse of each titration step interval. For example, an electrical therapy used to provide vagus nerve stimulation therapy to a patient may be increased by 0.1 mA (or other titration step magnitude) each day (or other titration step interval) until the target value is reached. The patient, physician or healthcare provider may be sent a message when the target dosage is reached according to some embodiments.

In other embodiments, the titration of the therapy may be automatically or manually altered. For example, in some embodiments, body data from the patient may be used to evaluate one or more effects of the automatic therapy titration. Based on the one or more effects of the therapy, the titration of the therapy may be altered. In another embodiment, if efficacy is detected (as determined, e.g., from body data) during the titration process, then further titrating of the therapy may be suspended. Alternatively, if side effects of the therapy are found, the titration may be suspended or reversed until further interaction with a healthcare provider. In some embodiments, the titration process may be reversed upon a first detection of a side effect, and after resuming the titration process, detection of a second or a third side effect may result in suspension of further automatic titration of the electrical therapy until the patient's physician programs the medical device to resume the titration, in which case an alert may be sent to the physician or other caregiver. In a further embodiment, if no adverse effects of the therapy are noted, the titration of the therapy may be accelerated to reach the target value sooner than a programmed titration time period. The adjustment of the titrating process may be an automated iterative process, wherein adjustments to the titrating steps may be altered based upon body data analysis during each delivery of therapy.

Figure 22:
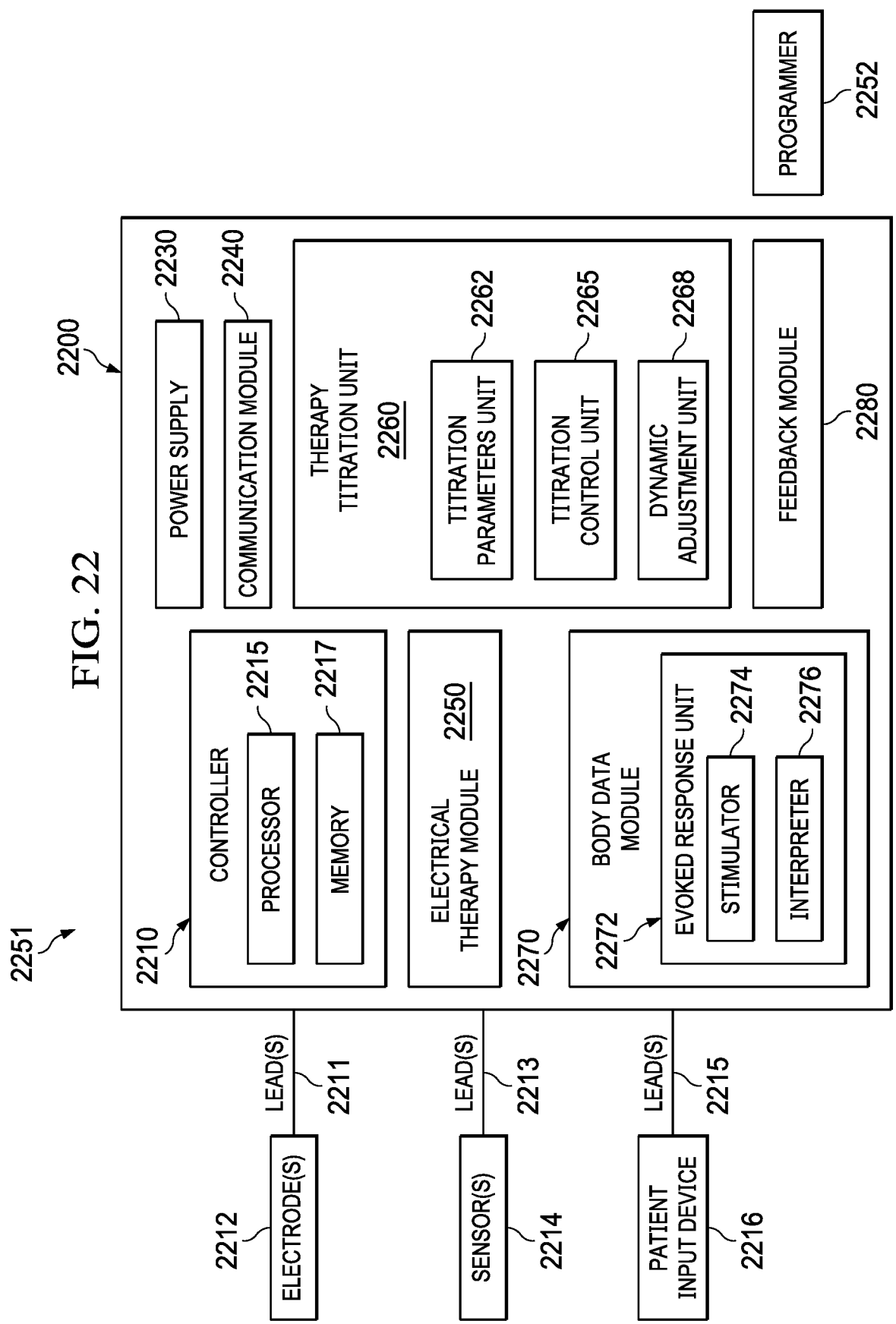
FIG. 22 shows a schematic diagram of a medical device system, in accordance with some embodiments of the present disclosure.

FIG. 22 shows a stylized block diagram representation of a medical device system, according to some embodiments of the present disclosure. The medical device system 2251 may comprise a medical device 2200, electrode(s) 2212, lead(s) 2211 coupling the electrode(s) 2212 to the medical device 2200, sensor(s) 2214, and lead(s) 2213 coupling the sensor(s) 2214 to the medical device 2200. The electrode(s) 2212 may be configured to deliver an electrical therapy defined by a plurality of parameters to a patient. The sensor(s) 2214 may be configured to collect body data relating to any body data stream of the patient, which may include as non-limiting examples one or more of the patient's cardiac signal (e.g., heart rate, heart rate variability), respiratory signal (e.g., respiratory rate, end tidal volume, respiratory rate variability), blood oxygen saturation, blood oxygen saturation variability, discomfort level, gastro-intestinal activity, shortness of breath, or vocal cord function. The medical device system 2251 includes a programmer 2252 which may be used to program the medical device 2200, which in some embodiments is an implantable medical device (IMD), a partially implantable medical device, or a portable external medical device with one or more parameters characterizing the electrical therapy and one or more titration parameters to automatically titrate the one or more parameters from a first value to a target value. In some embodiments, a patient (manual) input device 2216 may be coupled to the medical device 2200 by lead(s) 2215 or by a wireless coupling (not shown), and may be used to provide an input (which may be a manual input or an automatic input from, e.g., an accelerometer other sensing device incorporated in the patient input device 2216) from the patient.

Various components of the medical device 2200, such as controller 2210, processor 2215, memory 2217, power supply 2230, and communication unit 2240 have been described in other patent applications assigned to Flint Hills Scientific, LLC or Cyberonics, Inc., such as, U.S. Ser. No. 12/770,562, filed Apr. 29, 2010; U.S. Ser. No. 12/771,727, filed Apr. 30, 2010; U.S. Ser. No. 12/771,783, filed Apr. 30, 2010; U.S. Ser. No. 12/884,051, filed Sep. 16, 2010; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012; U.S. Ser. No. 12/896,525, filed Oct. 1, 2010, now U.S. Pat. No. 8,337,404, issued Dec. 25, 2012; U.S. Ser. No. 13/098,262, filed Apr. 29, 2011; U.S. Ser. No. 13/288,886, filed Nov. 3, 2011; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

The medical device 2200 may comprise an electrical therapy module 2250 to generate an electrical therapy signal that may be provided as an electrical therapy to a target body structure such as a cranial nerve or brain tissue via electrodes 2212. The electrical therapy signal may be characterized by a plurality of parameters, e.g., an amplitude, a pulse width, a pulse frequency, a signal on-time, or a signal off-time, among others. The electrical therapy module 2250 may be configured to deliver an electrical therapy signal having a low initial or first value of one or more parameters upon initiation of the treatment regimen. The treatment regimen may be initiated after implantation of electrode(s) 2212, medical device 2200, or other components of the medical device system 2251. Alternatively or in addition, the therapy may be initiated as part of a "reboot" or "reset" of a previously suspended therapy. In one embodiment, the electrical therapy signal may be programmed along with one or more titration parameters to titrate an electrical current setting for electrical pulses applied to a target structure from a first value (e.g., 0 mA or 0.1 mA) to a target value for providing therapy (e.g., 2.5 mA).

The treatment regimen may be configured to treat epilepsy, depression, pain, congestive heart failure, traumatic brain injury, or obesity, among other ailments known to persons of skill in the art to be amenable to treatment by electrical therapy of the body, e.g., of neural structures, e.g., of the brain, spinal cord, or a cranial nerve, e.g., the vagus nerve.

Figure 23:
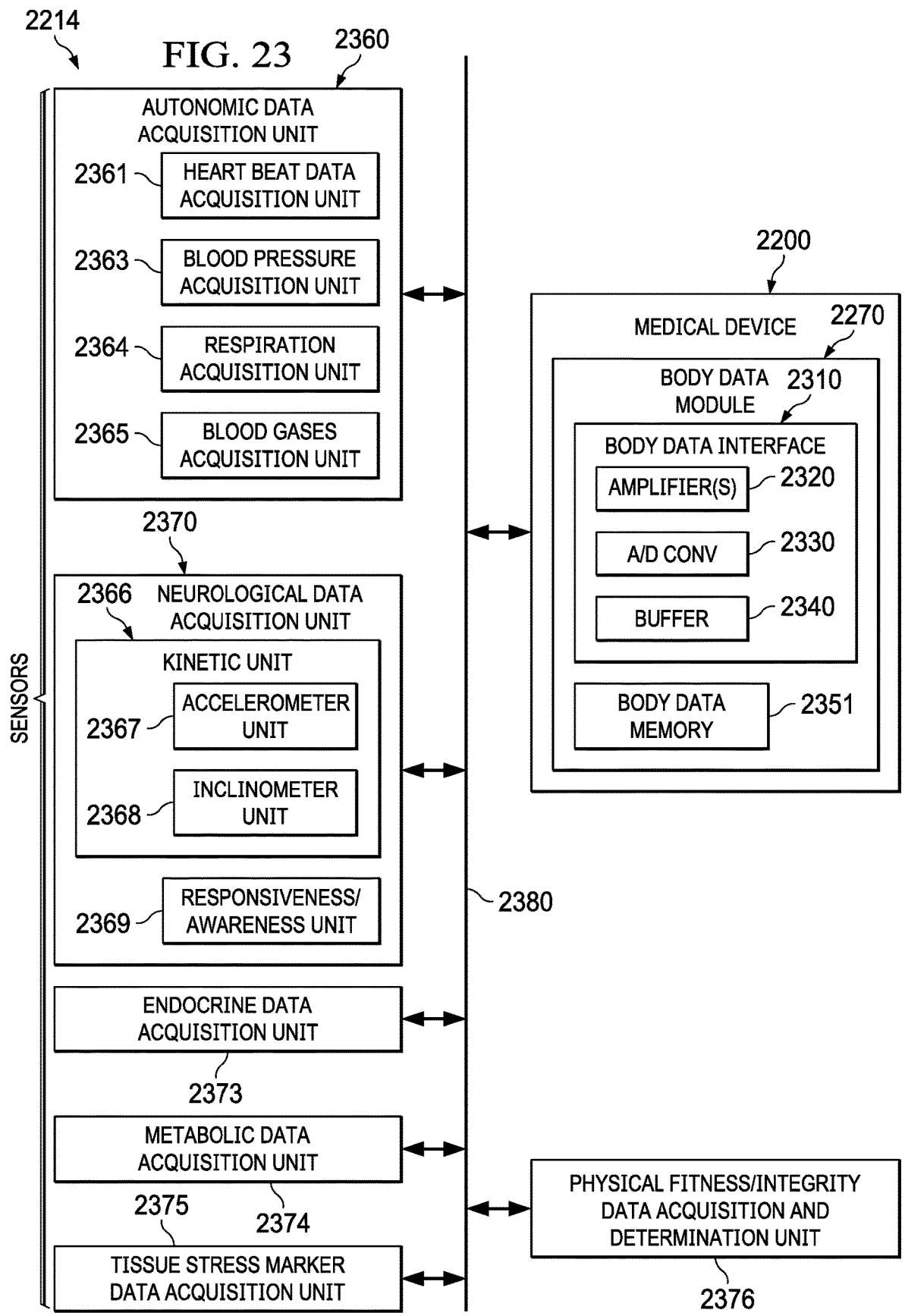
FIG. 23 shows a schematic diagram of data acquisition components of a medical device system, in accordance with some embodiments of the present disclosure.

The medical device 2200 may also comprise a body data module 2270. The body data module 2270 is capable of acquiring signal(s) relating to a patient's body data, processing and analyzing the signals to assess the effects (beneficial or deleterious) of the therapy on the patient. The body data module 2270 may also be configured to determine one of a time series of body data values or body index values based upon the time series. Such a time series of body index values may comprise at least one of an instantaneous heart rate (HR), a heart rate variability (HRV), an instantaneous respiratory rate (RR), an instantaneous blood pressure (BP), an instantaneous blood oxygen saturation (02S) value, a blood oxygen saturation variability, or vocal cord function, among others. Body data module 2270 is shown in FIG. 23 and accompanying description below.

In one embodiment, the body data module 2270 may comprise an evoked response unit 2272. The evoked response unit 2272 may be configured to apply a signal to a body tissue and determine what response, if any, is evoked in the tissue by the signal. For example, the evoked response unit 2272 may comprise a stimulator 2274 configured to apply a signal expected to evoke a response, and an interpreter 2276 configured to determine what response, if any, was evoked by the signal.

In one embodiment, the evoked response unit 2272 may be a vagus evoked response unit, i.e., a unit configured to acquire data from the vagus nerve relating to responses evoked on a body tissue (e.g., a vagus nerve, a heart, or a brain or a region thereof) by an electrical stimulation or to acquire EEG or ECoG data. Alternatively or in addition, the evoked response unit 2272 may be a voice evoked response unit, i.e., a unit configured to acquire data from the patient's body relating to responses evoked on the vocal cords and/or other vocal apparatus by an electrical stimulation or other therapy modality. For example, vagus nerve stimulation may interfere with a patient's vocal cord function, e.g., by rendering the voice hoarse or husky, and an evoked response unit 2272 according to this embodiment may gather and analyze data relating to such evoked responses.

The medical device 2200 may comprise a therapy titration module 2260 configured to titrate one or more electrical therapy parameters to a target value according to a titration function. The titration may involve decreasing the therapy parameters at certain times in response to the occurrence of an adverse event. (As used herein, "adverse event" refers to side effects and/or other undesirable events). In some embodiments, the titration is continued until one or more of a tolerable, a safe, an efficacious, and/or a target electrical parameter value is achieved. In other words, the target dosage may be either tolerable, efficacious or both. In some embodiments, the programmed target value for a titration parameter may be altered to a lower or higher value based upon one or more of a measured level of efficacy (or lack of efficacy) or the emergence of side effects.

The titration module 2260 may comprise a titration control unit 2265 configured to determine and implement the titration function. In some embodiments, the titration function may be determined by looking up information from a titration parameter module 2262. In some embodiments, titration parameters for performing the titration may also be programmed into the medical device 2200 from an external programming device 2252 by a physician, and stored into memory. The titration parameters may include one or more of the titration time period, the titration step interval, the titration step magnitude, the titration rate, and one or more other parameters defining the titration function.

Figure 24:
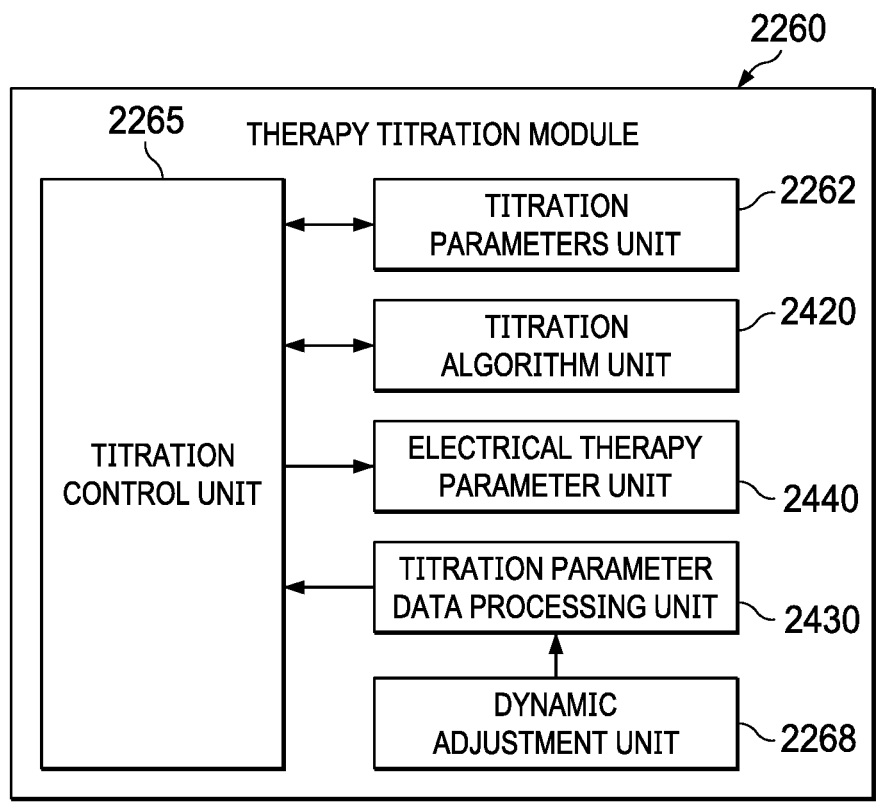
FIG. 24 shows a schematic diagram of a therapy titration module, according to some embodiments of the present disclosure.

As shown in FIG. 24, in some embodiments, the therapy titration module 2260 may comprise a titration parameter data processing unit 2430 to process data to implement the titration of the one or more electrical therapy parameters; a titration algorithm unit 2420 for providing instructions relating to titrating of one or more electrical parameters of the electrical therapy signal; the titration control unit 2265 to receive data from at least one of the titration parameter data processing unit 2430, the titration algorithm unit 2420, and the titration parameters unit 2262. Therapy titration unit 2260 may further comprise an electrical therapy parameter unit 2440, operatively coupled to the titration control unit 2265, to provide one or more values of the electrical therapy parameters to be titrated to the electrical therapy module 2250, such as one or more initial (or first) and target values for the electrical parameters to be titrated, as well as values for other parameter that are not intended to be titrated. In some embodiments, the titration parameter data processing unit 2430 may be configured to receive data from a dynamic adjustment unit 2268, described below. The titration parameter data processing unit 2430 may be capable of processing data to determine a titration protocol or function. The titration function may be defined by one or more parameters that determine how the electrical therapy parameters are to be titrated to the target value and may determine one or more titration periods, titration step intervals, titration step magnitudes, and/or titration step rates.

The therapy titration module 2260 may further comprise a dynamic adjustment unit 2268 configured to adjust one or more electrical parameters and/or titration parameters based on the feedback data from, e.g., sensors 2214 and/or feedback module 2280. The dynamic adjustment unit 2268 may accelerate, slow down, suspend, or resume the programmed titration process according to body data received from the patient. In some embodiments, the dynamic adjustment unit 2268 may be used to determine one or more of a measure of efficacy of the therapy (to identify and/or quantify whether or not the electrical therapy is efficacious) or a side effect of the therapy, and to use such measure of efficacy, lack of efficacy, or side effects, to cause titration control unit 2265 to accelerate, interrupt or suspend, reduce, or resume the therapy titration process. In some embodiments, the dynamic adjustment unit 2268 may cause titration control unit 2265 to adjust the one or more electrical therapy parameters to slow the titration of the one or more electrical therapy parameters to their respective target values, while in others the titration function may be adjusted to speed up the titration to the target value. For example, if the feedback data indicates that the patient suffered an adverse reaction to the electrical therapy, the dynamic adjustment unit 2268 may increase the titration step interval to slow titration of the electrical therapy parameter(s), or it may reduce one or more electrical therapy parameters being titrated to the most recent value not associated with an adverse effect. Doing so may eliminate or reduce a side effect, and allow the patient additional time to accommodate to a particular titration step. As another example, if the feedback data indicates that the patient did not suffer an adverse reaction to the treatment and the treatment lacks sufficient efficacy, the dynamic adjustment unit 2268 may reduce a titration step interval to prompt a faster titration of the therapy. In this manner, the dynamic adjustment unit 2268 and the therapy titration module 160 are capable of improving safety and efficacy of therapy.

Figure 25:
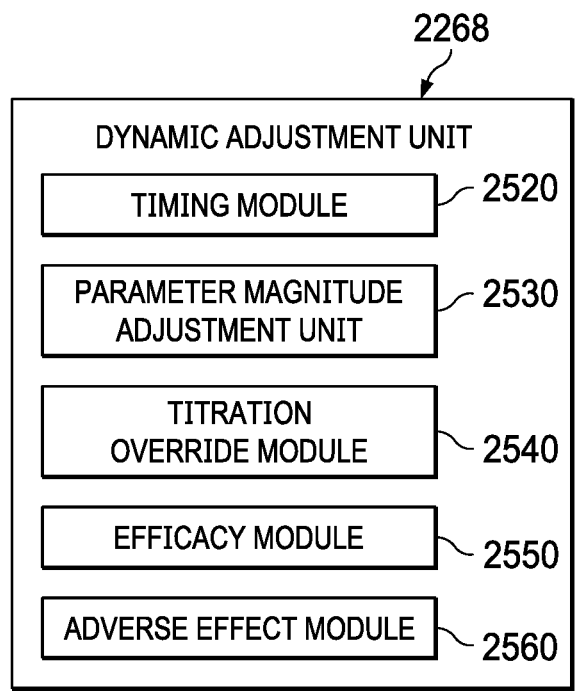
FIG. 25 shows a schematic diagram of a dynamic adjustment unit, according to some embodiments of the present disclosure.

Returning to FIG. 22, the medical device 2200 may comprise a feedback module 2280 configured to provide feedback data from the patient's body, wherein the feedback comprises at least one of body data (e.g., that provided by body data module 2270) or a manual input from the patient (e.g., provided by patient input device 2216). The feedback module 2280 may provide feedback relating to the efficacy of the treatment, the safety of the treatment, one or more body reactions to the treatment, etc. The feedback module 2280 may also provide external feedback received from the patient or a medical professional. Information from the feedback module 2280 may be used to adjust the titration of the therapy Turning now to FIG. 25, the dynamic adjustment unit 2268 may also comprise a parameter magnitude adjustment unit 2530, a timing module 2520, an efficacy module 2550, an adverse effect module 2560, and a titration override module 2540. The parameter magnitude adjustment unit 2530 may be configured to provide data relating to the magnitude of one or more adjustments to be made to the value of an electrical therapy parameter. The timing module 2520 may be configured for determining the timing of one or more adjustments to be made to the value of an electrical therapy parameter to be titrated (e.g., the length of time the electrical parameter is kept at a particular value, and/or the times at which the parameter is adjusted to a next value or a previous value). Data from the parameter magnitude adjustment unit 2530 may be utilized by the timing module 2520 to determine the timing of the adjustments to the electrical therapy parameters.

The adverse effect module 2560 (which may also be referred to as a side effect module) may be configured to determine at least one adverse effect of the electrical therapy, e.g., an observation that the treatment regimen is unsafe and/or intolerable. Data from the adverse effect module 2560 may be used by the parameter magnitude adjustment unit 2530 and/or timing module 2520 to determine the rate of increase for titrating one or more parameters of the electrical therapy signal. For example, if the adverse effect module detects that certain parameter values of the electrical signal, at a certain point in the therapy titration process, cause an adverse event (e.g., pain, vocal problems, sudden drop in blood pressure or heart rate, etc.), the parameter magnitude adjustment unit 2530 may reduce the rate of increase of an electrical therapy parameter, maintain the current value of the parameter, or may reduce the value of the parameter, to allow the adverse event to resolve. In some embodiments, these actions may be taken for more than one electrical therapy parameter. Further, the adverse effect module 2560 may correlate certain titration adjustments to adverse effects and store such data. This data may be used by medical device 2200 to control parameters of future titrations.

In one embodiment, the dynamic adjustment unit 2268 may include an efficacy module 2550 configured to determine at least one body index comprising a measure of efficacy of the electrical therapy. The efficacy index may be determined based at least in part on collected body data or on reports or input from the patient. In some embodiments, the dynamic adjustment unit 2268 may be configured to adjust the value of an electrical parameter to be titrated based on the one or more efficacy index values. Depending upon whether the efficacy module 2550 indicates that the therapy is efficacious, not efficacious, or is indeterminate, the titration process may be modified (e.g., accelerated, interrupted or suspended, or reversed, among others). More particularly, data from the efficacy module 2550 regarding the efficacy of the electrical therapy may be used by the parameter magnitude adjustment unit 2530 to make automated adjustments to the titration parameter(s), and/or by the timing module 2520 to change the timing of the adjustments to the parameter(s). As a non-limiting example, if the efficacy data indicates that the previously applied treatment was not sufficiently efficacious within a predetermined time period, the electrical therapy signal may be changed by increasing the magnitude of the adjustment to be made to an electrical therapy parameter, and/or decreasing the time period required before the next adjustment is made, in an effort to increase the electrical therapy dosage provided to the patient. In alternative embodiments, the efficacy module 2550 may instead be a component of another portion of the medical device 2200 rather than the dynamic adjustment unit 2268.

The term "reduce" the value of the electrical parameter is used above in view of the typical situation where the titration of the electrical parameter is from a low initial value to a high target value associated (or expected to be associated) with efficacy. This is generally the case for amplitude, pulse width, and pulse frequency. An adverse effect may result from a titration with too high a step magnitude or step rate, or with a step implemented too soon (i.e., with a step interval that is too short) for the patient to have acclimated to a prior titration increase. In such cases, reducing the value may be appropriate to minimize or reverse the adverse effect. However, some parameters, e.g., signal off-time, may be titrated from a high initial value to a low target value associated with efficacy. In such situations, increasing the value of the signal off-time may be appropriate to minimize or reverse the adverse effect, and to allow the patient a longer period of time to become habituated or acclimated to a particular titration increase.

The dynamic adjustment unit 2268 may also comprise a titration override module 2540 for overriding the programmed titration of the electrical therapy parameter(s). For example, based upon a signal from the adverse effect module or an input from the patient or a healthcare provider, the titration override module 2540 may override the programmed titration. The overriding of the titration may include suspending a next planned adjustment to the one or more electrical therapy parameters being titrated. Subsequent adjustments to the electrical therapy parameter(s) may be provided according to data generated by one or more of timing module 2520, the parameter magnitude adjustment unit 2530, efficacy module 2550, and adverse effect module 2560. The subsequent adjustments may include stopping a current titration process and implementing a default titration process, ending the titration process altogether, implementing a slower titration process, implementing titration to a higher (or lower) final value, etc.

FIG. 23 shows a block diagram depiction of a medical device 2200, in accordance with one illustrative embodiment of the present invention. FIG. 23 depicts an exemplary implementation of the body data module 2270 described above with respect to FIG. 22. The body data module 2270 may include a body data memory 2351 for storing and/or buffering data in the body data module 2270. The body data memory 2351 may, in some embodiments, be adapted to store body data for logging or reporting purposes and/or for future body data processing. The body data module 2270 may also include one or more body data interfaces 2310. The body data interface 2310 may provide an interface for input/output (I/O) communications between the body data module 2270 and body data units/modules (e.g., [2360-2370], [2373-2376]) via connection 2380. Connection 2380 may a wired or wireless connection, or a combination of the two. The connection 2380 may be a bus-like implementation or may include an individual connection (not shown) for each or some number, of the body data unit (e.g., [2360-2370], [2373-2376]). The connection 2380 may also include connection elements as would be known to one of skill in the art having the benefit of this disclosure. The specific implementation of the connection 2380 does not serve to limit other aspects of various embodiments described herein unless specifically described. In this regard, body data acquisition units/modules 2360, 2370, 2373, 2374, 2375 may also include one or more of sensors 2214 and leads 2215 (FIG. 22).

In various embodiments, the body data units may include, but are not limited to, an autonomic data acquisition unit 2360, a neurologic data acquisition unit 2370, and endocrine data acquisition unit 2373, a metabolic data acquisition unit 2374 and/or a tissue stress marker data acquisition unit 2375. In one embodiment, the body data units may include a physical fitness determination unit 2376. In one embodiment, the autonomic data acquisition unit 2360 may include a heartbeat data acquisition unit 2361 adapted to acquire heart sounds, EKG data, PKG data, heart echo, apexcardiography and/or the like, a blood pressure acquisition unit 2363, a respiration acquisition unit 2364, a blood gases acquisition unit 2365, and/or the like. In one embodiment, the neurologic data acquisition unit 2370 may contain a kinetic unit 2366 that may comprise an accelerometer unit 2367, an inclinometer unit 2368, and/or the like; the neurologic data acquisition unit 2370 may also contain a responsiveness/awareness unit 2369 that may be used to determine a patient's responsiveness to testing/stimuli and/or a patient's awareness of their surroundings. These lists are not inclusive, and the body data module 2270 may collect additional data not listed herein, that would become apparent to one of skill in the art having the benefit of this disclosure. The body data acquisition units ([2360-2370], [2373-2376]) may be adapted to collect, acquire, receive and/or transmit heart beat data, EKG data, PKG data, heart echo, apexcardiography, heart sound data, blood pressure data, respiration data, blood gases data, body acceleration data, body incline data and/or the like.

The body data interface(s) 2310 may include various amplifier(s) 2320, one or more A/D converters 2330 and/or one or more buffers 2340 or other memory (not shown). In one embodiment, the amplifier(s) 2320 may be adapted to boost incoming and/or outgoing signal strengths for signals such as those to/from any body data units/modules (e.g., ([2360-2370], [2373-2376]) or signals to/from other units/modules of the IMD 2200. The A/D converter(s) 2330 may be adapted to convert analog input signals from body data unit(s)/module(s) (e.g., ([2360-2370], [2373-2376]) into a digital signal format for processing by controller 2210 (and/or processor 2215). Such analog signals may include, but is not limited to, heart beat data, EKG data, PKG data, heart echo, apexcardiography, heart sound data, blood pressure data, respiration data, blood gases data, body acceleration data, body incline data and/or the like. A converted signal may also be stored in a buffer(s) 2340, a body data memory 2351, or some other memory internal to the IMD 2200 (e.g., memory 2217) or external to the IMD 2200 (e.g., patient input device 2216 or programmer 2252). The buffer(s) 2340 may be adapted to buffer and/or store signals received by the body data module 2270 as well as signals to be transmitted by the body data module 2270. In various embodiments, the buffer(s) 2340 may also be adapted to buffer and/or store signals in the body data module 2270 as these signals are transmitted between components of the body data module 2270.

Figure 26:
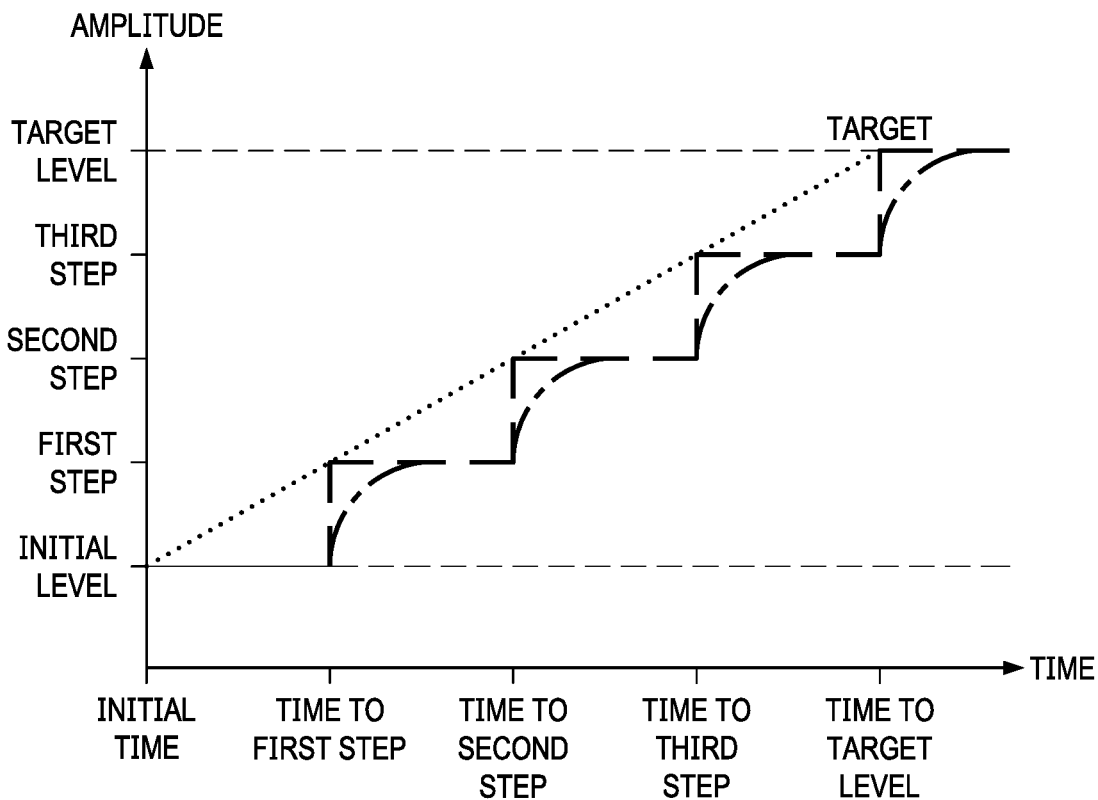
FIG. 26 shows an example of a titration comprising a series of increasing adjustments to a first electrical parameter from a first value to a first target value, according to some embodiments of the present disclosure.

FIG. 26 depicts a stylized depiction of one example of a titration of an electrical therapy, according to some embodiments herein. In one embodiment, the illustration in FIG. 26 may represent a titration of a first electrical therapy parameter, e.g., the current amplitude of the therapy signal. In alternative embodiments, the illustration of FIG. 26 may represent a titration of a plurality of parameters, e.g., a composite representation of amplitude and pulse width or frequency. Additional but different figures, having different timing and magnitude for the adjustments, could be provided for a second, third, fourth, etc., parameter to be titrated. Those skilled in the art having benefit of the present disclosure would appreciate that the general principles of FIG. 26 are applicable to any electrical parameter that may be part of a titration of an electrical therapy of a patient by adjusting the parameter from a first value to a target value.

Starting from a first or initial magnitude shown in FIG. 26, the first electrical therapy parameter may be increased by a titration step magnitude (dashed line shown in FIG. 26 as being the same for each step but which may be different in alternative embodiments) at each of a plurality of titration step intervals (also depicted as uniform in FIG. 26 but which may be different in alternative embodiments. The period from the initial time (when the therapy is started) to the time at which the target value is reached is the titration time period. From the initial time to 1st step, the electrical therapy parameter remains at the first value to allow the patient's body to be acclimated to the therapy signal at the first value. At the first step, the first parameter value is increased to a second, higher value (e.g., from 0.1 to 0.2 mA), and it remains at that value for the titration step interval, at the lapse of which the first parameter value is then increased (at the 2nd step) to a 3rd, still higher value. The first parameter remains at the 3rd value for another titration step interval, at which time (the 3rd step), when the value is raised to a 4th value. After the lapse of another titration step interval, the first parameter is then increased (at the 4th step) to the target value. The representative process illustrated may be made in a greater number of steps with smaller titration step magnitudes to improve the patient's ability to tolerate each step. The stepwise process is repeated until the target value of the first parameter is reached. The time to target value may be determined by the timing module 2520 (FIG. 25) of the dynamic adjustment module 2270.

FIG. 26 also shows the titration rate on two timescales, e.g., a global time scale (dotted line), comparable in value to the sum of the titration step magnitudes divided by the time to target level, and local time scales (dashed and dashed-dotted lines), indicating alternative approaches to bringing the amplitude up to the level of a next step.

The patient's tolerance for an increase in a titrated parameter may vary depending on the patient's state, e.g., the patient's level of consciousness, level of attention, mood, general health, gender, age, etc. Changes in the titration process may be made accordingly. For example, if the patient is more tolerant of the increase at night, a current setting may be increased at night (e.g., while the patient is asleep) from a lower amplitude to a higher amplitude. Upon awakening, the amplitude may be maintained at the higher amplitude or reduced to an intermediate value if the patient does not tolerate the higher amplitude when awake. In this manner, the titrating function may accelerate the patient's accommodation to the higher amplitude and/or accelerate the overall titration process.

Figure 27:
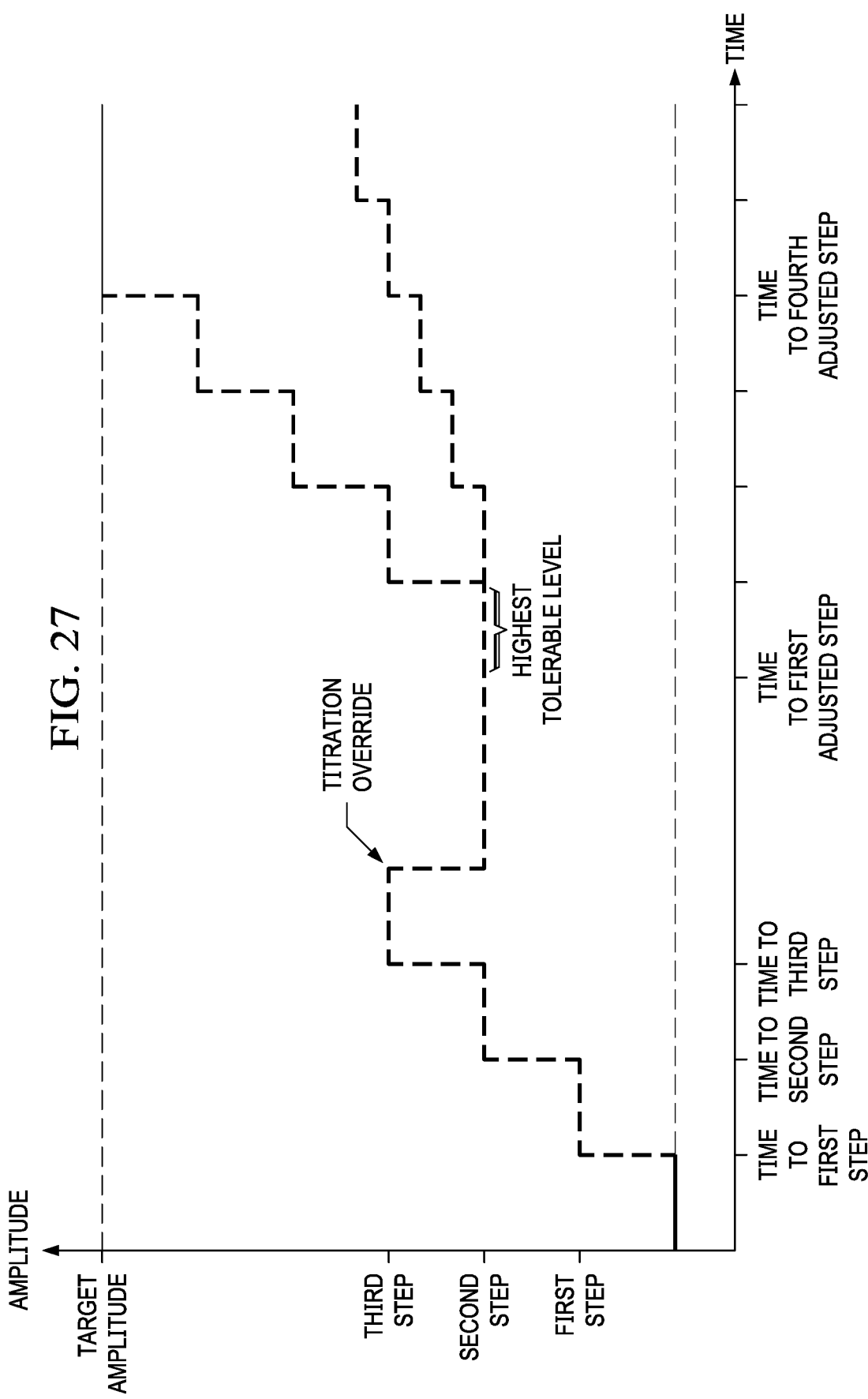
FIG. 27 shows examples of a titration of a first electrical parameter involving a dynamic adjustment to a programmed titration, according to some embodiments of the present disclosure.

FIG. 27 illustrates a stylized depiction of one example of a dynamic adjustment of a titration function, according to some embodiments. Again, by way of example, the depicted value along the y-axis of FIG. 27 is the first electrical therapy parameter, e.g., current amplitude. The general principles illustrated, however, are applicable to any electrical therapy parameter that may be titrated as part of a therapy titration to an efficacious dosage. In this example, an adverse effect (not shown) is determined to occur sometime after titrating up to the 3rd step. As shown, the dynamic adjustment comprises reducing the value of the first parameter, e.g., current amplitude, to the last known tolerable value (e.g., the value of the 2nd step), lengthening of the duration of the current tolerable/safe magnitude before the first parameter is titrated to the next higher magnitude. In one embodiment, subsequent steps may be initiated at the originally programmed step magnitude, as illustrated by the series of steps leading to the target value (dashed line), while in alternative embodiments, the dynamic adjustment may also or alternatively comprise decreasing the step magnitude to be applied at future titration steps, as shown by the adjusted steps having a smaller magnitude than the earlier (1st, 2nd and 3rd) step magnitudes (dotted line).

In embodiments having a reduced step magnitude, a new (greater) titration time period for reaching the target value may be determined. That is, upon detection of an adverse event, the titration step magnitude may be reduced for future titration steps resulting in a longer titration time period necessary to reach the target value for the electrical therapy parameter(s) being titrated. In this manner, a more comfortable and/or safer titration process may be provided to the patient.

Figure 28:
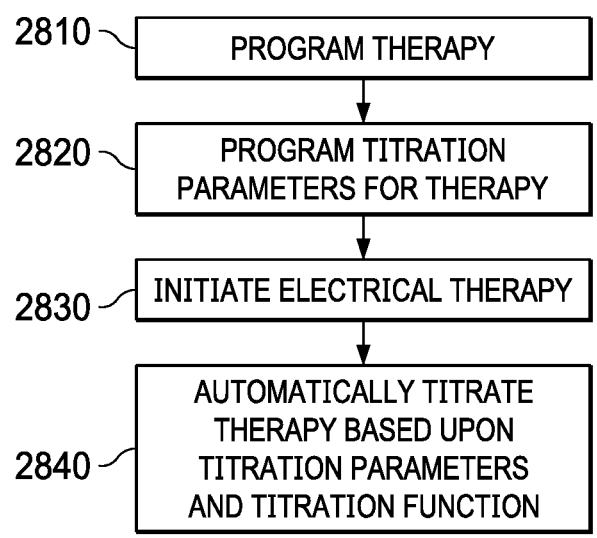
FIG. 28 shows a flowchart depiction of a method, according to some embodiments of the present disclosure.

FIG. 28 illustrates a flowchart representation of a method 2800 for performing an automated titration of one or more electrical therapy parameters in accordance with some embodiments herein. Parameters defining an electrical therapy may be programmed (block 2810) into a medical device based upon at least one target value for an electrical parameter to be titrated (e.g., an electrical therapy that the patient cannot immediately tolerate at the dosage associated with the target value). The therapy regimen may be configured to treat one or more of several diseases, such as epilepsy, depression, pain, congestive heart failure, traumatic brain injury, or obesity.

Programming at 2810 may include providing first value(s) and target value(s) for at least one parameter.

One or more titration parameters characterizing the titration of the one or more electrical therapy parameters being titrated may be programmed into the medical device (block 2820). The electrical therapy may be implemented with the electrical therapy parameters to be titrated having their first or initial values (block 2830). Thereafter, the electrical therapy may be automatically titrated (block 2840) based on the programmed target value(s) of the electrical parameter(s), the titration parameters, and a titration function. The titration function may include various patterns for adjusting the electrical therapy parameter(s), e.g., uniform titration magnitude steps and titration step intervals, or non-uniform adjustments (e.g., according to a parabolic function, a higher-order polynomial, etc.).

In some embodiments, the method 2800 may further comprise sending a message to the patient and/or a caregiver or healthcare provided a physician when the target value is reached, or when a change to the programmed titration has occurred, or when a side effect has been detected.

Figure 29:
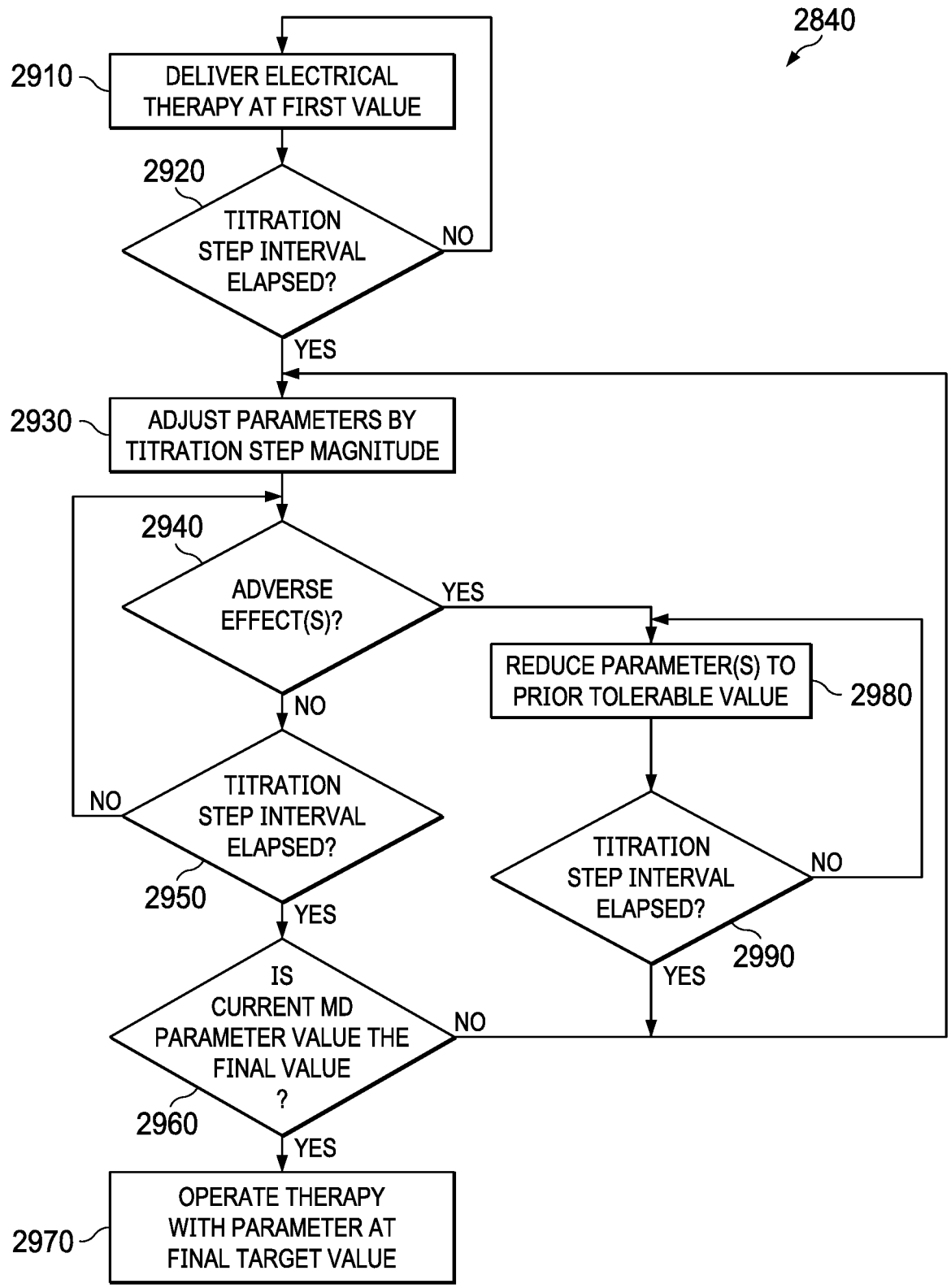
FIG. 29 shows a flowchart depiction of a method, according to some embodiments of the present disclosure.

FIG. 29 illustrates a flowchart depiction of automatically titrating the electrical therapy based upon the titration parameters and the titration function (block 2840 of FIG. 28), in accordance with some embodiments herein. At block 2910, the medical device 2200 may deliver the therapy at the first (initial) values for the electrical therapy parameters programmed into the medical device.

As the therapy is delivered, logic in the MD 2200 determines whether or not the titration step interval has elapsed (block 2920). If so, the electrical therapy parameter(s) to be titrated are adjusted by the titration step magnitude (block 2930).

In one embodiment, titration logic in the MD 2200 determines whether or not an adverse effect has occurred (block 2940). If no adverse event has occurred, the logic thereafter checks to determine if the next titration step interval has elapsed (block 2950). If the titration step interval has not elapsed, the logic continues to check for adverse effects (block 2940), and if the titration step interval has elapsed, the logic checks to determine if current value of the electrical signal parameter is the final value (block 2960). If the current value is the final value, MD 2200 continues to operate the therapy with the parameter at the target value (block 2970), while if the final titration value has not been reached, the logic again adjusts the electrical therapy by the titration step magnitude (block 2930).

If at any point after an adjustment is made (block 2930) an adverse effect occurs (block 2940), the value of the electrical therapy parameter is reduced to a prior tolerable value (block 2980), e.g., a highest previously tolerable amplitude. In some embodiments, changes to one or more of the titration step magnitude and the titration step interval may also be made as part of block 2980. In alternative embodiments, the therapy may be suspended rather than continued at a reduced stimulation dosage. After the reduction of the electrical therapy parameter to a lower value (with or without changes to the step magnitude and/or interval), the logic then checks to determine if the titration step interval has elapsed (either as originally programmed or as modified) at step 2990. If the interval has elapsed, the electrical therapy parameter is adjusted by the titration step magnitude at step 2930.

The indications of an adverse effect or event (2940) may be based on one or more body indices derived from a body signal. Exemplary body indices include one or more of the patient's heart rate, heart rate variability, blood oxygen saturation, respiratory rate, blood oxygen saturation variability, respiratory rate variability, discomfort, shortness of breath, or vocal cord function. Unacceptable changes indicative of a lack of patient tolerance may be used to indicate the occurrence of an adverse effect. Alternatively or in addition, a manual input from the patient or another external source, such as a medical professional, may be used to indicate an adverse effect. Exemplary manual inputs include but are not limited to tap sensor inputs, magnetic sensor inputs, manipulation of one or more physical or virtual keys on a handheld device, etc.

In some embodiments, the adverse event indication may include a severity of the adverse effect, or to the rate of occurrence of an effect that at a low rate would not be an adverse effect. When adverse events occur, the magnitude of the reduction of the electrical signal parameter and/or changes to the titration step interval and step magnitude (block 2980) may be based on the type, severity and/or rate of the adverse effect.

In some embodiments, if no adverse effect is determined at block 2940 to have occurred, then the current and/or a future second period can be shortened, i.e., the titration of the parameter may take place more rapidly than originally programmed if there are no significant adverse effects.

Figure 30:
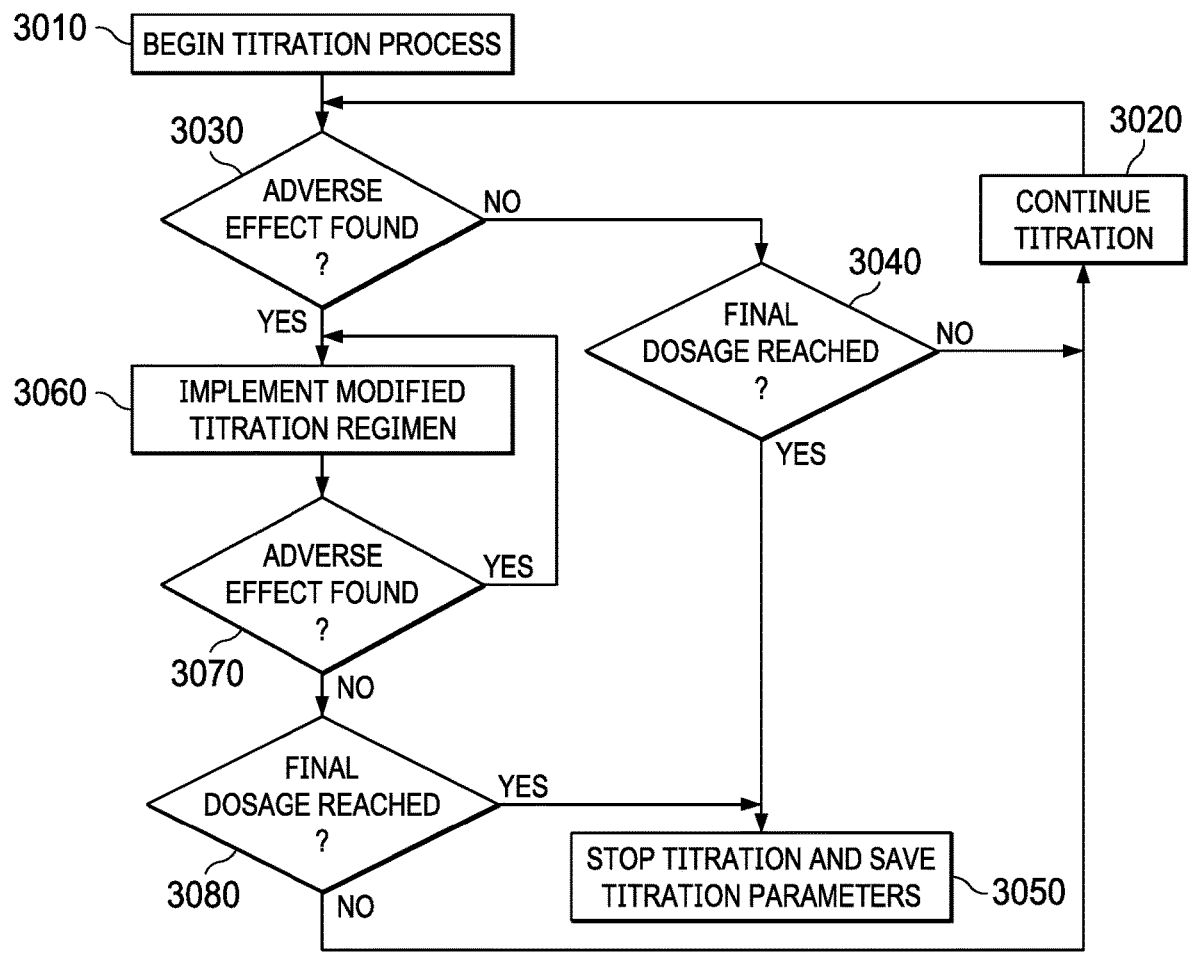
FIG. 30 shows a flowchart depiction of a method for performing a titration process, according to some embodiments of the present disclosure.

Turning to FIG. 30, a simplified flowchart diagram for performing a titration process in accordance with some embodiments herein is illustrated. A dosage for providing a therapy may be determined, and based upon the dosage, a titration regimen may be initiated (block 3010). In some embodiments, the titration regimen is based upon the dosage and/or one or more specific characteristics of the patient, e.g., patient tolerance level.

Upon performing one or more upward titration steps, one or more body data may be received and analyzed to determine whether there exists an adverse effect (block 3030). In other embodiments, an external source may provide the medical device 2200 an indication of an adverse effect. For example, the patient may provide a manual input that is indicative of an adverse effect. In other embodiment, the medical device 2200 may receive a signal from an external device, indicating an adverse effect.

Upon a determination that no adverse effect has been found (block 3030), the medical device may determine whether the final dosage has been reached (block 3040). If the final dosage has been reached, the medical device may stop the titration process and save the titration parameters (block 3050). Upon a determination that the final dosage has not been reached (block 3040), the medical device may continue the titration process (block 3020), e.g., by implementing a next titration step upon the passage of a titration step interval. The process may continue as previously discussed (e.g., by returning to block 3030).

If the medical device 2200 determines that at least one adverse effect has been found (block 3030), the medical device 2200 may implement a modification of the titration regimen (block 3060). This modification may be automatically performed based upon the type of adverse effects detected. Alternatively, or in addition, manual input from a person, or automated input based upon body data, may also affect modification of the titration regimen.

Upon implementing the modified titration regimen, the medical device 2200 may again determine whether an adverse effect has been found (block 3070). If an adverse effect is found, the medical device 2200 may again implement a modification of the titration regimen (as indicated by the path from block 3070 to 3060). If an adverse effect is not found (block 3070) and the final dosage has been reached (block 3080), the titration process is terminated and the titration parameters are saved (block 3050). If the final dosage has not been reached (block 3080), the medical device 2200 may continue the titration process, moving the titration in the direction of the final dosage (see path from block 3080 to 3020). In this manner, an automated and/or manual implementation of a titration regimen, moving upwardly towards the therapy dosage, is implemented while reducing the risk of adverse effects.

Figure 31:
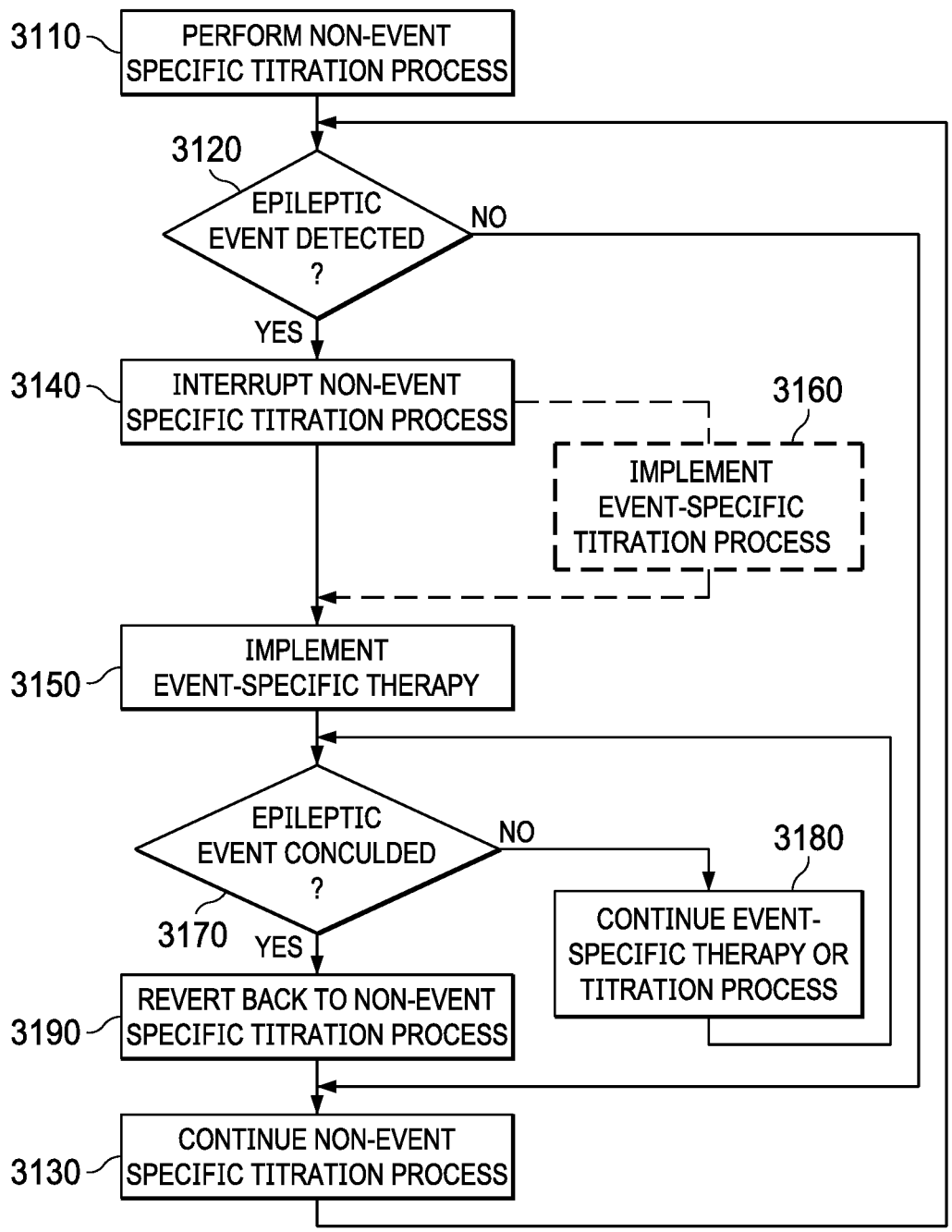
FIG. 31 shows a flowchart depiction of a method for implementing a titration interrupt and/or a multi-titration process, according to some embodiments of the present disclosure.
Figure 32:
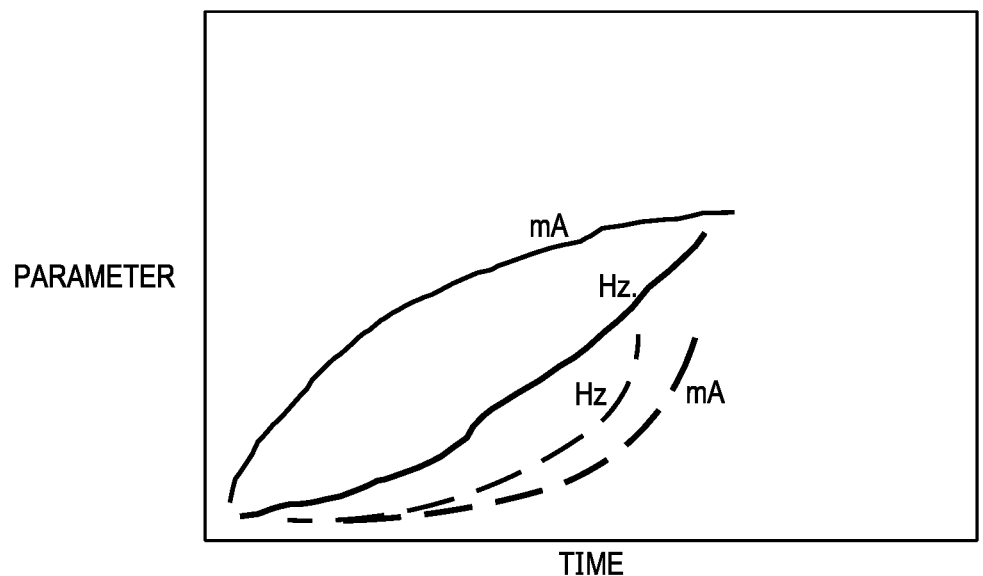
FIG. 32 shows exemplary titration functions for two parameters, according to some embodiments of the present disclosure.
Figure 33:
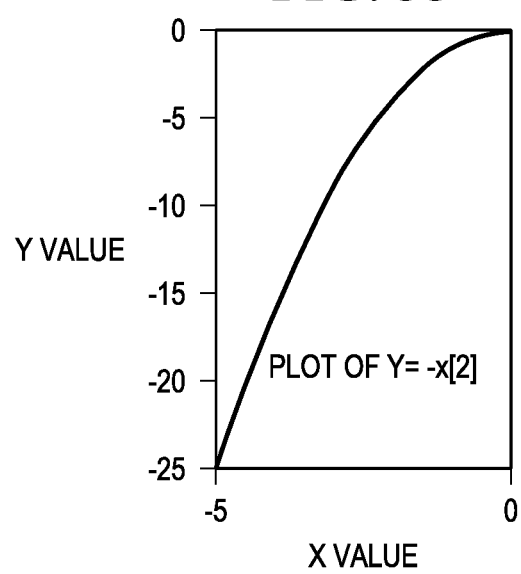
FIG. 33 shows an exemplary titration function, according to some embodiments of the present disclosure.

Turning now to FIG. 31, a flowchart diagram for a method of implementing a titration interrupt and/or a multi-titration process, in accordance with some embodiments is illustrated. Upon determining a dosage for therapeutic treatment stimulation for a disease such as epilepsy, a non-event-specific state titration process may be initiated (block 3110). The non-event-specific state titration process is performed to automatically initiate a treatment regimen, to gradually reach a full dosage regimen to treat a condition (e.g., epilepsy). The non-event-specific state titration is performed at pre-programmed times and in pre-programmed steps independent of the occurrence of seizures, (e.g., open-loop process). That is, in some embodiments, the non-event-specific state titration process may be not responsive to a particular epileptic event. In one embodiment, the non-event-specific state titration process may be implemented in the manner described in FIG. 30.

Continuing referring to FIG. 31, the medical device 2200 may continuously check to determine whether an epileptic event (e.g., a seizure, a fall associated with a seizure, an accident associated with a seizure, etc.) is detected (block 3120). If no epileptic events are detected, the non-event-specific state titration process is continued (block 3130). If and when an epileptic seizure is detected, the non-event-specific state titration process may be temporarily interrupted (block 3140). Upon interrupting the non-event-specific state titration process, in one embodiment, the medical device 2200 may implement an event-specific therapy (block 3150) (e.g., closed-loop). The event-specific therapy may be a specific therapy regimen that is directed to treat the specific type of event (e.g., seizure) that is detected. For example a 1st therapy signal may be provided for a clinical seizure, while 2nd therapy may be provided for a sub-clinical seizure. In other embodiment, a 1st therapy signal may be provided for a generalized seizure, while a 2nd therapy signal may be provided for a partial seizure. In yet other embodiments, other distinctions for seizures (e.g., simple partial or complex partial or secondarily generalized seizure etc.) may be used to implement specific therapy signals tailored to address those distinctions. In some embodiment, a look-up function may be performed to select the various parameters (e.g., frequency, pulse-train parameters, pulse-width, inter-pulse interval, amplitude, etc.) relating to the therapy signal. The event-specific therapy/titration process may be closed-loop process, specific to the treatment of the epileptic event, wherein this process terminates with the epileptic event.

In an alternative embodiment, upon interrupting the non-event-specific state titration process (block 3140), an event-specific titration process may be implemented (block 3160). The event-specific titration process may provide for determining a dosage to treat the specific epileptic event that has been detected, and initiate a treatment regimen using parameter settings that are increased to a full-dosage setting to treat the epileptic event. Upon implementing the event-specific (e.g., closed-loop) titration process, the medical device 2200 may then implement an event-specific therapy based upon the event-specific titration. In one embodiment, the time-periods relating to the step-wise increases in one or more parameters associated with the event-specific titration process are equal to or larger than those relating to the non-event-specific state titration process. The event-specific therapy/titration process may be closed-loop process, specific to the treatment of the detected epileptic event, wherein this process terminates with the epileptic event.

Upon performing either of the two processes of blocks 3140 and 3160 (event-specific therapy or event-specific titration), the medical device 2200 may determine whether the epileptic event had concluded or sufficiently subsided (block 3170). Upon a determination the epileptic event has not sufficiently subsided, the event-specific therapy or event-specific titration is continued (block 3180). Upon a determination the epileptic event has concluded or has sufficiently subsided, the medical device 100 may revert back to the non-event-specific state titration process (block 3190).

In some embodiments, the present disclosure may relate to a method of providing a bringing an electrical stimulation regimen administered by a medical device to a target dosage, comprising programing a therapy regimen based upon at least one target electrical parameter; programming one or more titration parameters for titrating to the target electrical parameter; initiating the electrical therapy at the programmed initial values; receiving a body signal after initiating the therapy at the programmed initial values; determining whether there is an adverse effect associated with the therapy, based upon the body signal; adjusting one or more titration parameters to yield an adjusted titration, in response to a determining that there is an adverse effect associated with the therapy; implementing the adjusted titration, and titrating the at least one target electrical parameter according to the adjusted titration.

Receiving the body signal may comprise receiving at least one of autonomic data, neurological data, endocrine data, metabolic data, tissue stress marker data, responsiveness data, or physical fitness data.

Adjusting may comprise returning the electrical parameter value to a prior value. The adjusted therapy may be safe, efficacious, and/or tolerable.

This method may further comprise alerting a physician, in response to a cardiac or respiratory adverse effect.

This method may further comprise determining an efficacy of the adjusted therapy. This method may further comprise stopping the titration process and notifying a physician, in response to the adjusted therapy being efficacious before the target parameter is reached.

In some embodiments, the target electrical parameter may be selected from an amplitude, a pulse width, a pulse frequency, a signal on-time, a waveform, a level or degree of charge balance in a pulse, a polarity, a signal off-time, or two or more thereof. For example, adjusting the therapy may comprise at least one of reducing an electrical current amplitude of the electrical parameter, or determining a modified titration function.

In some embodiments, increasing the electrical parameter value may be performed during states in which taking said step is most comfortable or safe. For a therapy such as vagus nerve stimulation that may cause throat discomfort or coughing, increasing the electrical parameter may be performed while the patient is asleep when the discomfort or pain thresholds are higher than during wakefulness. In some embodiments, the titration may comprise detecting a patient state, where the patient state is one or more of sleeping, awake, resting awake, sitting and awake, active and awake, and exercising. Detecting whether the patient is sleeping may further comprise detecting a sleep state of the patient selected from stage 1, stage 2, stage 3, stage 4, and REM sleep, light sleep, and deep sleep. In some embodiments, where the electrical therapy may use bradycardia, increasing the electrical parameter value may take place only while the patient is awake to minimize the risk of not detecting symptoms associated with the slowing down of the patient's heart rate.

The electrical stimulation regimen of this method may be configured to treat epilepsy, depression, pain, congestive heart failure, traumatic brain injury, or obesity.

In any of the automatic titration methods described herein, the titration may be suspended at any step upon the detection of an acute manifestation of the patient's illness, e.g., a seizure if the patient suffers epilepsy, and an alternative, closed-loop therapy to treat the acute manifestation may be implemented. (The acute therapy may involve a second titration process. Further, the second titration process may be implemented by a function that uses as input(s) information regarding the first titration process). Upon termination of the acute manifestation, the titration may be resumed, typically at the step at which it was suspended. In some embodiments, however, the titration may be resumed at a higher or lower step.

In some embodiments, a method is provided for performing an interruption of a non-event specific titration process (e.g., open-loop) performed by an implanted medical device, comprising: a) programming the medical device to provide an electrical therapy, wherein the programmed electrical therapy comprises a first target value for a first electrical therapy parameter defining the electrical therapy; b) programming at least one titration parameter for automatically adjusting the first electrical therapy parameter from a first value to the first target value over a titration time period of at least two days, wherein the at least one titration parameter is selected from the titration time period, a titration step interval, a titration step magnitude, and a titration step rate; initiating the electrical therapy, wherein the first electrical therapy parameter comprises said first value; c) automatically titrating the electrical therapy by making a plurality of adjustments to the value of the first electrical therapy parameter, whereby the first electrical therapy parameter is changed from the first value to a second target value according to a titration function; d) detecting an epileptic event; e) interrupting the open-loop titrating process in response to detecting an epileptic event; f) providing an event-specific (e.g., closed-loop) therapy; and g) reverting back to the non-event specific titration process in response to a determination that the epileptic event has concluded.

In other embodiments, a method is provided for performing an interruption of a non-event specific titration process performed by an implanted medical device, comprising: a) performing a non-event specific titration process; b) detecting an epileptic event; c) interrupting the non-event specific titration process in response to detection the epileptic event; d) implementing an event-specific titration process for delivering a therapy in response the detection of the epileptic event; and e) reverting back to the non-event specific titration process in response to a determination that the epileptic event has concluded.

In yet another embodiment, a method is provided for modifying a titration process for providing a therapy by a medical device (fully implanted, partially implanted or external to the patient) comprising: a) initiating a titration process to treat a chronic condition, wherein the titration process includes programming at least one titration parameter for automatically adjusting an electrical therapy parameter from a first value to the first target value over a titration time period; b) determining whether an adverse effect resulting from the titration has been found; c) modifying at least one parameter associated with the titration process; and d) implementing a modified titration process. In some embodiments, the titration process and/or the modified titration process is continued upon determining that a final dosage of the therapy had been reached.

The methods described above may be implemented by the medical device 2200 and/or the medical device system 2251. The methods described above may be governed by instructions that are stored in a non-transitory computer readable storage medium and that are executed by, e.g., a processor 2217 of the medical device 2200.

The methods depicted in FIGS. 28-31 and/or described above may be governed by instructions that are stored in a non-transitory computer readable storage medium and that are executed by, e.g., a processor 2217 of the medical device 2200. Each of the operations shown in FIGS. 28-31 and/or described above may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

In one embodiment, a method of treating a medical condition in a patient using an implantable medical device, the implantable medical device including a first electrode coupled to a first cranial nerve structure and a second electrode coupled to a second cranial nerve structure, where the first cranial nerve structure is a left portion of a cranial nerve and the second cranial nerve structure is a right portion of the cranial nerve, the method may include: providing a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal, the first electrical signal utilizing a titrating procedure to reach a target value; switching from the first polarity configuration to a second polarity configuration upon termination of the first electrical signal where the first electrode functions as the anode and the second electrode functions as the cathode in the second polarity configuration; and/or providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal.

In addition, the method may include initiating a second titration period for a second therapy with a second treatment period; initiating a third therapy based on an acute event detection; and/or initiating a second therapy based on an acute event detection. Further, one or more changes in one or more values associated with one or more parameters during a first titration period do not cause an adverse effect. In addition, the method may receive an input from the patient where the input obtained from the patient occurs via a magnetic sensor input. Further, one or more processors of the implantable medical device may modify at least one of a first titration period and a modification procedure of one or more values associated with one or more parameters based on at least one of a patient's age, a patient's level of consciousness, a patient's level of attention, a patient's health status, a patient's gender, a severity of a disorder being treated, a patient's tolerance to one or more adverse events, and/or a patient's tolerance to pain. In addition, the method may include: initiating via one or more processors of the implantable medical device a second titration period for a second therapy with a second treatment period, the second therapy including a second electrical stimulation with a second set of parameters; initiating a second modification procedure based on the second set of parameters with a second set of target values; and/or initiating the second therapy for the second treatment period based on at least one parameter of the second set of parameters being tolerated by the patient or reaching at least one of the second set of target values. Further, the one or more processors of the implantable medical device may modify at least one of a first titration period and a modification procedure of one or more values associated with the one or more parameters based on at least one of an emergence of one or more side effects, a level of efficacy, and an event detection. In addition, the event detection may be an acute event detection. The method may include acquiring data for at least one of a status report, a historical report, and an alert and transmitting the acquired data or the alert to an external device. Further, the one or more processors may modify at least one of the titration period and a modification procedure of one or more values associated with one or more parameters based on the patient being asleep.

In another embodiment, a method of treating a medical condition in a patient using an implantable medical device, the implantable medical device including a first electrode coupled to a first cranial nerve structure and a second electrode coupled to a second cranial nerve structure, where the first cranial nerve structure is a left portion of a cranial nerve and the second cranial nerve structure is a right portion of the cranial nerve, the method may include: providing a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal, the first electrical signal utilizing a titrating procedure to reach a target value; switching from the first polarity configuration to a second polarity configuration upon termination of the first electrical signal where the first electrode functions as the anode and the second electrode functions as the cathode in the second polarity configuration; and/or providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal where a titration time interval is a time associated with the adverse effect not recurring in response to an electrical stimulation using an electrical stimulation value, where the electrical stimulation value had previously elicited an adverse effect.

In addition, a time of a resumption of a titration process for the first electrical signal is based on at least one of: a patient's age, a patient's health status, a severity of the adverse effects, and/or a severity of seizures. Further, an upward titration to a seizure value may be implemented in a transient period in response to a seizure detection where the seizure value utilized for the upward titration is a value which was intolerable during a non-seizure period. In addition, the method may include accelerating a titration process based on achieving a first target value without adverse effects. Further, a titration function may be non-uniform. Further, a titration parameter, a titration function and a titration period may utilize different values during a wakefulness period and a sleep period. In addition, the at least one body signal is an evoked response. Further, the method may include determining a seizure severity and/or selecting at least one of: a titration function and a titration period based on the seizure severity determination.

What is claimed:

1. A method of treating a medical condition in a patient using a medical device, the medical device including a first electrode coupled to a first cranial nerve structure and a second electrode coupled to a second cranial nerve structure, where the first cranial nerve structure is a left portion of a cranial nerve and the second cranial nerve structure is a right portion of the cranial nerve, the method comprising:
providing a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal, the first electrical signal utilizing a titrating procedure to reach a target value;
switching from the first polarity configuration to a second polarity configuration upon termination of the first electrical signal where the first electrode functions as the anode and the second electrode functions as the cathode in the second polarity configuration; and
providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal;
wherein a titration time interval is based on a patient's age and is a time associated with an adverse effect not recurring in response to an electrical stimulation using an electrical stimulation value, where the electrical stimulation value had previously elicited the adverse effect, where the electrical stimulation is either the first electrical signal or the second electrical signal.

2. The method of claim 1, further comprising receiving an input from the patient where the input obtained from the patient occurs via a magnetic sensor input.

3. The method of claim 1, further comprising acquiring data for at least one of a status report, a historical report, and an alert and transmitting the acquired data or the alert to an external device.

4. A method of treating a medical condition in a patient using an implantable medical device, the implantable medical device including a first electrode coupled to a first cranial nerve structure and a second electrode coupled to a second cranial nerve structure, where the first cranial nerve structure is a left portion of a cranial nerve and the second cranial nerve structure is a right portion of the cranial nerve, the method comprising:
providing a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal, the first electrical signal utilizing a titrating procedure to reach a target value;
switching from the first polarity configuration to a second polarity configuration upon termination of the first electrical signal where the first electrode functions as the anode and the second electrode functions as the cathode in the second polarity configuration; and providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal;

wherein a titration time interval is based on a patient's age and is a time associated with an adverse effect not recurring in response to an electrical stimulation using an electrical stimulation value, where the electrical stimulation value had previously elicited the adverse effect, where the electrical stimulation is either the first electrical signal or the second electrical signal.

5. The method of claim 4, wherein a time of a resumption of a titration process for the first electrical signal is based on at least one of: a patient's age, a patient's health status, a severity of the adverse effects, and a severity of seizures.

\* \* \* \* \*